(12) United States Patent
Villaverde Corrales et al.

(10) Patent No.: US 12,202,866 B2
(45) Date of Patent: *Jan. 21, 2025

(54) THERAPEUTIC NANOCONJUGATES AND USES THEREOF

(71) Applicants: UNIVERSITAT AUTÒNOMA DE BARCELONA (UAB), Cerdanyola del Vallès (ES); FUNDACIÓ INSTITUT DE RECERCA DE L'HOSPITAL DE LA SANTA CREU I SANT PAU, Barcelona (ES); CONSORCIO CENTRO DE INVESTIGACIÓN BIOMÉDICA EN RED, M.P., Madrid (ES)

(72) Inventors: Antonio Pedro Villaverde Corrales, Cerdanyola del Vallès (ES); Esther Vázquez Gómez, Cerdanyola del Vallès (ES); Ugutz Unzueta Elorza, Barcelona (ES); Ramón Mangues Bafalluy, Barcelona (ES); María Virtudes Céspedes Navarro, Madrid (ES); Isolda Casanova Rigat, Madrid (ES)

(73) Assignees: UNIVERSITAT AUTONOMA DE BARCELONA (UAB), Cerdanyola de Vallès (ES); FUNDACIÓ INSTITUT DE RECERCA DE L'HOSPITAL DE LA SANTA CREU I SANT PAU, Cerdanyola del Vallès (ES); CONSORCIO CENTRO DE INVESTIGACIÓN BIOMÉDICA EN RED, M.P., Madrid (ES)

( * ) Notice: Subject to any disclaimer, the term of this patent is extended or adjusted under 35 U.S.C. 154(b) by 78 days.

This patent is subject to a terminal disclaimer.

(21) Appl. No.: 16/631,004

(22) PCT Filed: Jul. 16, 2018

(86) PCT No.: PCT/EP2018/069303
§ 371 (c)(1),
(2) Date: Jan. 14, 2020

(87) PCT Pub. No.: WO2019/012157
PCT Pub. Date: Jan. 17, 2019

(65) Prior Publication Data
US 2020/0223893 A1 Jul. 16, 2020

(30) Foreign Application Priority Data

Jul. 14, 2017 (EP) .................................... 17382461

(51) Int. Cl.
*C07K 14/47* (2006.01)
*A61K 49/14* (2006.01)
*A61K 49/18* (2006.01)

(52) U.S. Cl.
CPC ........ *C07K 14/4702* (2013.01); *A61K 49/146* (2013.01); *A61K 49/1821* (2013.01); *C07K 2319/30* (2013.01)

(58) Field of Classification Search
None
See application file for complete search history.

(56) References Cited

U.S. PATENT DOCUMENTS

| 5,082,927 | A | 1/1992 | Pastan et al. |
| 5,622,958 | A | 4/1997 | Danishefsky et al. |
| 8,394,758 | B2 | 3/2013 | Wu et al. |
| 2002/0102265 | A1 | 8/2002 | Hong et al. |
| 2004/0132642 | A1 | 7/2004 | Hwang |
| 2009/0099060 | A1 | 4/2009 | Bondarev et al. |
| 2012/0064142 | A1 | 3/2012 | Pillay et al. |
| 2014/0068797 | A1 | 3/2014 | Doudna et al. |

FOREIGN PATENT DOCUMENTS

| EP | 0513613 | A1 | 11/1992 |
| EP | 2476441 | * | 7/2012 |
| EP | 2476441 | A1 * | 7/2012 |
| WO | 2006029078 | A2 | 3/2006 |
| WO | 2006/135436 | A2 | 12/2006 |
| WO | 2007115376 | A1 | 10/2007 |
| WO | 2009046834 | A2 | 4/2009 |
| WO | 2011031477 | A2 | 3/2011 |

OTHER PUBLICATIONS

Serna et al. (Nanomedicine: Nanotechnology, Biology, and Medicine,12 (2016) 1241-1251) (Year: 2016).*
Power et al. (Mol Cancer Ther. May 2009;8(5):1015-25) (Year: 2009).*
Promega (MagneHisTM Protein Purification System, Jul. 2013) (Year: 2013).*
Hohn et al. (J Clin Oncol. Nov. 1989;7(11):1646-54) (Year: 1989).*
Altschul et al., "Basic Local Alignment Search Tool", J. Mol. Biol., 1990, pp. 403-410, vol. 215.
Armstrong et al., "A Phase I Study of Chemically Synthesized Verotoxin (Shiga-like Toxin) Pk-Trisaccharide Receptors Attached to Chromosorb for Preventing Hemolytic-Uremic Syndrome", The Journal of Infectious Diseases, 1995, pp. 1042-1045, vol. 171.
Bajorath., "Molecular Organization, Structural Features, and Ligand Binding Characteristics of CD44, a Highly Variable Cell Surface Glycoprotein with Multiple Functions", Proteins: SFG, 2000, pp. 103-111, vol. 39.
Behroozi et al., "1,2-Dithiolan-3-one 1-Oxides: A Class of Thiol-Activated DNA-Cleaving Agents that are Structurally Related to the Natural Product Leinamycin", Biochemistry, 1996, pp. 1768-1774, vol. 35.

(Continued)

*Primary Examiner* — Sergio Coffa
(74) *Attorney, Agent, or Firm* — Thompson Coburn LLP; William A. Holtz

(57) ABSTRACT

The present invention relates to nanostructured conjugates, more specifically to nanostructured fusion proteins suitable for the selective delivery of their conjugated therapeutic agents to specific cell and tissue types. It also relates to nanoparticles comprising such nanostructured proteins and the therapeutic uses thereof.

8 Claims, 29 Drawing Sheets
Specification includes a Sequence Listing.

(56) References Cited

OTHER PUBLICATIONS

Bordo et al., "Suggestions for "Safe" Residue Substitutions in Site-Directed Mutagenesis", J. Mol. Biol., 1991, pp. 721-729, vol. 217.
Brinkmann et al., "Immunotoxins against cancer", Biochimica et Biophysica Acta, 1994, pp. 27-45, vol. 1198.
Cespedes et al., "In Vivo Architectonic Stability of Fully de Novo Designed Protein-Only Nanoparticles", ACSNano, 2014, pp. 4166-4176, vol. 8, No. 5.
Chen et al., "Novel Cationic Antimicrobial Peptide GW-H1 Induced Caspase-Dependent Apoptosis of Hepatocellular Carcinoma Cell Lines", Peptides, 2012, pp. 257-265, vol. 36.
Croker et al., "Cancer stem cells: implications for the progression and treatment of metastatic disease", J. Cell. Mol. Med., 2008, pp. 374-390, vol. 12, No. 2.
Céspedes et al., "Cancer-specific uptake of a liganded protein nanocarrier targeting aggressive CXCR4 colorectal cancer models", Nanomedicine, 2016, pp. 1987-1996, vol. 12.
Ermisch et al., "On the Blood-Brain Barrier to Peptides: [3H]B=Casomorphin-5 Uptake by Eighteen Brain Regions In Vivo", Journal of Neurochemistry, 1983, pp. 1229-1233, vol. 41, No. 5.
Helissey et al., "DNA minor groove cleaving agents: synthesis, binding and strand cleaving properties of anthraquinone-oligopyrrolecarboxamide hybrids", 1996, pp. 527-551, vol. 11, No. 7.
Hesselgesser et al., "Identification and Characterization of the CXCR4 Chemokine Receptor in Human T Cell Lines: Ligand Binding, Biological Activity, and HIV-1 Infectivity", Journal of Immunology, 1998, pp. 877-883, vol. 160.
Hoffmann et al., "Structure-Function Studies of an Engineered Scaffold Protein Derived from Stefin A. I: Development of the SQM Variant", Protein Engineering, Design, and Function, 2010, pp. 403-413, vol. 23, No. 5.
Holm et al., "Studying the Uptake of Cell-Penetrating Peptides", Nature Protocols, 2006, pp. 1001-1005, vol. 1, No. 2.
Islam et al., "Structure-Activity Studies of Antitumor Agents Based on Pyrrolo[1,2-a]benzimidazoles: New Reductive Alkylating DNA Cleaving Agents", J. Med. Chem., 1991, pp. 2954-2961, vol. 34.
Kalia et al., "Advances in Bioconjugation", Curr Org Chem, 2010, pp. 138-147, vol. 14, No. 2.
Kim et al., "Cloning and Sequence Analysis of Another Shiga-Like Toxin IIe Variant Gene (slt-IIera) from an *Escherichia coli* R107 Strain Isolated from Rabbitt", 1997, pp. 805-808, vol. 41, No. 10.
Kremers et al., "Fluorescent Proteins at a Glance", Journal of Cell Science, 2011, pp. 157-160, vol. 124, No. 2676.
Lee et al., "A Novel DNA Cleaving Agent, 2,2'-BIS(2-Aminoethyl)-4,4'-Bithiazole, Induces Thymocyte Apoptosis", Biochemistry and Molecular Biology International, 1996, pp. 151-157, vol. 40, No. 1.
Liang, "CXCR4, Inhibitors and Mechanisms of Action", Chem. Biol. Drug Des., 2008, pp. 97-110, vol. 72.
Llambi et al., "A unified model of mammalian BCL-2 protein family interactions at the mitochondria", Mol Cell., Nov. 18, 2011, pp. 517-531 vol. 44, No. 4.
Mesri et al., "Heparin-binding Transforming Growth Fact a-Pseudomonas Exotoxin A", J. of Biochem. Chem., Mar. 5, 1993, pp. 4853-4862, vol. 268, No. 7.
Morris et al., "A Peptide Carrier for the Delivery of Biologically Active Proteins into Mammalian Cells", Nature Biotechnology, 2001, pp. 1173-1176, vol. 19.
Muller et al., "Protein Fusions to Coiled-Coil Domains", Methods in Enzymology, 2000, pp. 261-282, vol. 328.
Murakami et al., "The role of CXCR3 and CXCR4 in colorectal cancer metastasis", Int. J. Cancer, 2013, pp. 276-287, vol. 132.
Ogawa et al., "A Cytotoxic Ribonuclease Targeting Specific Transfer RNA Anticodons", Science, Mar. 26, 1999, pp. 2097-2100, vol. 283.

Pack et al., "Miniantibodies: Use of Amphipathic Helices to Produce Functional, Flexibly Linked Dimeric Fv Fragments with High Avidity in *Escherichia coli*", American Chemical Society, 1992, pp. 1579-1584, vol. 31, No. 6.
Pastan et al., "Recombinant Toxins as Novel Therapeutic Agents", Annu. Rev. Biochem., 1992, pp. 331-354, vol. 61.
Pesarrodona et al., "Intracellular Targeting of CD44 Cells with Self-Assembling, Protein Only Nanoparticles", International Journal of Pharmaceutics, 2014, pp. 286-295, vol. 473.
Routier et al., "Synthesis, DNA Binding, and Cleaving Properties of an Ellipticine-SalenCopper Conjugate", Bioconjugate Chem., 1997, pp. 789-792, vol. 8.
Rueda et al., "Bottom-Up Instructive Quality Control in the Biofabrication of Smart Protein Materials", Advanced Materials, 2015, pp. 7816-7822, vol. 22.
Sandvig et al., "Endocytosis, Intracellular Transport, and Cytotoxic Action of Shiga Toxin and Ricin", Physiological Reviews, 1996, pp. 949-966, vol. 76.
Schmidt et al., "Arginine-Rich Cell-Penetrating Peptides", FEBS Letters, 2010, pp. 1806-1813, vol. 584.
Serna et al., "Rational Engineering of Single-Chain Polypeptides into Protein-Only BBB-Targeted Nanoparticles", Nanomedicine: NBM, 2016, pp. 1241-1251, vol. 12.
Shaner et al., "A Guide to Choosing Fluorescent Proteins", Nature Methods, 2005, pp. 905-909, vol. 2, No. 12.
Shapira et al., "Toxin-Based Therapeutic Approaches", Toxins, 2010, pp. 2519-2583, vol. 2.
Skibo et al., "Structure-Activity Studies of Benzimidazol-Based DNA-Cleaving Agents. Comparison of Benzimidazole, Pyrrolobenzimidazole, and Tetrahydropyridobenzimidazole Analogues", J. Med. Chem., 1994, pp. 78-92, vol. 37.
Skinner et al., "Inhibition of prokaryotic translation by the Shiga toxin enzymatic subunit", Microbial Pathogenesis, 1998, pp. 117-122, vol. 24.
Smarda, et al., "Colicins—Exocellular Lethal Proteins of *Escherichia coli*", Folia Microbiol., 1998, pp. 563-582, vol. 43, No. 6.
Stirpe et al., "Ribosome-Inactivating Proteins from Plants: Present Status and Future Prospects", Biotechnology, 1992, pp. 405-412, vol. 10.
Tamamura et al., "Synthesis of potent CXCR4 inhibitors possessing low cytotoxicity and improved biostability based on T140 derivatives" Org. Biomol. Chem., 2003, pp. 3656-3662, vol. 1.
Taylor, "The Classification of Amino Acid Conservation", J. Theor. Biol., 1986, pp. 205-218, vol. 119.
Unno et al., "Structure-Activity Relationships of Cyclic Enediynes Related to Dynemicin A—I. Synthesis and Antitumor Activity of 9-Acetoxy Enediynes Equipped with Aryl Carbamate Moieties", Bioorganic and Medicinal Chemistry, 1997, pp. 883-901, vol. 5, No. 5.
Unno et al., "Structure-Activity Relationships of Cyclic Enediynes Related to Dynemicin A—II. Synthesis and Antitumor Activity of 9- and 12-Substituted Enediynes Equipped with Aryl Carbamate Moieties", Bioorganic and Medicinal Chemistry, 1997, pp. 903-919, vol. 5, No. 5.
Unno et al., "Synthesis and Biological Evaluation of Novel Cyclic Enediyne Compounds Related to Dynemicin A as Antitumor Agents", Chem. Pharm. Bull., 1997, pp. 125-133, vol. 45.
Unzueta et al., "Non-Amyloidogenic Peptide Tags for the Regulatable Self-Assembling of Protein-Only Nanoparticles", Biomaterials, 2012, pp. 8714-8722, vol. 33.
Van Dorpe, et al., "Brainpeps: the blood-brain barrier peptide database", Brain Struct Funct, 2012, pp. 687-718, vol. 217.
Wang et al., "The influence of lentivirus-mediated CXCR4 RNA interference on hepatic metastasis of colorectal cancer", Int. J. of Oncology, 2014, pp. 1861-1869, vol. 44.
Woodman et al., "Design and Validation of a Neutral Protein Scaffold for the Presentation of Peptide Aptamers", J. Mol. Biol., 2005, pp. 1118-1133, vol. 352.
Wool et al., "Ribotoxin recognition of ribosomal RNA and a proposal for the mechanism of translocation", Trends Biochem. Sci., Jul. 1992, pp. 266-269, vol. 17.

(56) References Cited

OTHER PUBLICATIONS

Xu et al., "DNA Damage Produced by Enediynes in the Human Phosphoglycerate Kinase Gene in Vivo: esperamicin A1 as a Nucleosome Footprinting Agent", Biochemistry, 1998, pp. 1890-1897, vol. 37.
Xu et al., "Formulating Tumor-Homing Peptides as Regular Nanoparticles Enhances Receptor-Mediated Cell Penetrability", Materials Letters, 2015, pp. 140-143, vol. 154.
Yandek et al., "Mechanism of the Cell-Penetrating Peptide Transportan 10 Permeation of Lipid Bilayers", Biophysical Journal, 2007, pp. 2434-2444, vol. 92.
Zhang et al., "CD133 CXCR4 colon cancer cells exhibit metastatic potential and predict poor prognosis of patients", BMC Medicine, 2012, p. 10, vol. 85.
Berendsen, "A Glimpse of the Holy Grail?", Science, Oct. 23, 1998, pp. 642-643, vol. 282.
Bradley et al., "Limits of Cooperativity in a Structurally Modular Protein: Response of the Notch Ankyrin Domain to Analogous Alanine Substitutions in Each Repeat", Journal of Molecular Biology, 2002, pp. 373-386, vol. 324.
Chen et al., "Fusion Protein Linkers: Property, Design and Functionality", Advanced Drug Delivery Reviews, Oct. 15, 2013, pp. 1357-1369, vol. 65, No. 10.
Céspedes et al., "Selective Depletion of Metastatic Stem Cells as Therapy for Human Colorectal Cancer", EMBO Molecular Medicine, 2018, pp. 1-22, vol. 10, No. 10.
Destouches et al., "Suppression of Tumor Growth and Angiogenesis by a Specific Antagonist of the Cell-Surface Expressed Nucleolin", PLoS ONE, Jun. 2008, pp. 1-12, vol. 3, No. 6.
Driessen et al., "Development of Peptide-Targeted Lipoplexes to CXCR4-Expressing Rat Glioma Cells and Rat Proliferating Endothelial Cells", Mar. 2008, pp. 516-524, vol. 16, No. 3.
Egorova et al., "Chemokine-Derived Peptides as Carriers for Gene Delivery to CXCR4 Expressing Cells", The Journal of Gene Medicine, Jun. 2009, pp. 772-781, vol. 11.
Hanaoka et al., "Development of a In-Labeled Peptide Derivative Targeting a Chemokine Receptor, CXCR4, for Imaging Tumors", Nuclear Medicine and Biology, 2006, pp. 489-494, vol. 33.
Kaplan et al., "Protection of the Furin Cleavage Site in Low-Toxicity Immunotoxins Based on Pseudomonas Exotoxin A", Toxins, 2016, 14 pages, vol. 8, No. 217.
Karjoo et al., "Progress and Problems with the Use of Suicide Genes for Targeted Cancer Therapy", Advanced Drug Delivery Reviews, Apr. 1, 2016, pp. 1-38, vol. 99.
Le Bon et al., "AMD3100 Conjugates as Components of Targeted Nonviral Gene Delivery Systems: Synthesis and in Vitro Transfection Efficiency of CXCR4-Expressing Cells", Bioconjugate Chemistry, 2004, pp. 413-423, vol. 15.
Murakami et al., "Inhibitory Mechanism of the CXCR4 Antagonist T22 Against Human Immunodeficiency Virus Type 1 Infection", Journal of Virology, Sep. 1999, pp. 7489-7496, vol. 73, No. 9.
Pallarès et al., "A Multivalent Ara-C-Prodrug Nanoconjugate Achieves Selective Ablation of Leukemic Cells in an Acute Myeloid Leukemia Mouse Model", Biomaterials, 2022, pp. 1-14, vol. 280, No. 121258.
Pallarès et al., "An Auristatin Nanoconjugate Targeting CXCR4+ Leukemic Cells Blocks Acute Myeloid Leukemia Dissemination", Journal of Hematology & Oncology, 2020, pp. 1-19, vol. 13, No. 36.
Reyes-Reyes et al., "Cell-Surface Nucleolin is a Signal Transducing P-Selectin Binding Protein for Human Colon Carcinoma Cells", Experimental Cell Research, 2008, pp. 2212-2223, vol. 314.
Richard et al., "Cell-Penetrating Peptides", The Journal of Biological Chemistry, Jan. 3, 2003, pp. 585-590, vol. 278, No. 1.
Roberts, "Non-Native Protein Aggregation Kinetics", Biotechnology and Bioengineering, Dec. 1, 2007, pp. 927-938, vol. 98, No. 5.
Rudinger, "Characteristics of the Amino Acids as Components of a Peptide Hormone Sequence", Peptide Hormones, 1976, 7 pages.
Schinzel et al., "The Phosphate Recognition Site of *Escherichia coli* Maltodextrin Phosphorylase", Elsevier Science Publishers B.V., Jul. 1991, pp. 125-128, vol. 286, No. 1.2.

Senbanjo et al., "CD44: A Multifunctional Cell Surface Adhesion Receptor is a Regulator of Progression and Metastasis of Cancer Cells", Frontiers in Cell and Developmental Biology, Mar. 2017, pp. 1-6, vol. 5, No. 18.
Serna et al., "Engineering Non-Antibody Human Proteins as Efficient Scaffolds for Selective, Receptor-Targeted Drug Delivery", Journal of Controlled Release, 2022, pp. 277-287, vol. 343.
Tamamura et al., "Synthesis and Evaluation of Bifunctional Anti-HIV Agents Based on Specific CXCR4 Antagonists-AZT Conjugation", Bioorganic & Medicinal Chemistry, 2001, pp. 2179-2187, vol. 9.
Unzueta et al., "Engineering Tumor Cell Targeting in Nanoscale Amyloidal Materials", Nanotechnology, 2017, pp. 1-10, vol. 28.
Unzueta et al., "Intracellular CXCR4+ Cell Targeting with T22-Empowered Protein-Only Nanoparticles", International Journal of Nanomedicine, 2012, pp. 4533-4544, vol. 7.
Volta-Duran et al., "Design and Engineering of Tumor-Targeted, Dual-Acting Cytotoxic Nanoparticles", Acta Biomaterialia, 2021, pp. 312-322, vol. 119.
Xu et al., "Targeting Low-Density Lipoprotein Receptors with Protein-Only Nanoparticles", Journal of Nanoparticle Research, Mar. 2015, 15 pages, vol. 17, No. 150.
Yandek et al., "Mechanism of Cell-Penetrating Peptide Transportan 10 Permeation of Lipid Bilayers", Biophysical Journal, Apr. 2007, pp. 2434-2444, vol. 92.
Zhang et al., "Cell-Penetrating and Endoplasmic Reticulum-Locating TAT-IL-24-KDEL Fusion Protein Induces Tumor Apoptosis", J. Cell. Physiol., 2016, pp. 84-93, vol. 231.
Zhang et al., "PUMA Promotes Bax Translocation by Both Directly Interacting with Bax and by Competitive Binding to Bcl-XL During UV-Induced Apoptosis", Molecular Biology of the Cell, Jul. 1, 2009, pp. 3077-3087, vol. 20.
Álamo et al., "Rational Engineering of a Human GFP-like Protein Scaffold for Humanized Targeted Nanomedicines", Acta Biomaterialia, 2021, pp. 211-222, vol. 130.
García-Fruitós et al., "Aggregation as Bacterial Inclusion Bodies Does Not Imply Inactivation of Enzymes and Fluorescent Proteins", Microbial Cell Factories, 2005, pp. 1-6, vol. 4, No. 27.
González-Montalban et al., "Comparative analysis of *E. coli* inclusion bodies and thermal protein aggregates", Microbial Cell Factories, 2006, pp. 1-2.
Díaz et al., "Selective CXCR4+ Cancer Cell Targeting and Potent Antineoplastic Effect by a Nanostructured Version of Recombinant Ricin", Small, 2018, 12 pages, No. 1800665.
Falgas et al., "A CXCR4-targeted nanocarrier achieves highly selective tumor uptake in diffuse large B-cell lymphoma mouse models", Haematologica, 2020, pp. 741-753, vol. 105, No. 3.
Falgas et al., "A diphtheria toxin-based nanoparticle achieves specific cytotoxic effect on CXCR4+ lymphoma cells without toxicity in immunocompromised and immunocompetent mice", Biomedicine & Pharmacotherapy, 2022, 12 pages, vol. 150, No. 112940.
Falgàs et al., "Selective delivery of T22-PE24-H6 to CXCR4 diffuse large B-cell lymphoma cells leads to wide therapeutic index in a disseminated mouse model", Theranostics, 2020, pp. 5169-5180, vol. 10, No. 12.
López-Laguna et al., "Assembly of histidine-rich protein materials controlled through divalent cations", Acta Biomaterialia, 2019, pp. 257-264, vol. 83.
López-Laguna et al., "Nanostructure Empowers Active Tumor Targeting in Ligand-Based Molecular Delivery", Particle & Particle Systems Characterization, 2019, 10 pages, No. 1900304.
Núñez et al., "T22-PE24-H6 Nanotoxin Selectively Kills CXCR4-High Expressing AML Patient Cells In Vitro and Potently Blocks Dissemination In Vivo", Pharmaceutics, 2023, 17 pages, vol. 15, No. 727.
Pallares et al., "Antineoplastic effect of a diphtheria toxin-based nanoparticle targeting acute myeloid leukemia cells overexpressing CXCR4", Journal of Controlled Release, 2021, pp. 117-129, vol. 335.
Sala et al., "GSDMD-dependent pyroptotic induction by a multivalent CXCR4-targeted nanotoxin blocks colorectal cancer metastases", Drug Delivery, 2022, pp. 1384-1397, vol. 29, No. 1.

(56) References Cited

OTHER PUBLICATIONS

Shuqing et al., "Precision Medicine", 2016, 3 pages, Tianjin Science and Technology Press.

Jiangang et al., "Modern Non-Surgical Treatment for Malignant Tumors of Bone and Soft tissue", 2008, 3 pages, Scientific and Technical Documentation Press.

* cited by examiner a b

C

D

A b

C

D

A b c d b

Leukos & Platelets pellets c

SEQUENCE LISTING

<160> NUMBER OF SEQ ID NOS: 52

<210> SEQ ID NO 1
<211> LENGTH: 9
<212> TYPE: PRT
<213> ORGANISM: Artificial Sequence
<220> FEATURE:
<223> OTHER INFORMATION: Polycationic peptide

<400> SEQUENCE: 1

Arg Arg Arg Arg Arg Arg Arg Arg Arg
1               5

<210> SEQ ID NO 2
<211> LENGTH: 9
<212> TYPE: PRT
<213> ORGANISM: Artificial Sequence
<220> FEATURE:
<223> OTHER INFORMATION: Polycationic peptide

<400> SEQUENCE: 2

Arg Arg Arg Gly Arg Gly Arg Arg Arg
1               5

<210> SEQ ID NO 3
<211> LENGTH: 9
<212> TYPE: PRT
<213> ORGANISM: Artificial Sequence
<220> FEATURE:
<223> OTHER INFORMATION: Polycationic peptide

<400> SEQUENCE: 3

Arg Ala Arg Gly Arg Gly Arg Arg Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Polycationic peptide

<400> SEQUENCE: 4

Arg Ala Arg Gly Arg Gly Gly Gly Ala
1               5

<210> SEQ ID NO 5
<211> LENGTH: 18
<212> TYPE: PRT
<213> ORGANISM: Artificial Sequence
<220> FEATURE:
<223> OTHER INFORMATION: T22 peptide

<400> SEQUENCE: 5

Arg Arg Trp Cys Tyr Arg Lys Cys Tyr Lys Gly Tyr Cys Tyr Arg Lys
1               5                   10                  15

Cys Arg

<210> SEQ ID NO 6
<211> LENGTH: 21
<212> TYPE: PRT
<213> ORGANISM: Artificial Sequence
<220> FEATURE:
<223> OTHER INFORMATION: V1 peptide

<400> SEQUENCE: 6

```
Leu Gly Ala Ser Trp His Arg Pro Asp Lys Cys Cys Leu Gly Tyr Gln
 1               5                  10                  15

Lys Arg Pro Leu Pro
            20

<210> SEQ ID NO 7
<211> LENGTH: 67
<212> TYPE: PRT
<213> ORGANISM: Artificial Sequence
<220> FEATURE:
<223> OTHER INFORMATION: CXCL12 peptide

<400> SEQUENCE: 7

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
     50                  55                  60

Ala Leu Asn
 65

<210> SEQ ID NO 8
<211> LENGTH: 68
<212> TYPE: PRT
<213> ORGANISM: Artificial Sequence
<220> FEATURE:
<223> OTHER INFORMATION: vCCL2 peptide

<400> SEQUENCE: 8

Leu Gly Ala Ser Trp His Arg Pro Asp Lys Cys Cys Leu Gly Tyr Gln
 1               5                  10                  15

Lys Arg Pro Leu Pro Gln Val Leu Leu Ser Ser Trp Tyr Pro Thr Ser
                20                  25                  30

Gln Leu Cys Ser Lys Pro Gly Val Ile Phe Leu Thr Lys Arg Gly Arg
            35                  40                  45

Gln Val Cys Ala Asp Lys Asp Trp Val Lys Lys Leu Met Gln Gln Leu
     50                  55                  60

Pro Val Thr Ala
 65

<210> SEQ ID NO 9
<211> LENGTH: 14
<212> TYPE: PRT
<213> ORGANISM: Artificial Sequence
<220> FEATURE:
<223> OTHER INFORMATION: T140 peptide
<220> FEATURE:
<221> NAME/KEY: MISC_FEATURE
<222> LOCATION: (3)..(3)
<223> OTHER INFORMATION: Xaa is L-3-(2-naphthyl)alanine
<220> FEATURE:
<221> NAME/KEY: MISC_FEATURE
<222> LOCATION: (8)..(8)
<223> OTHER INFORMATION: Xaa is D-Lys
<220> FEATURE:
<221> NAME/KEY: MISC_FEATURE
<222> LOCATION: (12)..(12)
<223> OTHER INFORMATION: Xaa is L-Citrulline

<400> SEQUENCE: 9

Arg Arg Xaa Cys Tyr Arg Lys Xaa Pro Tyr Arg Xaa Cys Arg
```

<210> SEQ ID NO 10
<211> LENGTH: 14
<212> TYPE: PRT
<213> ORGANISM: Artificial Sequence
<220> FEATURE:
<223> OTHER INFORMATION: TN14003 peptide
<220> FEATURE:
<221> NAME/KEY: MISC_FEATURE
<222> LOCATION: (3)..(3)
<223> OTHER INFORMATION: Xaa is L-3-(2-naphthyl)alanine
<220> FEATURE:
<221> NAME/KEY: MISC_FEATURE
<222> LOCATION: (6)..(6)
<223> OTHER INFORMATION: Xaa is L-Citrulline
<220> FEATURE:
<221> NAME/KEY: MISC_FEATURE
<222> LOCATION: (8)..(8)
<223> OTHER INFORMATION: Xaa is D-Lys
<220> FEATURE:
<221> NAME/KEY: MISC_FEATURE
<222> LOCATION: (12)..(12)
<223> OTHER INFORMATION: Xaa is L-Citrulline

<400> SEQUENCE: 10

Arg Arg Xaa Cys Tyr Xaa Lys Xaa Pro Tyr Arg Xaa Cys Arg
1               5                   10

<210> SEQ ID NO 11
<211> LENGTH: 14
<212> TYPE: PRT
<213> ORGANISM: Artificial Sequence
<220> FEATURE:
<223> OTHER INFORMATION: TC 14012 peptide
<220> FEATURE:
<221> NAME/KEY: MISC_FEATURE
<222> LOCATION: (3)..(3)
<223> OTHER INFORMATION: Xaa is L-3-(2-naphthyl)alanine
<220> FEATURE:
<221> NAME/KEY: MISC_FEATURE
<222> LOCATION: (8)..(8)
<223> OTHER INFORMATION: Xaa is D-Citrulline
<220> FEATURE:
<221> NAME/KEY: MISC_FEATURE
<222> LOCATION: (12)..(12)
<223> OTHER INFORMATION: Xaa is L-Citrulline

<400> SEQUENCE: 11

Arg Arg Xaa Cys Tyr Glu Lys Xaa Pro Tyr Arg Xaa Cys Arg
1               5                   10

<210> SEQ ID NO 12
<211> LENGTH: 14
<212> TYPE: PRT
<213> ORGANISM: Artificial Sequence
<220> FEATURE:
<223> OTHER INFORMATION: TE14011 peptide
<220> FEATURE:
<221> NAME/KEY: MISC_FEATURE
<222> LOCATION: (3)..(3)
<223> OTHER INFORMATION: Xaa  is L-3-(2-naphthyl)alanine
<220> FEATURE:
<221> NAME/KEY: MISC_FEATURE
<222> LOCATION: (6)..(6)
<223> OTHER INFORMATION: Xaa is  L-Citrulline
<220> FEATURE:
<221> NAME/KEY: MISC_FEATURE
<222> LOCATION: (8)..(8)
<223> OTHER INFORMATION: Xaa is D-Glutamic acid
<220> FEATURE:
<221> NAME/KEY: MISC_FEATURE
<222> LOCATION: (12)..(12)
<223> OTHER INFORMATION: Xaa is  L-Citrulline

```
<400> SEQUENCE: 12

Arg Arg Xaa Cys Tyr Xaa Lys Xaa Pro Tyr Arg Xaa Cys Arg
1               5                   10

<210> SEQ ID NO 13
<211> LENGTH: 14
<212> TYPE: PRT
<213> ORGANISM: Artificial Sequence
<220> FEATURE:
<223> OTHER INFORMATION: TZ14011 peptide
<220> FEATURE:
<221> NAME/KEY: MISC_FEATURE
<222> LOCATION: (3)..(3)
<223> OTHER INFORMATION: Xaa is L-3-(2)-naphthyl)alanine
<220> FEATURE:
<221> NAME/KEY: MISC_FEATURE
<222> LOCATION: (6)..(6)
<223> OTHER INFORMATION: Xaa is L-Citrulline
<220> FEATURE:
<221> NAME/KEY: MISC_FEATURE
<222> LOCATION: (8)..(8)
<223> OTHER INFORMATION: Xaa is D-Lysine
<220> FEATURE:
<221> NAME/KEY: MISC_FEATURE
<222> LOCATION: (12)..(12)
<223> OTHER INFORMATION: Xaa is L-Citrulline

<400> SEQUENCE: 13

Arg Arg Xaa Cys Tyr Xaa Lys Xaa Pro Tyr Arg Xaa Cys Arg
1               5                   10

<210> SEQ ID NO 14
<211> LENGTH: 20
<212> TYPE: PRT
<213> ORGANISM: Artificial Sequence
<220> FEATURE:
<223> OTHER INFORMATION: GW-H1 peptide

<400> SEQUENCE: 14

Gly Tyr Asn Tyr Ala Lys Lys Leu Ala Asn Leu Ala Lys Lys Phe Ala
1               5                   10                  15

Asn Ala Leu Trp
            20

<210> SEQ ID NO 15
<211> LENGTH: 13
<212> TYPE: PRT
<213> ORGANISM: Artificial Sequence
<220> FEATURE:
<223> OTHER INFORMATION: A5G27

<400> SEQUENCE: 15

Arg Leu Val Ser Tyr Asn Gly Ile Ile Phe Phe Leu Lys
1               5                   10

<210> SEQ ID NO 16
<211> LENGTH: 69
<212> TYPE: PRT
<213> ORGANISM: Artificial Sequence
<220> FEATURE:
<223> OTHER INFORMATION: FNI/II/V

<400> SEQUENCE: 16

Trp Gln Pro Pro Arg Ala Arg Ile Thr Gly Tyr Ile Ile Lys Tyr Glu
1               5                   10                  15

Lys Pro Gly Ser Pro Pro Arg Glu Val Val Pro Arg Pro Arg Pro Gly
            20                  25                  30
```

```
Val Thr Glu Ala Thr Ile Thr Gly Leu Glu Pro Gly Thr Glu Tyr Thr
            35                  40                  45

Ile Tyr Val Ile Ala Leu Lys Asn Asn Gln Lys Ser Glu Pro Leu Ile
    50                  55                  60

Gly Arg Lys Lys Thr
65

<210> SEQ ID NO 17
<211> LENGTH: 18
<212> TYPE: PRT
<213> ORGANISM: Artificial Sequence
<220> FEATURE:
<223> OTHER INFORMATION: Seq-1-7 peptide

<400> SEQUENCE: 17

Lys Tyr Leu Ala Tyr Pro Asp Ser Val His Ile Trp Arg Lys Arg Lys
1               5                  10                  15

Arg Lys

<210> SEQ ID NO 18
<211> LENGTH: 19
<212> TYPE: PRT
<213> ORGANISM: Artificial Sequence
<220> FEATURE:
<223> OTHER INFORMATION: Seq-1-8 peptide

<400> SEQUENCE: 18

Lys Tyr Leu Ala Tyr Pro Asp Ser Val His Ile Trp Arg Lys Arg Lys
1               5                  10                  15

Arg Lys Arg

<210> SEQ ID NO 19
<211> LENGTH: 22
<212> TYPE: PRT
<213> ORGANISM: Artificial Sequence
<220> FEATURE:
<223> OTHER INFORMATION: Angiopep-2-7 peptide

<400> SEQUENCE: 19

Thr Phe Phe Tyr Gly Gly Ser Arg Gly Lys Arg Asn Asn Phe Lys Thr
1               5                  10                  15

Glu Glu Tyr Arg Lys Arg
            20

<210> SEQ ID NO 20
<211> LENGTH: 31
<212> TYPE: PRT
<213> ORGANISM: Artificial Sequence
<220> FEATURE:
<223> OTHER INFORMATION: Nucleolin binding peptide

<400> SEQUENCE: 20

Lys Asp Glu Pro Gln Arg Arg Ser Ala Arg Leu Ser Ala Lys Pro Ala
1               5                  10                  15

Pro Pro Lys Pro Glu Pro Lys Pro Lys Lys Ala Pro Ala Lys Lys
            20                  25                  30

<210> SEQ ID NO 21
<211> LENGTH: 39
<212> TYPE: PRT
<213> ORGANISM: Artificial Sequence
<220> FEATURE:
<223> OTHER INFORMATION: Nucleolin binding peptide
```

```
<400> SEQUENCE: 21

Lys Asp Glu Pro Gln Arg Arg Ser Ala Arg Leu Ser Ala Lys Pro Ala
1               5                   10                  15

Pro Pro Lys Pro Glu Pro Lys Pro Lys Ala Pro Lys Lys Arg
            20                  25                  30

Lys Arg Lys Arg Lys Arg Lys
        35

<210> SEQ ID NO 22
<211> LENGTH: 14
<212> TYPE: PRT
<213> ORGANISM: Artificial Sequence
<220> FEATURE:
<223> OTHER INFORMATION: Linker/spacer

<400> SEQUENCE: 22

Ser Gly Gly Thr Ser Gly Ser Thr Ser Gly Thr Gly Ser Thr
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Linker/spacer

<400> SEQUENCE: 23

Ala Gly Ser Ser Thr Gly Ser Ser Thr Gly Pro Gly Ser Thr Thr
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Linker/spacer

<400> SEQUENCE: 24

Gly Gly Ser Gly Gly Ala Pro
1               5

<210> SEQ ID NO 25
<211> LENGTH: 8
<212> TYPE: PRT
<213> ORGANISM: Artificial Sequence
<220> FEATURE:
<223> OTHER INFORMATION: Linker/spacer

<400> SEQUENCE: 25

Gly Gly Gly Val Glu Gly Gly Gly
1               5

<210> SEQ ID NO 26
<211> LENGTH: 10
<212> TYPE: PRT
<213> ORGANISM: Artificial Sequence
<220> FEATURE:
<223> OTHER INFORMATION: 10 amino acid residues of the upper hinge
      region of murine IgG3

<400> SEQUENCE: 26

Pro Lys Pro Ser Thr Pro Pro Gly Ser Ser
1               5                   10
```

```
<210> SEQ ID NO 27
<211> LENGTH: 11
<212> TYPE: PRT
<213> ORGANISM: Artificial Sequence
<220> FEATURE:
<223> OTHER INFORMATION: Linker/spacer

<400> SEQUENCE: 27

Ala Pro Ala Glu Thr Lys Ala Glu Pro Met Thr
1               5                   10

<210> SEQ ID NO 28
<211> LENGTH: 5
<212> TYPE: PRT
<213> ORGANISM: Artificial Sequence
<220> FEATURE:
<223> OTHER INFORMATION: Cleavage site

<400> SEQUENCE: 28

Asp Asp Asp Asp Lys
1               5

<210> SEQ ID NO 29
<211> LENGTH: 5
<212> TYPE: PRT
<213> ORGANISM: Artificial Sequence
<220> FEATURE:
<223> OTHER INFORMATION: Cleavage site

<400> SEQUENCE: 29

Ile Glu Asp Gly Arg
1               5

<210> SEQ ID NO 30
<211> LENGTH: 6
<212> TYPE: PRT
<213> ORGANISM: Artificial Sequence
<220> FEATURE:
<223> OTHER INFORMATION: Cleavage site

<400> SEQUENCE: 30

Leu Val Pro Arg Gly Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Cleavage site

<400> SEQUENCE: 31

Glu Asn Leu Tyr Phe Gln Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Cleavage site

<400> SEQUENCE: 32

Leu Glu Val Leu Phe Gln Gly Pro
1               5

<210> SEQ ID NO 33
```

```
<211> LENGTH: 7
<212> TYPE: PRT
<213> ORGANISM: Artificial Sequence
<220> FEATURE:
<223> OTHER INFORMATION: linker

<400> SEQUENCE: 33

Gly Gly Ser Ser Arg Ser Ser
1               5

<210> SEQ ID NO 34
<211> LENGTH: 5
<212> TYPE: PRT
<213> ORGANISM: Artificial Sequence
<220> FEATURE:
<223> OTHER INFORMATION: linker

<400> SEQUENCE: 34

Gly Gly Gly Asn Ser
1               5

<210> SEQ ID NO 35
<211> LENGTH: 238
<212> TYPE: PRT
<213> ORGANISM: Aequorea victoria

<400> SEQUENCE: 35

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 36
```

<211> LENGTH: 609
<212> TYPE: PRT
<213> ORGANISM: Homo sapiens

<400> SEQUENCE: 36

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
```

```
                385                 390                 395                 400
Phe Lys Pro Leu Val Glu Glu Pro Gln Asn Leu Ile Lys Gln Asn Cys
                    405                 410                 415
Glu Leu Phe Glu Gln Leu Gly Glu Tyr Lys Phe Gln Asn Ala Leu Leu
            420                 425                 430
Val Arg Tyr Thr Lys Lys Val Pro Gln Val Ser Thr Pro Thr Leu Val
        435                 440                 445
Glu Val Ser Arg Asn Leu Gly Lys Val Gly Ser Lys Cys Cys Lys His
    450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
            500                 505                 510
Ser Ala Leu Glu Val Asp Glu Thr Tyr Val Pro Lys Glu Phe Asn Ala
        515                 520                 525
Glu Thr Phe Thr Phe His Ala Asp Ile Cys Thr Leu Ser Glu Lys Glu
    530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
            580                 585                 590
Ala Glu Glu Gly Lys Lys Leu Val Ala Ala Ser Gln Ala Ala Leu Gly
        595                 600                 605
Leu

<210> SEQ ID NO 37
<211> LENGTH: 1247
<212> TYPE: PRT
<213> ORGANISM: Homo sapiens

<400> SEQUENCE: 37

Met Leu Ala Ser Ser Arg Ile Arg Ala Ala Trp Thr Arg Ala Leu
1               5                   10                  15
Leu Leu Pro Leu Leu Leu Ala Gly Pro Val Gly Cys Leu Ser Arg Gln
                20                  25                  30
Glu Leu Phe Pro Phe Gly Pro Gly Gln Gly Asp Leu Glu Leu Glu Asp
            35                  40                  45
Gly Asp Asp Phe Val Ser Pro Ala Leu Glu Leu Ser Gly Ala Leu Arg
        50                  55                  60
Phe Tyr Asp Arg Ser Asp Ile Asp Ala Val Tyr Val Thr Thr Asn Gly
65                  70                  75                  80
Ile Ile Ala Thr Ser Glu Pro Pro Ala Lys Glu Ser His Pro Gly Leu
                85                  90                  95
Phe Pro Pro Thr Phe Gly Ala Val Ala Pro Phe Leu Ala Asp Leu Asp
            100                 105                 110
Thr Thr Asp Gly Leu Gly Lys Val Tyr Tyr Arg Glu Asp Leu Ser Pro
        115                 120                 125
Ser Ile Thr Gln Arg Ala Ala Glu Cys Val His Arg Gly Phe Pro Glu
    130                 135                 140
Ile Ser Phe Gln Pro Ser Ser Ala Val Val Val Thr Trp Glu Ser Val
```

```
            145                 150                 155                 160
Ala Pro Tyr Gln Gly Pro Ser Arg Asp Pro Asp Gln Lys Gly Lys Arg
                165                 170                 175
Asn Thr Phe Gln Ala Val Leu Ala Ser Ser Asp Ser Ser Ser Tyr Ala
                180                 185                 190
Ile Phe Leu Tyr Pro Glu Asp Gly Leu Gln Phe His Thr Thr Phe Ser
                195                 200                 205
Lys Lys Glu Asn Asn Gln Val Pro Ala Val Val Ala Phe Ser Gln Gly
    210                 215                 220
Ser Val Gly Phe Leu Trp Lys Ser Asn Gly Ala Tyr Asn Ile Phe Ala
225                 230                 235                 240
Asn Asp Arg Glu Ser Val Glu Asn Leu Ala Lys Ser Ser Asn Ser Gly
                245                 250                 255
Gln Gln Gly Val Trp Val Phe Glu Ile Gly Ser Pro Ala Thr Thr Asn
                260                 265                 270
Gly Val Val Pro Ala Asp Val Ile Leu Gly Thr Glu Asp Gly Ala Glu
                275                 280                 285
Tyr Asp Asp Glu Asp Glu Asp Tyr Asp Leu Ala Thr Thr Arg Leu Gly
                290                 295                 300
Leu Glu Asp Val Gly Thr Thr Pro Phe Ser Tyr Lys Ala Leu Arg Arg
305                 310                 315                 320
Gly Gly Ala Asp Thr Tyr Ser Val Pro Ser Val Leu Ser Pro Arg Arg
                325                 330                 335
Ala Ala Thr Glu Arg Pro Leu Gly Pro Pro Thr Glu Arg Thr Arg Ser
                340                 345                 350
Phe Gln Leu Ala Val Glu Thr Phe His Gln His Pro Gln Val Ile
                355                 360                 365
Asp Val Asp Glu Val Glu Glu Thr Gly Val Val Phe Ser Tyr Asn Thr
                370                 375                 380
Asp Ser Arg Gln Thr Cys Ala Asn Asn Arg His Gln Cys Ser Val His
385                 390                 395                 400
Ala Glu Cys Arg Asp Tyr Ala Thr Gly Phe Cys Cys Ser Cys Val Ala
                405                 410                 415
Gly Tyr Thr Gly Asn Gly Arg Gln Cys Val Ala Glu Gly Ser Pro Gln
                420                 425                 430
Arg Val Asn Gly Lys Val Lys Gly Arg Ile Phe Val Gly Ser Ser Gln
                435                 440                 445
Val Pro Ile Val Phe Glu Asn Thr Asp Leu His Ser Tyr Val Val Met
    450                 455                 460
Asn His Gly Arg Ser Tyr Thr Ala Ile Ser Thr Ile Pro Glu Thr Val
465                 470                 475                 480
Gly Tyr Ser Leu Leu Pro Leu Ala Pro Val Gly Gly Ile Ile Gly Trp
                485                 490                 495
Met Phe Ala Val Glu Gln Asp Gly Phe Lys Asn Gly Phe Ser Ile Thr
                500                 505                 510
Gly Gly Glu Phe Thr Arg Gln Ala Glu Val Thr Phe Val Gly His Pro
                515                 520                 525
Gly Asn Leu Val Ile Lys Gln Arg Phe Ser Gly Ile Asp Glu His Gly
                530                 535                 540
His Leu Thr Ile Asp Thr Glu Leu Glu Gly Arg Val Pro Gln Ile Pro
545                 550                 555                 560
Phe Gly Ser Ser Val His Ile Glu Pro Tyr Thr Glu Leu Tyr His Tyr
                565                 570                 575
```

-continued

```
Ser Thr Ser Val Ile Thr Ser Ser Thr Arg Glu Tyr Thr Val Thr
            580             585             590
Glu Pro Glu Arg Asp Gly Ala Ser Pro Ser Arg Ile Tyr Thr Tyr Gln
        595             600             605
Trp Arg Gln Thr Ile Thr Phe Gln Glu Cys Val His Asp Asp Ser Arg
610             615             620
Pro Ala Leu Pro Ser Thr Gln Gln Leu Ser Val Asp Ser Val Phe Val
625             630             635             640
Leu Tyr Asn Gln Glu Glu Lys Ile Leu Arg Tyr Ala Leu Ser Asn Ser
            645             650             655
Ile Gly Pro Val Arg Glu Gly Ser Pro Asp Ala Leu Gln Asn Pro Cys
        660             665             670
Tyr Ile Gly Thr His Gly Cys Asp Thr Asn Ala Ala Cys Arg Pro Gly
    675             680             685
Pro Arg Thr Gln Phe Thr Cys Glu Cys Ser Ile Gly Phe Arg Gly Asp
690             695             700
Gly Arg Thr Cys Tyr Asp Ile Asp Glu Cys Ser Glu Gln Pro Ser Val
705             710             715             720
Cys Gly Ser His Thr Ile Cys Asn Asn His Pro Gly Thr Phe Arg Cys
            725             730             735
Glu Cys Val Glu Gly Tyr Gln Phe Ser Asp Glu Gly Thr Cys Val Ala
        740             745             750
Val Val Asp Gln Arg Pro Ile Asn Tyr Cys Glu Thr Gly Leu His Asn
    755             760             765
Cys Asp Ile Pro Gln Arg Ala Gln Cys Ile Tyr Thr Gly Gly Ser Ser
770             775             780
Tyr Thr Cys Ser Cys Leu Pro Gly Phe Ser Gly Asp Gly Gln Ala Cys
785             790             795             800
Gln Asp Val Asp Glu Cys Gln Pro Ser Arg Cys His Pro Asp Ala Phe
            805             810             815
Cys Tyr Asn Thr Pro Gly Ser Phe Thr Cys Gln Cys Lys Pro Gly Tyr
        820             825             830
Gln Gly Asp Gly Phe Arg Cys Val Pro Gly Glu Val Glu Lys Thr Arg
    835             840             845
Cys Gln His Glu Arg Glu His Ile Leu Gly Ala Ala Gly Ala Thr Asp
850             855             860
Pro Gln Arg Pro Ile Pro Pro Gly Leu Phe Val Pro Glu Cys Asp Ala
865             870             875             880
His Gly His Tyr Ala Pro Thr Gln Cys His Gly Ser Thr Gly Tyr Cys
            885             890             895
Trp Cys Val Asp Arg Asp Gly Arg Glu Val Glu Gly Thr Arg Thr Arg
        900             905             910
Pro Gly Met Thr Pro Pro Cys Leu Ser Thr Val Ala Pro Pro Ile His
    915             920             925
Gln Gly Pro Ala Val Pro Thr Ala Val Ile Pro Leu Pro Pro Gly Thr
930             935             940
His Leu Leu Phe Ala Gln Thr Gly Lys Ile Glu Arg Leu Pro Leu Glu
945             950             955             960
Gly Asn Thr Met Arg Lys Thr Glu Ala Lys Ala Phe Leu His Val Pro
            965             970             975
Ala Lys Val Ile Ile Gly Leu Ala Phe Asp Cys Val Asp Lys Met Val
        980             985             990
```

```
Tyr Trp Thr Asp Ile Thr Glu Pro  Ser Ile Gly Arg Ala  Ser Leu His
            995                 1000                 1005

Gly Gly Glu Pro Thr Thr Ile  Ile Arg Gln Asp Leu  Gly Ser Pro
    1010                 1015                 1020

Glu Gly Ile Ala Val Asp His  Leu Gly Arg Asn Ile  Phe Trp Thr
    1025                 1030                 1035

Asp Ser Asn Leu Asp Arg Ile  Glu Val Ala Lys Leu  Asp Gly Thr
    1040                 1045                 1050

Gln Arg Arg Val Leu Phe Glu  Thr Asp Leu Val Asn  Pro Arg Gly
    1055                 1060                 1065

Ile Val Thr Asp Ser Val Arg  Gly Asn Leu Tyr Trp  Thr Asp Trp
    1070                 1075                 1080

Asn Arg Asp Asn Pro Lys Ile  Glu Thr Ser Tyr Met  Asp Gly Thr
    1085                 1090                 1095

Asn Arg Arg Ile Leu Val Gln  Asp Asp Leu Gly Leu  Pro Asn Gly
    1100                 1105                 1110

Leu Thr Phe Asp Ala Phe Ser  Ser Gln Leu Cys Trp  Val Asp Ala
    1115                 1120                 1125

Gly Thr Asn Arg Ala Glu Cys  Leu Asn Pro Ser Gln  Pro Ser Arg
    1130                 1135                 1140

Arg Lys Ala Leu Glu Gly Leu  Gln Tyr Pro Phe Ala  Val Thr Ser
    1145                 1150                 1155

Tyr Gly Lys Asn Leu Tyr Phe  Thr Asp Trp Lys Met  Asn Ser Val
    1160                 1165                 1170

Val Ala Leu Asp Leu Ala Ile  Ser Lys Glu Thr Asp  Ala Phe Gln
    1175                 1180                 1185

Pro His Lys Gln Thr Arg Leu  Tyr Gly Ile Thr Thr  Ala Leu Ser
    1190                 1195                 1200

Gln Cys Pro Gln Gly His Asn  Tyr Cys Ser Val Asn  Asn Gly Gly
    1205                 1210                 1215

Cys Thr His Leu Cys Leu Ala  Thr Pro Gly Ser Arg  Thr Cys Arg
    1220                 1225                 1230

Cys Pro Asp Asn Thr Leu Gly  Val Asp Cys Ile Glu  Gln Lys
    1235                 1240                 1245

<210> SEQ ID NO 38
<211> LENGTH: 1375
<212> TYPE: PRT
<213> ORGANISM: Homo sapiens

<400> SEQUENCE: 38

Met Glu Gly Asp Arg Val Ala Gly Arg Pro Val Leu Ser Ser Leu Pro
1               5                   10                  15

Val Leu Leu Leu Leu Pro Leu Leu Met Leu Arg Ala Ala Ala Leu His
                20                  25                  30

Pro Asp Glu Leu Phe Pro His Gly Glu Ser Trp Gly Asp Gln Leu Leu
            35                  40                  45

Gln Glu Gly Asp Asp Glu Ser Ser Ala Val Val Lys Leu Ala Asn Pro
        50                  55                  60

Leu His Phe Tyr Glu Ala Arg Phe Ser Asn Leu Tyr Val Gly Thr Asn
65                  70                  75                  80

Gly Ile Ile Ser Thr Gln Asp Phe Pro Arg Glu Thr Gln Tyr Val Asp
                85                  90                  95

Tyr Asp Phe Pro Thr Asp Phe Pro Ala Ile Ala Pro Phe Leu Ala Asp
            100                 105                 110
```

```
Ile Asp Thr Ser His Gly Arg Gly Arg Val Leu Tyr Arg Glu Asp Thr
            115                 120                 125
Ser Pro Ala Val Leu Gly Leu Ala Ala Arg Tyr Val Arg Ala Gly Phe
130                 135                 140
Pro Arg Ser Ala Arg Phe Thr Pro Thr His Ala Phe Leu Ala Thr Trp
145                 150                 155                 160
Glu Gln Val Gly Ala Tyr Glu Val Lys Arg Gly Ala Leu Pro Ser
                165                 170                 175
Gly Glu Leu Asn Thr Phe Gln Ala Val Leu Ala Ser Asp Gly Ser Asp
            180                 185                 190
Ser Tyr Ala Leu Phe Leu Tyr Pro Ala Asn Gly Leu Gln Phe Leu Gly
            195                 200                 205
Thr Arg Pro Lys Glu Ser Tyr Asn Val Gln Leu Gln Leu Pro Ala Arg
            210                 215                 220
Val Gly Phe Cys Arg Gly Glu Ala Asp Asp Leu Lys Ser Glu Gly Pro
225                 230                 235                 240
Tyr Phe Ser Leu Thr Ser Thr Glu Gln Ser Val Lys Asn Leu Tyr Gln
            245                 250                 255
Leu Ser Asn Leu Gly Ile Pro Gly Val Trp Ala Phe His Ile Gly Ser
            260                 265                 270
Thr Ser Pro Leu Asp Asn Val Arg Pro Ala Ala Val Gly Asp Leu Ser
            275                 280                 285
Ala Ala His Ser Ser Val Pro Leu Gly Arg Ser Phe Ser His Ala Thr
            290                 295                 300
Ala Leu Glu Ser Asp Tyr Asn Glu Asp Asn Leu Asp Tyr Tyr Asp Val
305                 310                 315                 320
Asn Glu Glu Glu Ala Glu Tyr Leu Pro Gly Glu Pro Glu Glu Ala Leu
                325                 330                 335
Asn Gly His Ser Ser Ile Asp Val Ser Phe Gln Ser Lys Val Asp Thr
            340                 345                 350
Lys Pro Leu Glu Glu Ser Ser Thr Leu Asp Pro His Thr Lys Glu Gly
            355                 360                 365
Thr Ser Leu Gly Glu Val Gly Gly Pro Asp Leu Lys Gly Gln Val Glu
            370                 375                 380
Pro Trp Asp Glu Arg Glu Thr Arg Ser Pro Ala Pro Pro Glu Val Asp
385                 390                 395                 400
Arg Asp Ser Leu Ala Pro Ser Trp Glu Thr Pro Pro Tyr Pro Glu
                405                 410                 415
Asn Gly Ser Ile Gln Pro Tyr Pro Asp Gly Pro Val Pro Ser Glu
                420                 425                 430
Met Asp Val Pro Pro Ala His Pro Glu Glu Ile Val Leu Arg Ser
            435                 440                 445
Tyr Pro Ala Ser Gly His Thr Thr Pro Leu Ser Arg Gly Thr Tyr Glu
            450                 455                 460
Val Gly Leu Glu Asp Asn Ile Gly Ser Asn Thr Glu Val Phe Thr Tyr
465                 470                 475                 480
Asn Ala Ala Asn Lys Glu Thr Cys Glu His Asn His Arg Gln Cys Ser
                485                 490                 495
Arg His Ala Phe Cys Thr Asp Tyr Ala Thr Gly Phe Cys Cys His Cys
                500                 505                 510
Gln Ser Lys Phe Tyr Gly Asn Gly Lys His Cys Leu Pro Glu Gly Ala
            515                 520                 525
```

-continued

```
Pro His Arg Val Asn Gly Lys Val Ser Gly His Leu His Val Gly His
    530                 535                 540
Thr Pro Val His Phe Thr Asp Val Asp Leu His Ala Tyr Ile Val Gly
545                 550                 555                 560
Asn Asp Gly Arg Ala Tyr Thr Ala Ile Ser His Ile Pro Gln Pro Ala
                565                 570                 575
Ala Gln Ala Leu Leu Pro Leu Thr Pro Ile Gly Gly Leu Phe Gly Trp
            580                 585                 590
Leu Phe Ala Leu Glu Lys Pro Gly Ser Glu Asn Gly Phe Ser Leu Ala
        595                 600                 605
Gly Ala Ala Phe Thr His Asp Met Glu Val Thr Phe Tyr Pro Gly Glu
    610                 615                 620
Glu Thr Val Arg Ile Thr Gln Thr Ala Glu Gly Leu Asp Pro Glu Asn
625                 630                 635                 640
Tyr Leu Ser Ile Lys Thr Asn Ile Gln Gly Gln Val Pro Tyr Val Ser
                645                 650                 655
Ala Asn Phe Thr Ala His Ile Ser Pro Tyr Lys Glu Leu Tyr His Tyr
            660                 665                 670
Ser Asp Ser Thr Val Thr Ser Thr Ser Arg Asp Tyr Ser Leu Thr
        675                 680                 685
Phe Gly Ala Ile Asn Gln Thr Trp Ser Tyr Arg Ile His Gln Asn Ile
    690                 695                 700
Thr Tyr Gln Val Cys Arg His Ala Pro Arg His Pro Ser Phe Pro Thr
705                 710                 715                 720
Thr Gln Gln Leu Asn Val Asp Arg Val Phe Ala Leu Tyr Asn Asp Glu
                725                 730                 735
Glu Arg Val Leu Arg Phe Ala Val Thr Asn Gln Ile Gly Pro Val Lys
            740                 745                 750
Glu Asp Ser Asp Pro Thr Pro Gly Asn Pro Cys Tyr Asp Gly Ser His
        755                 760                 765
Met Cys Asp Thr Thr Ala Arg Cys His Pro Gly Thr Gly Val Asp Tyr
    770                 775                 780
Thr Cys Glu Cys Ala Ser Gly Tyr Gln Gly Asp Gly Arg Asn Cys Val
785                 790                 795                 800
Asp Glu Asn Glu Cys Ala Thr Gly Phe His Arg Cys Gly Pro Asn Ser
                805                 810                 815
Val Cys Ile Asn Leu Pro Gly Ser Tyr Arg Cys Glu Cys Arg Ser Gly
            820                 825                 830
Tyr Glu Phe Ala Asp Asp Arg His Thr Cys Ile Leu Ile Thr Pro Pro
        835                 840                 845
Ala Asn Pro Cys Glu Asp Gly Ser His Thr Cys Ala Pro Ala Gly Gln
    850                 855                 860
Ala Arg Cys Val His His Gly Gly Ser Thr Phe Ser Cys Ala Cys Leu
865                 870                 875                 880
Pro Gly Tyr Ala Gly Asp Gly His Gln Cys Thr Asp Val Asp Glu Cys
                885                 890                 895
Ser Glu Asn Arg Cys His Pro Ala Ala Thr Cys Tyr Asn Thr Pro Gly
            900                 905                 910
Ser Phe Ser Cys Arg Cys Gln Pro Gly Tyr Tyr Gly Asp Gly Phe Gln
        915                 920                 925
Cys Ile Pro Asp Ser Thr Ser Ser Leu Thr Pro Cys Glu Gln Gln Gln
    930                 935                 940
Arg His Ala Gln Ala Gln Tyr Ala Tyr Pro Gly Ala Arg Phe His Ile
```

```
                945                 950                 955                 960
         Pro Gln Cys Asp Glu Gln Gly Asn Phe Leu Pro Leu Gln Cys His Gly
                         965                 970                 975
         Ser Thr Gly Phe Cys Trp Cys Val Asp Pro Asp Gly His Glu Val Pro
                         980                 985                 990
         Gly Thr Gln Thr Pro Pro Gly Ser  Thr Pro Pro His Cys  Gly Pro Ser
                         995                 1000                1005
         Pro Glu  Pro Thr Gln Arg Pro  Pro Thr Ile Cys Glu  Arg Trp Arg
             1010                1015                1020
         Glu Asn Leu Leu Glu His Tyr  Gly Gly Thr Pro Arg  Asp Asp Gln
             1025                1030                1035
         Tyr Val  Pro Gln Cys Asp  Asp Leu Gly His Phe Ile  Pro Leu Gln
             1040                1045                1050
         Cys His  Gly Lys Ser Asp Phe  Cys Trp Cys Val Asp  Lys Asp Gly
             1055                1060                1065
         Arg Glu  Val Gln Gly Thr Arg  Ser Gln Pro Gly Thr  Thr Pro Ala
             1070                1075                1080
         Cys Ile  Pro Thr Val Ala Pro  Pro Met Val Arg Pro  Thr Pro Arg
             1085                1090                1095
         Pro Asp  Val Thr Pro Pro Ser  Val Gly Thr Phe Leu  Leu Tyr Thr
             1100                1105                1110
         Gln Gly  Gln Gln Ile Gly Tyr  Leu Pro Leu Asn Gly  Thr Arg Leu
             1115                1120                1125
         Gln Lys  Asp Ala Ala Lys Thr  Leu Leu Ser Leu His  Gly Ser Ile
             1130                1135                1140
         Ile Val  Gly Ile Asp Tyr Asp  Cys Arg Glu Arg Met  Val Tyr Trp
             1145                1150                1155
         Thr Asp  Val Ala Gly Arg Thr  Ile Ser Arg Ala Gly  Leu Glu Leu
             1160                1165                1170
         Gly Ala  Glu Pro Glu Thr Ile  Val Asn Ser Gly Leu  Ile Ser Pro
             1175                1180                1185
         Glu Gly  Leu Ala Ile Asp His  Ile Arg Arg Thr Met  Tyr Trp Thr
             1190                1195                1200
         Asp Ser  Val Leu Asp Lys Ile  Glu Ser Ala Leu Leu  Asp Gly Ser
             1205                1210                1215
         Glu Arg  Lys Val Leu Phe Tyr  Thr Asp Leu Val Asn  Pro Arg Ala
             1220                1225                1230
         Ile Ala  Val Asp Pro Ile Arg  Gly Asn Leu Tyr Trp  Thr Asp Trp
             1235                1240                1245
         Asn Arg  Glu Ala Pro Lys Ile  Glu Thr Ser Ser Leu  Asp Gly Glu
             1250                1255                1260
         Asn Arg  Arg Ile Leu Ile Asn  Thr Asp Ile Gly Leu  Pro Asn Gly
             1265                1270                1275
         Leu Thr  Phe Asp Pro Phe Ser  Lys Leu Leu Cys Trp  Ala Asp Ala
             1280                1285                1290
         Gly Thr  Lys Lys Leu Glu Cys  Thr Leu Pro Asp Gly  Thr Gly Arg
             1295                1300                1305
         Arg Val  Ile Gln Asn Asn Leu  Lys Tyr Pro Phe Ser  Ile Val Ser
             1310                1315                1320
         Tyr Ala  Asp His Phe Tyr His  Thr Asp Trp Arg Arg  Asp Gly Val
             1325                1330                1335
         Val Ser  Val Asn Lys His Ser  Gly Gln Phe Thr Asp  Glu Tyr Leu
             1340                1345                1350
```

```
Pro Glu Gln Arg Ser His Leu Tyr Gly Ile Thr Ala Val Tyr Pro
    1355            1360             1365

Tyr Cys Pro Thr Gly Arg Lys
    1370            1375

<210> SEQ ID NO 39
<211> LENGTH: 165
<212> TYPE: PRT
<213> ORGANISM: Homo sapiens

<400> SEQUENCE: 39

Met Glu Met Phe Gln Gly Leu Leu Leu Leu Leu Ser Met Gly
1               5                   10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Thr Met Thr Arg Val
            50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Ser Lys Ala Pro
        130                 135                 140

Pro Pro Ser Leu Pro Ser Pro Ser Arg Leu Pro Gly Pro Ser Asp Thr
145                 150                 155                 160

Pro Ile Leu Pro Gln
                165

<210> SEQ ID NO 40
<211> LENGTH: 98
<212> TYPE: PRT
<213> ORGANISM: Homo sapiens

<400> SEQUENCE: 40

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
                20                  25                  30

Glu Thr Tyr Gly Lys Leu Glu Ala Val Gln Tyr Lys Thr Gln Val Val
            35                  40                  45

Ala Gly Thr Asn Tyr Tyr Ile Lys Val Arg Ala Gly Asp Asn Lys Tyr
        50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe

<210> SEQ ID NO 41
<211> LENGTH: 210
```

```
<212> TYPE: PRT
<213> ORGANISM: Homo sapiens

<400> SEQUENCE: 41

Met Ala Ser Gly Gln Gly Pro Gly Pro Arg Gln Glu Cys Gly Glu
1               5                   10                  15

Pro Ala Leu Pro Ser Ala Ser Glu Glu Val Ala Gln Asp Thr Glu
                20                  25                  30

Glu Val Phe Arg Ser Tyr Val Phe Tyr Arg His Gln Gln Glu Gln
                35                  40                  45

Ala Glu Gly Val Ala Ala Pro Ala Asp Pro Glu Met Val Thr Leu Pro
                50                  55                  60

Leu Gln Pro Ser Ser Thr Met Gly Gln Val Gly Arg Gln Leu Ala Ile
65                  70                  75                  80

Ile Gly Asp Asp Ile Asn Arg Arg Tyr Asp Ser Glu Phe Gln Thr Met
                    85                  90                  95

Leu Gln His Leu Gln Pro Thr Ala Glu Asn Ala Tyr Glu Tyr Phe Thr
                100                 105                 110

Lys Ile Ala Thr Ser Leu Phe Glu Ser Gly Ile Asn Trp Gly Arg Val
                115                 120                 125

Val Ala Leu Leu Gly Phe Gly Tyr Arg Leu Ala Leu His Val Tyr Gln
            130                 135                 140

His Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                    165                 170                 175

Trp Val Ala Ala Leu Asn Leu Gly Asn Gly Pro Ile Leu Asn Val Leu
                180                 185                 190

Val Val Leu Gly Val Val Leu Leu Gly Gln Phe Val Val Arg Arg Phe
            195                 200                 205

Phe Lys
    210

<210> SEQ ID NO 42
<211> LENGTH: 15
<212> TYPE: PRT
<213> ORGANISM: Artificial Sequence
<220> FEATURE:
<223> OTHER INFORMATION: BH3 domain

<400> SEQUENCE: 42

Val Gly Arg Gln Leu Ala Ile Ile Gly Asp Asp Ile Asn Arg Arg
1               5                   10                  15

<210> SEQ ID NO 43
<211> LENGTH: 193
<212> TYPE: PRT
<213> ORGANISM: Homo sapiens

<400> SEQUENCE: 43

Met Ala Arg Ala Arg Gln Glu Gly Ser Ser Pro Glu Pro Val Glu Gly
1               5                   10                  15

Leu Ala Arg Asp Gly Pro Arg Pro Phe Pro Leu Gly Arg Leu Val Pro
                20                  25                  30

Ser Ala Val Ser Cys Gly Leu Cys Glu Pro Gly Leu Ala Ala Ala Pro
                35                  40                  45

Ala Ala Pro Thr Leu Leu Pro Ala Ala Tyr Leu Cys Ala Pro Thr Ala
            50                  55                  60
```

```
Pro Pro Ala Val Thr Ala Ala Leu Gly Gly Ser Arg Trp Pro Gly Gly
65                  70                  75                  80

Pro Arg Ser Arg Pro Arg Gly Pro Arg Pro Asp Gly Pro Gln Pro Ser
                85                  90                  95

Leu Ser Leu Ala Glu Gln His Leu Glu Ser Pro Val Pro Ser Ala Pro
            100                 105                 110

Gly Ala Leu Ala Gly Gly Pro Thr Gln Ala Ala Pro Gly Val Arg Gly
            115                 120                 125

Glu Glu Glu Gln Trp Ala Arg Glu Ile Gly Ala Gln Leu Arg Arg Met
130                 135                 140

Ala Asp Asp Leu Asn Ala Gln Tyr Glu Arg Arg Gln Glu Glu Gln
145                 150                 155                 160

Gln Arg His Arg Pro Ser Pro Trp Arg Val Leu Tyr Asn Leu Ile Met
                165                 170                 175

Gly Leu Leu Pro Leu Pro Arg Gly His Arg Ala Pro Glu Met Glu Pro
            180                 185                 190

Asn
```

<210> SEQ ID NO 44
<211> LENGTH: 187
<212> TYPE: PRT
<213> ORGANISM: Corynebacterium diphtheriae

<400> SEQUENCE: 44

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala
            180                 185
```

<210> SEQ ID NO 45
<211> LENGTH: 209
<212> TYPE: PRT
<213> ORGANISM: Pseudomonas aeruginosa

<400> SEQUENCE: 45

```
Gly Asp Ile Ser Phe Ser Thr Arg Gly Thr Gln Asn Trp Thr Val Glu
1               5                   10                  15

Arg Leu Leu Gln Ala His Arg Gln Leu Glu Glu Arg Gly Tyr Val Phe
            20                  25                  30

Val Gly Tyr His Gly Thr Phe Leu Glu Ala Ala Gln Ser Ile Val Phe
            35                  40                  45

Gly Gly Val Arg Ala Arg Ser Gln Asp Leu Asp Ala Ile Trp Arg Gly
50                  55                  60

Phe Tyr Ile Ala Gly Asp Pro Ala Leu Ala Tyr Gly Tyr Ala Gln Asp
65                  70                  75                  80

Gln Glu Pro Asp Ala Arg Gly Arg Ile Arg Asn Gly Ala Leu Leu Arg
            85                  90                  95

Val Tyr Val Pro Arg Ser Ser Leu Pro Gly Phe Tyr Arg Thr Gly Leu
            100                 105                 110

Thr Leu Ala Ala Pro Glu Ala Ala Gly Glu Val Glu Arg Leu Ile Gly
            115                 120                 125

His Pro Leu Pro Leu Arg Leu Asp Ala Ile Thr Gly Pro Glu Glu Glu
            130                 135                 140

Gly Gly Arg Leu Glu Thr Ile Leu Gly Trp Pro Leu Ala Glu Arg Thr
145                 150                 155                 160

Val Val Ile Pro Ser Ala Ile Pro Thr Asp Pro Arg Asn Val Gly Gly
            165                 170                 175

Asp Leu Asp Pro Ser Ser Ile Pro Asp Lys Glu Gln Ala Ile Ser Ala
            180                 185                 190

Leu Pro Asp Tyr Ala Ser Gln Pro Gly Lys Pro Arg Glu Asp Leu
            195                 200                 205

Lys

<210> SEQ ID NO 46
<211> LENGTH: 5
<212> TYPE: PRT
<213> ORGANISM: Artificial Sequence
<220> FEATURE:
<223> OTHER INFORMATION: linker peptide

<400> SEQUENCE: 46

Ala Ala Ala Leu Glu
1               5

<210> SEQ ID NO 47
<211> LENGTH: 98
<212> TYPE: PRT
<213> ORGANISM: Homo sapiens

<400> SEQUENCE: 47

Met Ile Pro Trp Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Asp
            35                  40                  45

Ala Gly Thr Asn Tyr Tyr Ile Lys Val Arg Ala Gly Asp Asn Lys Tyr
50                  55                  60

Met His Leu Lys Val Phe Asn Gly Pro Pro Gly Gln Asn Glu Asp Leu
65                  70                  75                  80

Val Leu Thr Gly Tyr Gln Val Asp Lys Asn Lys Asp Asp Glu Leu Thr
            85                  90                  95
```

<210> SEQ ID NO 48
<211> LENGTH: 98
<212> TYPE: PRT
<213> ORGANISM: Homo sapiens

<400> SEQUENCE: 48

Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Leu
        35                  40                  45

Ala Ser Thr Asn Tyr Tyr Ile Lys Val Arg Ala Gly Asp Asn Lys Tyr
    50                  55                  60

Met His Leu Lys Val Phe Asn Gly Pro Pro Gly Gln Asn Glu Asp Leu
65                  70                  75                  80

Val Arg Ser Gly Tyr Gln Val Asp Lys Asn Lys Asp Asp Glu Leu Thr
                85                  90                  95

Gly Phe

<210> SEQ ID NO 49
<211> LENGTH: 98
<212> TYPE: PRT
<213> ORGANISM: Homo sapiens

<400> SEQUENCE: 49

Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe

<210> SEQ ID NO 50
<211> LENGTH: 98
<212> TYPE: PRT
<213> ORGANISM: Homo sapiens

<400> SEQUENCE: 50

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Leu
        35                  40                  45

Ala Ser Thr Asn Tyr Tyr Ile Lys Val Arg Ala Gly Asp Asn Lys Tyr
    50                  55                  60

```
Met His Leu Lys Val Phe Lys Ser Leu Pro Gly Gln Asn Glu Asp Leu
 65                  70                  75                  80

Val Leu Thr Gly Tyr Gln Val Asp Lys Asn Lys Asp Asp Glu Leu Thr
                 85                  90                  95

Gly Phe

<210> SEQ ID NO 51
<211> LENGTH: 98
<212> TYPE: PRT
<213> ORGANISM: Homo sapiens

<400> SEQUENCE: 51

Met Ile Pro Gly Gly Leu Ser Glu Ala Lys Pro Ala Thr Pro Glu Ile
  1               5                  10                  15

Gln Glu Ile Val Asp Lys Val Lys Pro Gln Leu Glu Glu Lys Thr Asn
                 20                  25                  30

Glu Thr Tyr Gly Lys Leu Glu Ala Val Gln Tyr Lys Thr Gln Val Val
             35                  40                  45

Ala Gly Thr Asn Tyr Tyr Ile Lys Val Arg Ala Gly Asp Asn Lys Tyr
         50                  55                  60

Met His Leu Lys Val Phe Asn Gly Pro Pro Gly Gln Asn Glu Asp Leu
 65                  70                  75                  80

Val Arg Ser Gly Tyr Gln Val Asp Lys Asn Lys Asp Asp Glu Leu Thr
                 85                  90                  95

Gly Phe

<210> SEQ ID NO 52
<211> LENGTH: 98
<212> TYPE: PRT
<213> ORGANISM: Homo sapiens

<400> SEQUENCE: 52

Met Ile Pro Gly Gly Leu Ser Glu Ala Lys Pro Ala Thr Pro Glu Ile
  1               5                  10                  15

Gln Glu Ile Val Asp Lys Val Lys Pro Gln Leu Glu Glu Lys Thr Asn
                 20                  25                  30

Glu Thr Tyr Gly Lys Leu Glu Ala Val Gln Tyr Lys Thr Gln Val Leu
             35                  40                  45

Ala Ser Thr Asn Tyr Tyr Ile Lys Val Arg Ala Gly Asp Asn Lys Tyr
         50                  55                  60

Met His Leu Lys Val Phe Asn Gly Pro Pro Gly Gln Asn Glu Asp Leu
 65                  70                  75                  80

Val Arg Ser Gly Tyr Gln Val Asp Lys Asn Lys Asp Asp Glu Leu Thr
                 85                  90                  95

Gly Phe
```

THERAPEUTIC NANOCONJUGATES AND USES THEREOF

CROSS-REFERENCE TO RELATED APPLICATIONS

This application is a U.S. National Phase application of PCT/EP2018/069303 filed on Jul. 16, 2018, claiming priority to European Application No. 17382461.6, filed on Jul. 14, 2017, both of which are incorporated herein by reference in their entireties.

REFERENCE TO SEQUENCE LISTING SUBMITTED ELECTRONICALLY

A sequence listing containing the file named DFA_P14353PC00_SequenceListing_ST25 which is 56,351 bytes (measured in MS-Windows®) and created on Jan. 14, 2020, comprises 52 sequences, is provided herewith via the USPTO's EFS system, and is incorporated herein by reference in its entirety.

FIELD OF THE INVENTION

The present invention relates to the field of nanostructured protein materials, more specifically to therapeutic agent-carrying fusion proteins which can be used for therapy.

BACKGROUND OF THE INVENTION

The systemic administration of drugs in form of nanoconjugates benefits from enhanced drug stability when compared to free molecules. Valuable additional properties such as cell targeting might be also merged into a given hybrid composite through the chemical incorporation of functional groups in nanoscale vehicles, taking profit from the high surface/volume ratio of nanomaterials. When administered systemically, the resulting drug loaded conjugates sizing between ~8 and 100 nm escape from renal filtration in absence of aggregation in lung or other highly vascularized organs. This fact, combined with appropriate physicochemical properties of the material might result in extended circulation time and prolonged drug exposure to target organs, thus enhancing the therapeutic impact and benefits for the patient.

Among the diversity of materials under investigation as drug carriers, that includes metals, ceramics, polymers and carbon nanotubes, proteins offer unique properties regarding biocompatibility and degradability that, in the context of rising nanotoxicological concerns, make them especially appealing. As the engineering of protein self-assembling into nanostructured materials is rapidly progressing and the control over the final geometry and physicochemical properties becomes tighter, protein materials are gaining functional and structural versatility as vehicles from chemically coupled drugs.

In fact, the attachment of a cytotoxic "payload" to an antibody to form an antibody-drug conjugate (ADC) has been shown to provide a mechanism for selective delivery of the cytotoxic agent to cancer cells via the specific binding of the antibody to cancer-selective cell surface molecules. Multiple examples of this strategy have been proved to be effective, like gemtuzumab ozogamicin, which comprises an anti-CD33 antibody conjugated to a highly potent DNA-targeting antibiotic, calicheamicin, which was used against acute myeloid leukemia. Also, maytansinoids, a highly potent microtubule-disrupting agents, have been tested as payloads for ADCs, resulting in the formulation ado-trastuzumab emtansine for treating HER2-positive breast cancer.

Nonetheless, the structural complexity of antibodies may become a cumbersome hindrance in terms of cost and synthesis. The inventors previously probed into the field of nanomedicine by applying a nanoarchitectonic principle based on the addition, to a core protein, of a cationic N-terminal domain plus a C-terminal poly-histidine. [Serna, N. et al. 2016. Nanomedicine, 12:1241-51] It has been described in the art that these end-terminal tags and the resulting charge balance in the whole fusion promote self-assembling and oligomerization of monomeric proteins as robust toroid nanoparticles, stable in plasma [Cespedes, M. V. et al. 2014. ACS Nano., 8:4166-4176] and with high cellular penetrability if empowered with cell-targeting peptides. [Xu, Z. K. et al. 2015. Materials Letters, 154:140-3] The building blocks of these protein structures might also contain functional peptides such as cell-targeting agents, endosomolytic agents or nuclear localization signals, in form of fused stretches with modular organization.

Since current therapy methods still show a margin of failure, mostly due to tumor resistance phenomena which may result from intra-tumor clonal selection of those cells most resistant to the chemotherapy, for instance, there is still in the art a need for the development of more specific therapeutic approaches which can be targeted to the concrete tumor cells responsible for therapy failure and tumor progression while reducing the side and off-target effects of the therapeutic agents.

SUMMARY OF THE INVENTION

In a first aspect, the invention relates to a fusion protein comprising
  (i) a polycationic peptide,
  (ii) an intervening polypeptide region and
  (iii) a positively charged amino acid-rich region,
  wherein the intervening polypeptide region is conjugated to at least one therapeutic agent.

In further aspects, the invention relates to a method to prepare the fusion protein of the first aspect, to a method to prepare nanoparticles comprising multiple copies of the fusion protein according to the first aspect of the invention, to a nanoparticle comprising multiple copies of the fusion protein of the invention or a nanoparticle which has been obtained by the method of the invention to prepare nanoparticles.

The invention also pertains to a fusion protein or a nanoparticle according to the invention for use in medicine.

In a final aspect, the invention relates to a fusion protein or a nanoparticle according to the invention for use in the treatment of cancer.

DETAILED DESCRIPTION OF THE INVENTION

Figure 1:
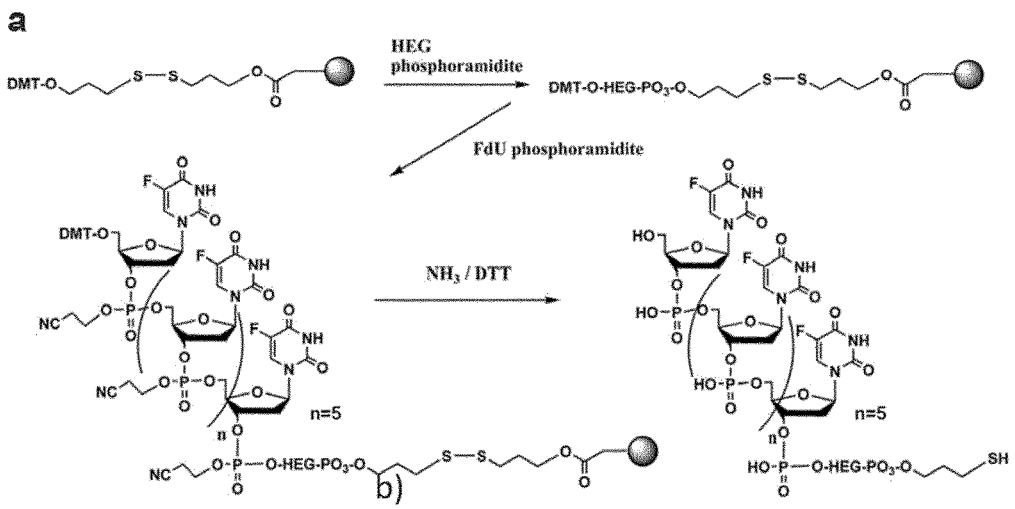
FIG. 1. Synthesis of thiol functionalized oligo-FdU and physicochemical characterization (a) Synthesis of Oligo-FdU functionalized with thiol: the pentamer oligo-(FdU)5-SH (oligo-FdU) was synthesized in 1 μmol scale on an RNA/DNA synthesizer using β-cyanoethylphosphoramiditechemistry. 3'-Thiol-modifier C3 controlled pore glass (CPG) (Link Technologies) was used as solid support for the synthesis. First the hexaethyleneglycol (HEG) phosphoramidite (Glen Research) was incorporated. Then, the synthesis was completed by repetitive additions of the dimethoxytrityl (DMT)-protected-5-fluoro-2'-deoxyuridinephosphoramidite unit. After assembling of the sequence, oligonucleotide support was treated with aqueous ammonia (32%) with 0.1 M DTT (1,4-dithiothreitol) for 2 h at room temperature. 18 The ammonia solutions were concentrated to dryness and the product was desalted on NAP-10 (Sephadex G-25) columns eluted with water prior to use. Free oligo-FdU synthesis: Control pentamer oligo-FdU without HEG and thiol groups was prepared as before but using 3'-succinyl-FdU controlled pore glass as solid support. Finally, the oligonucleotide was deprotected with aqueous ammonia (32%) for 2 h at room temperature. (b) Physicochemical characterization of the Oligo-(FdU)5-SH. HPLC analysis of pentamer FdU-HEG-SH (Conditions: X-bridge™ OST C18 (10×50 mm, 2.5 µm); 20 min linear gradient from 0% to 40%, flow rate 2 mL/min; solution A was 5% ACN in 0.1 M aqueous triethylammonium acetate (TEAA) and B 70% ACN in 0.1 M aqueous TEAA. (c) UV spectra of pentamer FdU-HEG-SH. The pentamer was quantified by absorption at 260 nm. (d) MS spectrum (MALDI-TOF) of pentamer FdU-HEG-SH (oligo-FdU). M calculated 1976.2 M found 1974.0. (e) MS spectrum (MALDI-TOF) of control pentamer FdU (free oligo-FdU). M calculated 1478.1, M found 1476.5.
Figure 1:
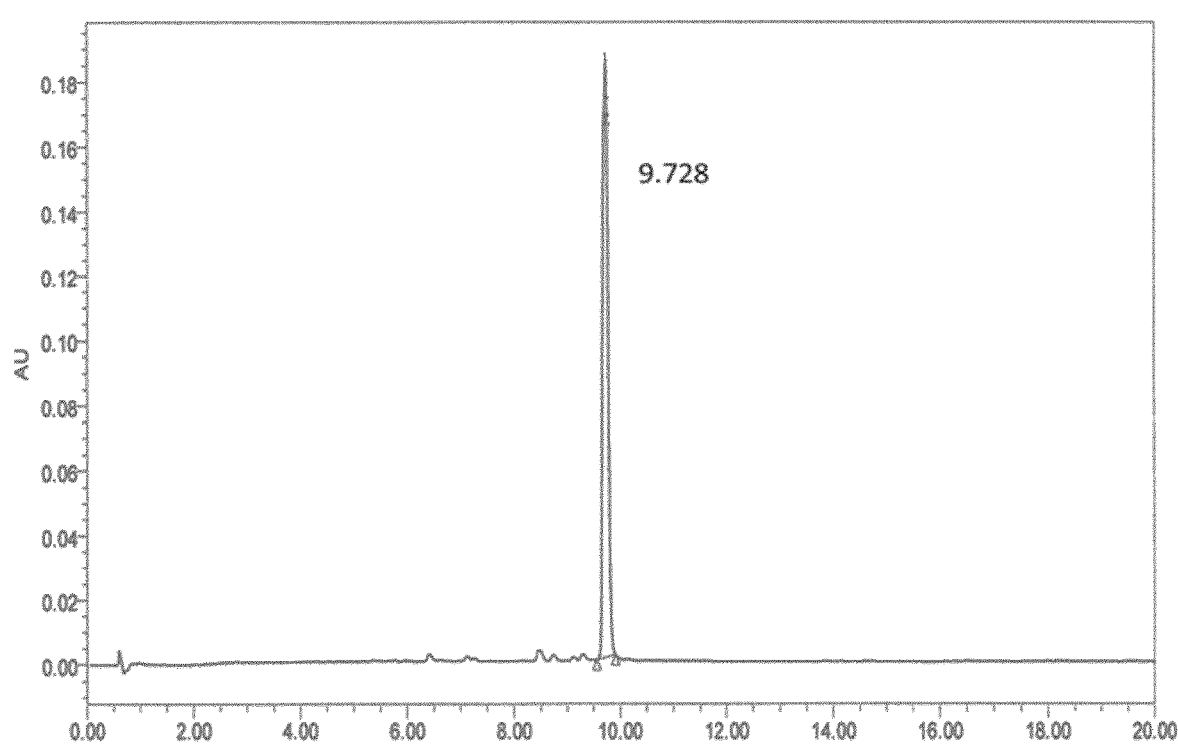
Figure 1:
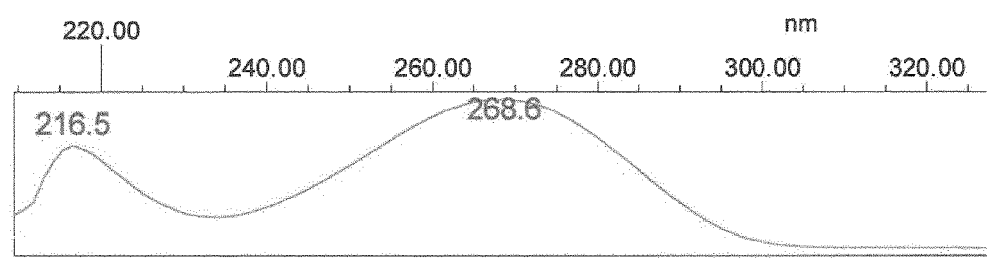
Figure 1:
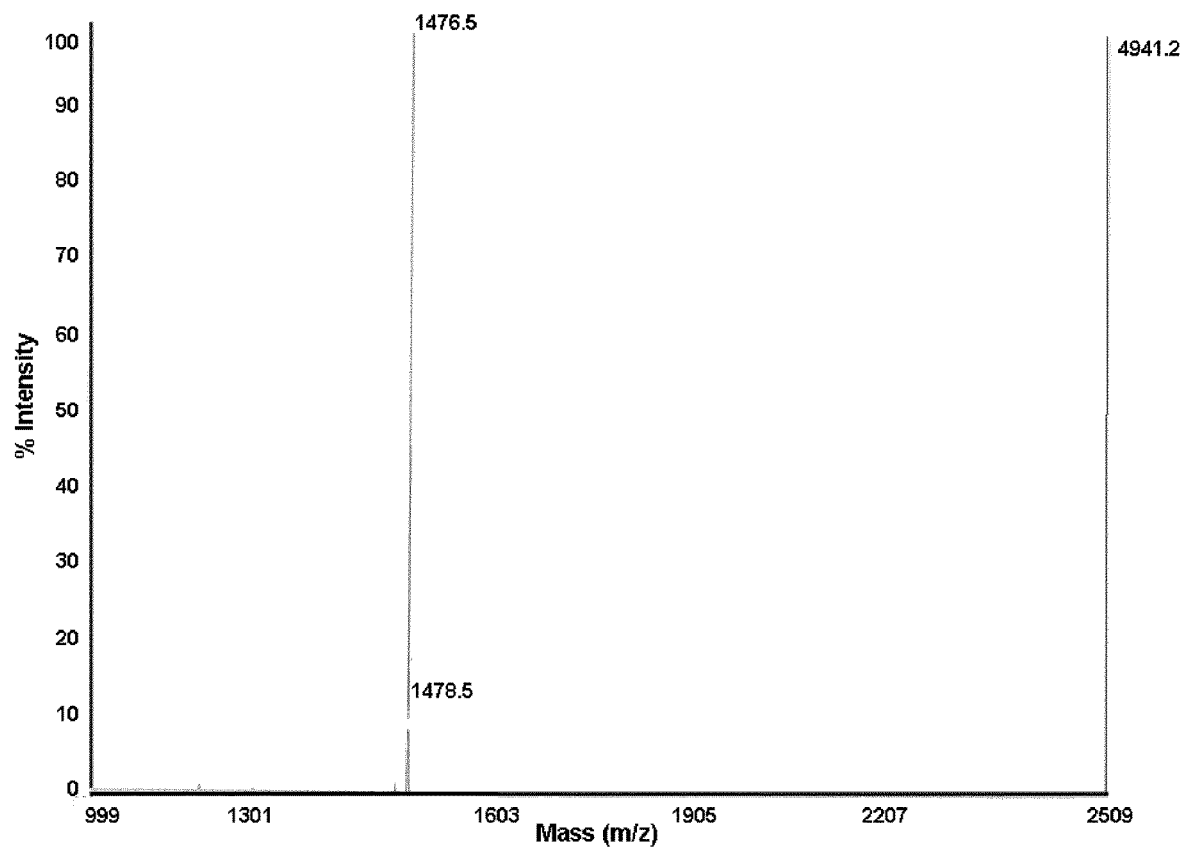
Figure 1:
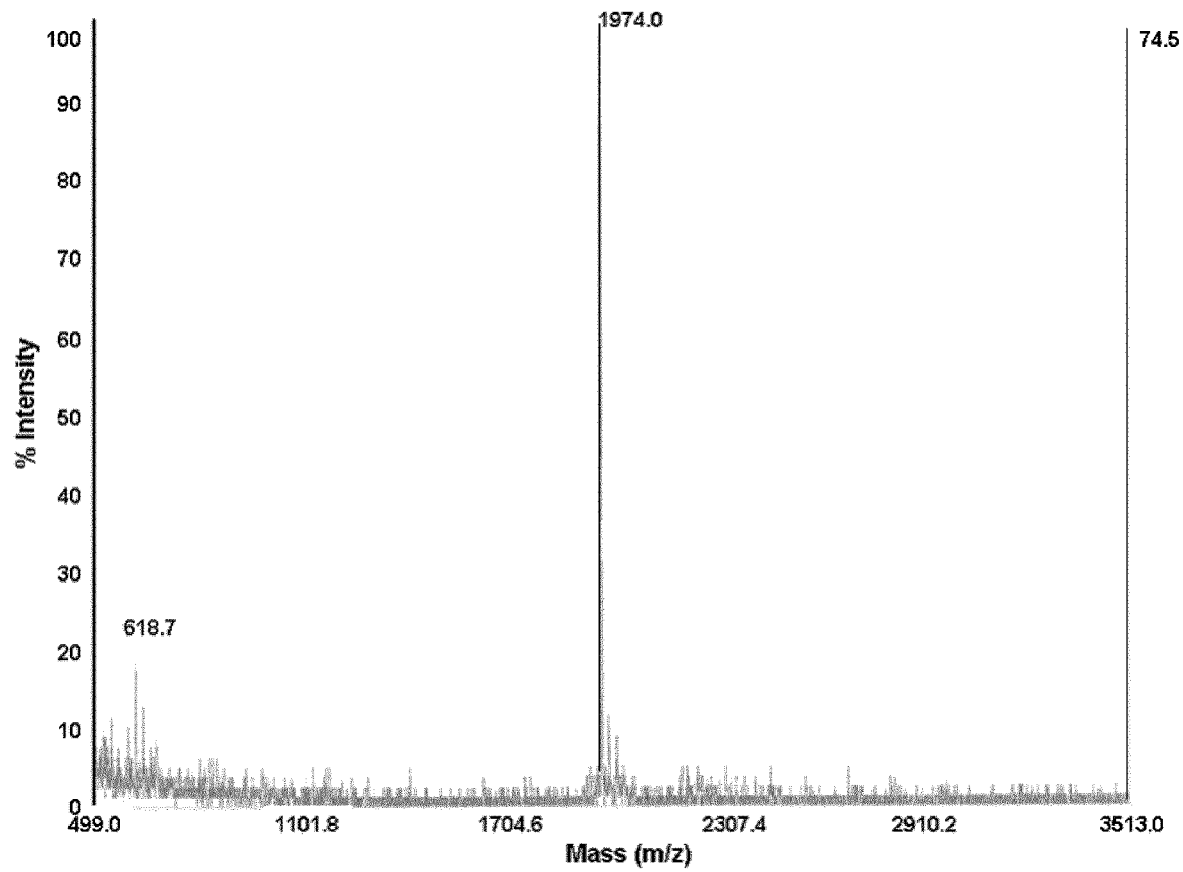

The inventors tested the principle behind the architecture of nanostructured proteins through the use of fusion proteins which included polycationic peptides with cell selectivity effects and proteins without an inherent physiological or biological activity. The fusion protein, later conjugated with therapeutic agents, the inventors observed that, surprisingly, the fusion proteins functioned as an effective target-selective delivery system for the therapeutic agents.

Fusion Proteins of the Invention

Thus, in a first aspect, the invention relates to a fusion protein comprising
(i) a polycationic peptide,
(ii) an intervening polypeptide region and
(iii) a positively charged amino acid-rich region,
wherein the intervening polypeptide region is conjugated to at least one therapeutic agent.

The term "fusion protein" is well known in the art, referring to a single polypeptide chain artificially designed which comprises two or more sequences from different origins, natural and/or artificial. The fusion protein, per definition, is never found in nature as such.

The term "single polypeptide chain", as used herein means that the polypeptide components of the fusion protein can be conjugated end-to-end but also may include one or more optional peptide or polypeptide "linkers" or "spacers" intercalated between them, linked by a covalent bond.

The term "peptide" or "polypeptide", as used herein, generally refers to a linear chain of around 2 to 40 amino acid residues joined together with peptide bonds. It will be understood that the terms "peptide bond", "peptide", "polypeptide" and protein are known to the person skilled in the art. From here on, "peptide" and "polypeptide" will be used indistinctly.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

The term "conjugate", as used herein, refers to any compound resulting from the covalent attachment of two or more individual compounds. In the present invention, conjugate refers to the intervening polypeptide region and at least one therapeutic agent which are covalently coupled, being said coupling direct or via a linking compound.

The terms "covalent coupling" or "covalent attachment" mean that the polypeptide region and at least one therapeutic agent are either directly covalently joined through a chemical covalent bond to one another, or else are indirectly covalently joined to one another through an intervening moiety or moieties, such as a linker, or a bridge, or a spacer, moiety or moieties.

A. The Polycationic Peptide

The term "polycationic peptide" or "first positively charged amino acid-rich region" as used herein, corresponds to a polypeptide sequence containing multiple positively charged amino acids. The polycationic peptide may be formed exclusively by positively charged amino acids or may contain other amino acids provided that the overall net charge of the region at pH 7 is positive.

It is well known in the art that amino acids and their corresponding amino acid residues possess different properties depending on their side chains and they may be grouped depending on those properties. Thus, at physiological pH, five amino acids show an electrical charge: arginine, histidine, and lysine are positively charged while aspartic acid and glutamic acid are negatively charged. The person skilled in the art will acknowledge then that the polycationic peptide of the invention corresponds to a polypeptide with a net electrical charge of more than one positive charge in physiological pH conditions. Accordingly, the polycationic peptide of the invention is not limited by the presence of one or more negatively charge amino acid residues as long as there are always enough positively charged amino acid residues to result in a net positive electrical charge of two or more.

Thus, in one embodiment of the invention, the polycationic peptide of the invention is selected from the group consisting of
(i) an arginine-rich sequence,
(ii) a sequence which is capable of specifically interacting with a receptor on a cell surface and promoting internalization of the fusion protein on said cell,
(iii) the GW-H1 peptide,
(iv) a CD44 ligand,
(v) a peptide capable of crossing the blood-brain barrier,
(vi) a cell penetrating peptide and
(vii) a nucleolin-binding peptide.

(i) Arginine-Rich Sequence

As aforementioned, the arginine amino acid and its residue present positive charge at physiological pH. It will be understood that an "arginine-rich sequence" refers to a polypeptide sequence containing multiple arginine residues. Thus, the polypeptide sequence may comprise 33%, preferably 40%, preferably 45%, preferably 50%, preferably 55%, preferably 60%, preferably 65%, preferably 70%, preferably 75%, preferably 80%, preferably 85%, more preferably 90%, more preferably 95%, even more preferably 99%, yet even more preferably 100% of the amino acid residues of its complete sequence as arginine residues. It will be understood that whenever the sequence of the arginine-rich sequence comprises less than the 100% of the sequence as arginine residues, these residues do not need to be all adjacent or contiguous with respect to each other.

The person skilled in the art will recognize that a polypeptide with one or more arginine residues will be a polycationic peptide as long as the total positive electrical charge of the polypeptide at physiological pH is 2 or more, resulting not only from the positive electrical charges of the arginine residues but also from any other positively charged amino acids.

In an embodiment of the invention, the polycationic peptide of the invention is an arginine-rich sequence.

In a preferred embodiment of the invention, the arginine-rich sequence of the polycationic peptide of the invention is selected from the group consisting of SEQ ID NO: 1, SEQ ID NO: 2, SEQ ID NO: 3 and SEQ ID NO: 4.

(ii) Sequence which is Capable of Specifically Interacting with a Receptor on a Cell Surface and Promoting Internalization of the Fusion Protein on Said Cell The terms "sequence which is capable of specifically interacting with a receptor on a cell surface and promoting internalization of the fusion protein on said cell", as used herein, refers to any polypeptide sequence which binds to a receptor on the surface of a cell, wherein the receptor undergoes endocytosis in response to the binding of said polypeptide sequence. This binding specificity allows the delivery of the polypeptide sequence, as well as the rest of the fusion protein which it is a part of, to the cell, tissue or organ which expresses said receptor. In this way, a fusion protein comprising said polypeptide sequence will be directed specifically to said cells when administered to an animal or contacted in vitro with a population of cells of different types.

The term "receptor" denotes a cell-associated protein that binds to a bioactive molecule termed a "ligand". Both "receptor" and "ligand" are commonly known to those skilled in the art.

As used herein, "internalization" refers to a process by which a molecule or a construct comprising a molecule binds to a target element on the outer surface of the cell membrane and the resulting complex is internalized by the cell. Internalization may be followed up by dissociation of the resulting complex within the cytoplasm. The target element, along with the molecule or the construct, may then localize to a specific cellular compartment. Preferably, the polycationic peptide of the invention, besides promoting internalization, will facilitate endosomal escape of the fusion protein.

A wide array of uptake receptors and carriers, with an even wider number of receptor-specific ligands, are known in the art.

Non-limiting examples of receptors which may be targeted by the polycationic of the invention include an angiotensin receptor, a bombesin receptor, a bradykinin receptor, a calcitonin receptor, a chemokine receptor, a cholecystokinin receptor, a corticotropin-releasing factor receptor, an endothelin receptor, an ephrin receptor, a formylpeptide receptor, a Frizzled receptor, a galanin receptor, a the growth hormone secretagogue receptor (Ghrelin) receptor, a Kisspeptin receptor, a melanocortin receptor, Neuropeptide FF/neuropeptide AF receptor, a neuropeptide S receptor, a neuropeptide W/neuropeptide B receptor, a neuropeptide Y receptor, a neurotensin receptor, an orexin receptors, a peptide P518 receptor, a somatostatin receptor, a tachykinin receptor, a Toll-like receptor, a vasopressin and oxytocin receptor and a VEGF receptor.

In a preferred embodiment of the invention, the polycationic peptide comprising a sequence which is capable of specifically interacting with a receptor on a cell surface and promoting internalization of the fusion protein on said cell is a CXCR4 ligand.

The term "CXCR4", as used herein, refers to a G protein-coupled, seven-transmembrane chemokine receptor. Like other chemokine receptors, CXCR4 plays an important role in immune and inflammatory responses by mediating the directional migration and activation of leukocytes CXCR4 is expressed or overexpressed in a variety of cancer cell lines and tissues including breast, prostate, lung, ovarian, colon, pancreatic, kidney, and brain, as well as non-Hodgkin's lymphoma and chronic lymphocytic leukemia. The only known ligand to CXCR4 is stromal cell-derived factor-1 (SDF-1, or CXCL12). The interaction between CXCR4 and SDF-1 plays an important role in multiple phases of tumorigenesis, including tumor growth, invasion, angiogenesis, and metastasis.

The expression "specifically binding to CXCR4", as used herein refers to the ability of the conjugates of the invention to bind more frequently, more rapidly, with greater duration and/or with greater affinity to CXCR4 or cell expressing same than it does with alternative receptors or cells without substantially binding to other molecules.

Binding affinity is measured, for instance, as described by Tamamura et al. by the oil-cushion method [see Hesselgesset et al, 1998, J.Immunol., 160:877-883] comprising contacting the peptide with CXCR4-transfected cell line (e.g. CHO cells) and a labeled CXCR4 ligand (e.g. $^{125}$I-SDF-1$\alpha$) and measuring the inhibition percentage of the targeting peptide against the binding of the labeled CXCR4 ligand.

Specific binding can be exhibited, e.g., by a low affinity targeting agent having a Kd of at least about $10^{-4}$ M. e.g., if CXCR4 has more than one binding site for a ligand, a ligand having low affinity can be useful for targeting. Specific binding also can be exhibited by a high affinity ligands, e.g. a ligand having a Kd of at least about of $10^{-7}$ M, at least about $10^{-8}$ M, at least about $10^{-9}$ M, at least about $10^{-10}$ M, or can have a Kd of at least about $10^{-11}$ M or $10^{-12}$ M or greater. Both low and high affinity-targeting ligands are useful for incorporation in the conjugates of the present invention.

The ability of the conjugate of the invention to be internalized by cells expressing CXCR4 may be conveniently determined by fluorescence methods in the case that the conjugate comprises a fluorescent protein, such as GFP. Such fusion proteins can be obtained by preparing a recombinant nucleic acid wherein the nucleic acids encoding the T22 peptide and the fluorescent protein are fused in frame and expressed in an adequate host cell or organism. The fusion protein is then contacted with a culture of cells expressing CXCR4 or in vivo with a tissue which expresses CXCR4 for an appropriate amount of time, after which fluorescence microscopy may be used to determine whether the construct penetrated the cell. Presence of fluorescence in the cytoplasm may be further investigated by comparing the fluorescence microscopy image resulting from the fluorescent protein to that obtained with a known cytoplasmic stain.

The expression "facilitate endosomal escape", as used herein, refers to the ability of the polycationic peptide to induce the release of the fusion proteins from the endosomal compartment after internalization by receptor-mediated endocytosis.

In an even more preferred embodiment of the invention, the CXCR4 ligand is selected from the group comprising the T22 peptide (SEQ ID NO: 5), the V1 peptide (SEQ ID NO: 6), the CXCL12 peptide (SEQ ID NO: 7), the vCCL2 peptide (SEQ ID NO: 8) or a functionally equivalent variant thereof.

The T22 peptide corresponds to a peptide derived from the protein polyphemusin II (extracted from hemocyte debris from *Lymulus polyphemus*). The vCCL2 corresponds to the viral macrophage inflammatory protein-II, an homologue of human chemokine CCL2 encoded by human herpesvirus 8. The V1 peptide corresponds to residues 1-21 of the N-terminus of vCCL2. CXCL12, C-X-C motif chemokine 12, also known as stromal cell-derived factor 1 (SDF1), is a member of the chemokine family that acts as a proinflammatory mediator. All four peptides are known to have interactions with the CXCR4 receptor, as shown in Liang, X. 2008. Chem. Biol. Drug. Des. 72:91-110.

In one embodiment, the targeting peptide is the selected from the group consisting of:

the T140 peptide having the sequence $RRX_1CYRKX_2PYRX_3CR$ (SEQ ID NO: 9) wherein $X_1$ is L-3-(2-naphtyl)alanine, $X_2$ is D-Lys and $X_3$ is L-Citrulline.

the TN14003 peptide having the sequence RRX$_1$CYX$_2$KX$_3$PYRX$_4$CR (SEQ ID NO: 10) wherein X$_1$ is L-3-(2-naphtyl)alanine, X$_2$ is L-Citrulline, X$_3$ is dLys and X$_4$ is L-Citrulline, the TC14012 peptide having the sequence RRX$_1$CYEKX$_2$PYRX$_3$CR (SEQ ID NO: 11) wherein X$_1$ is L-3-(2-naphtyl)alanine, X$_2$ is D-Citrulline and X$_3$ is L-Citrulline, the TE14011 peptide having the sequence RRX$_1$CYX$_2$KX$_3$PYRX$_4$CR (SEQ ID NO: 12) wherein X$_1$ is L-3-(2-naphtyl)alanine, X$_2$ is L-Citrulline, X$_3$ is D-Glu and X$_4$ is L-Citrulline and the TZ14011 peptide having the sequence RRX$_1$CYX$_2$KX$_3$PYRX$_4$CR (SEQ ID NO: 13) wherein X$_1$ is L-3-(2-naphtyl)alanine, X$_2$ is L-Citrulline, X$_3$ is D-Lys and X$_4$ is L-Citrulline or the variant thereof wherein the N-terminal Arginine residue is acetylated (known Ac-TZ14011).

The terms "functional variant" and "functionally equivalent variant" are interchangeable and are herein understood as all those peptides derived from the T22, the V1, the CXCL12, and/or the vCCL2 peptides by means of modification, insertion and/or deletion of one or more amino acids, provided that the function of binding to CXCR4 and internalizing the fusion protein is substantially maintained.

In one embodiment, functionally equivalent variants of the cationic polypeptides are those showing a degree of identity with respect to the human T22, V1, CXCL12 and/or the vCCL2 peptides, according to their respective SEQ ID NOs, greater than at least 40%, at least 50%, at least 60%, at least 70%, at least 80%, at least 85%, at least 90%, at least 95%, at least 96%, at least 97%, at least 98% or at least 99%. The degree of identity between two amino acid sequences can be determined by conventional methods, for example, by means of standard sequence alignment algorithms known in the state of the art, such as, for example BLAST [Altschul S. F. et al., J. Mol. Biol., 1990 Oct. 5; 215(3):403-10]. The cationic polypeptides of the invention may include post-translational modifications, such as glycosylation, acetylation, isoprenylation, myristoylation, proteolytic processing, etc.

Alternatively, suitable functional variants of the cationic polypeptide are those wherein one or more positions contain an amino acid which is a conservative substitution of the amino acid present in the T22, V1, CXCL12, and/or vCCL2 peptides mentioned above. "Conservative amino acid substitutions" result from replacing one amino acid with another having similar structural and/or chemical properties For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). Selection of such conservative amino acid substitutions is within the skill of one of ordinary skill in the art and is described, for example by Dordo et al. et al., [J. Mol. Biol, 1999, 217; 721-739] and Taylor et al., [J. Theor. Biol., 1986, 119:205-218].

A suitable assay for determining whether a given peptide can be seen as a functionally equivalent variant thereof is, for instance, the following assay: a putative T22, V1, CXCL12 or vCCL2 peptide variant is fused in frame with a marker polypeptide (e.g. a fluorescent protein). Such fusion proteins can be obtained by preparing a recombinant nucleic acid wherein the nucleic acids encoding the peptide and the fluorescent protein are fused in frame and expressed in an adequate host cell or organism. The fusion protein is then contacted with a culture of cells CXCR4 (e.g. HeLa cells) for an appropriate amount of time after which fluorescence microscopy may be used to determine whether the construct penetrated the cell. If the peptide is a functionally equivalent variant of the corresponding peptide, the marker protein will be internalized and presence of fluorescence in the cytoplasm of the cell will be visible. Furthermore, the performance of the functionally equivalent variant can be assayed by comparing the fluorescence microscopy image resulting from the fluorescent protein to that obtained with a known cytoplasmic stain (e.g. DAPI).

(iii) The GW-H1 Peptide

The GW-H1 peptide was previously described by Chen and colleagues [Chen, Y-L.S. et al. 2012. Peptides, 36:257-265]. The GW-H1 peptide was first selected as an antimicrobial peptide but it is also characterized by its capability to bind to cell membranes, internalize itself to the cytoplasm, and migrate to the nuclei in eukaryotic cells. Once inside the cell, GW-H1 is capable induce apoptosis. It has been proposed that GW-H1 exerts its cytolytic activity by folding into an amphipathic helix [Chen and colleagues, supra]. Therefore, this peptide is supposed to exert its cell lytic effects by two sequential events consisting on binding to cell membranes followed by permeabilization.

In a preferred embodiment of the invention, the polycationic peptide of the invention is the GW-H1 peptide, which has the SEQ ID NO: 14.

(iv) A CD44 Ligand

CD44 is a cell-surface transmembrane glycoprotein involved in cell-cell and cell-matrix interactions, cell adhesion and migration. CD44 has been implicated in inflammation and in diseases such as cancer [Bajorath, J. 2000. Proteins. 39:103-111]. Many isoforms are known, which are expressed in a cell-specific manner and also differentially glycosylated.

Accordingly, a "CD44 ligand" will be a molecule capable of binding to CD44. CD44 is the major surface receptor for Hyaluronan, a component of the extracellular matrix, but it has other ligands, such as chondroitin sulfate, the heparin-biding domain of fibronectin, osteopontin, serglycin, collagen and laminin. Besides, CD44 can also interact with metalloproteinases and selectins.

In an embodiment of the invention, the polycationic peptide of the invention is a CD44 ligand. In a preferred embodiment of the invention, the CD44 ligand is selected from the group consisting of A5G27 (SEQ ID NO: 15) and FNI/II/V (SEQ ID NO: 16).

The peptide FNI/II/V corresponds to the HBFN-fragment V of Fibronectin. The peptide A5G27 corresponds to a peptide of the a5 chain of Laminin [Pesarrodona, M. et al. 2014. Int. J. of Pharmaceutics. 473:286-295].

(v) Peptide Capable of Crossing the Blood-Brain Barrier

It is well known in the art that one major obstacle for the development of therapeutic approaches for brain pathologies is the blood-brain barrier (BBB). The brain is shielded against potentially toxic substances by the presence of two barrier systems: the blood-brain barrier (BBB) and the blood-cerebrospinal fluid barrier (BCSFB). The BBB is considered to be the major route for the uptake of serum ligands since its surface area is approximately 5000-fold greater than that of BCSFB. The brain endothelium, which constitutes the BBB, represents the major obstacle for the use of potential drugs against many disorders of the CNS. As a general rule, only small lipophilic molecules may pass across the BBB, i.e., from circulating systemic blood to brain. Many drugs that have a larger size or higher hydrophobicity show promising results in animal studies for treating CNS disorders.

Therefore, a "peptide capable of crossing the blood-brain barrier" will be a peptide capable of transporting itself as well as any molecule it is bound to, preferably a protein, from the blood torrent to the CNS.

In 1983 it was reported that a peptide, β-Casomorphin-5 could overcome the BBB [Ermisch, A. et al. 1983. J. of Neurochemistry. 41:1229-1233]. Since then, many other peptides with BBB-permeating properties have been identified, characterized and catalogued, and in 2012 a comprehensive database was established, as reported by Van Dorpe et al. [Van Dorpe, S. et al. 2012. Brain Struct. Funct. 217:687-718]. Most of the peptides listed in the aforementioned database are suitable for the fusion protein of the invention.

In an embodiment of the invention, the polycationic peptide of the invention is a peptide capable of crossing the blood-brain barrier. In a preferred embodiment of the invention, the peptide capable of crossing the blood-brain barrier is a selected from the group consisting of Seq-1-7 (SEQ ID NO: 17), Seq-1-8 (SEQ ID NO: 18), and Angiopep-2-7 (SEQ ID NO: 19).

(vi) Cell Penetrating Peptide (CPP)

The terms "cell-penetrating peptide" (CPP) refers to a peptide, typically of about 5-60 amino acid residues in length, that can facilitate cellular uptake of molecular cargo, particularly proteins they are a part of Proteins can present one or more CPPs. CPPs can also be characterized as being able to facilitate the movement or traversal of molecular cargo across/through one or more of a lipid bilayer, cell membrane, organelle membrane, vesicle membrane, or cell wall. A CPP herein will be polycationic.

Examples of CPPs useful herein, and further description of CPPs in general, are disclosed in Schmidt et al. [2010. FEBS Lett. 584:1806-1813], Holm et al. [2006. Nature Protocols 1:1001-1005], Yandek et al, [2007. Biophys. J. 92:2434-2444], Morris et al. [2001. Nat. Biotechnol. 19:1173-1176]. and U.S. Patent Application Publication No. 2014/0068797. CPPs do not depend on transporters or receptors, facilitating the traffic of the proteins they are part of directly through the lipid bilayer without the need of participation by any other cell components.

(vii) Nucleolin-Binding Peptide

Accordingly, a "nucleolin-binding peptide" is a peptide capable of binding to the nucleolin protein in a cell, preferably to the cell-surface expressed fraction of nucleolin. In an embodiment of the invention, the polycationic peptide of the invention is a nucleolin-binding peptide.

The International Patent Application Publication with number WO 2011/031477 A2 offers numerous examples of nucleolin-binding peptides that would be suitable for use in the fusion protein of the invention.

In a preferred embodiment of the invention, the nucleolin-binding peptide of the invention is the peptide of sequence SEQ ID NO: 20 or the peptide of sequence SEQ ID NO: 21.

B. Positively Charged Amino Acid-Rich Region

The term "positively charged amino acid" or "second positively charged amino acid-rich region" as used herein, refers to a polypeptide sequence, different from the polycationic region or first positively charged amino acid-rich region characterized in that it contains multiple positively charged amino acids. In addition, the positively charged amino acid-rich region may be formed exclusively by positively charged amino acids or may contain other amino acids provided that the overall net charge of the region at pH 7 is positive. Thus, the positively charged amino acid-rich region sequence may comprise 33%, preferably 40%, preferably 45%, preferably 50%, preferably 55%, preferably 60%, preferably 65%, preferably 70%, preferably 75%, preferably 80%, preferably 85%, more preferably 90%, more preferably 95%, even more preferably 99%, yet even more preferably 100% of the amino acid residues of its complete sequence as positively charged amino acids residues.

The positively charged amino acid-rich region may contain only one type of positively charged amino acid or may contain more than one type of positively charged amino acid. In one embodiment, the positively charged amino acid-rich region is a polyhistidine region. In one embodiment, the positively charged amino acid-rich region is a polyarginine region. In one embodiment, the positively charged amino acid-rich region is a polyhistidine region. In one embodiment, the positively charged amino acid-rich region comprises lysine and arginine residues. In one embodiment, the positively charged amino acid-rich region comprises lysine and histidine residues. In one embodiment, the positively charged amino acid-rich region comprises arginine and histidine residues. In one embodiment, the positively charged amino acid-rich region comprises lysine, arginine and histidine residues In some embodiments, the positively charged amino acid-rich region comprises at least 2, at least 3, at least 4, at least 5, at least 6, at least 7, at least 8, at least 9, at least 10, at least 11, at least 12, at least 13, at least 14, or at least 15 positively charged amino acids residues, wherein the positively charged amino acid can be histidine, lysine, arginine or combinations thereof.

In some embodiments, the positively charged amino acid-rich region comprises fewer than 100, fewer than 90, fewer than 80, fewer than 70, fewer than 60, fewer than 50, fewer than 40, fewer than 30, fewer than 29, fewer than 28, fewer than 27, fewer than 26, fewer than 25, fewer than 24, fewer than 23, fewer than 22, fewer than 21, fewer than 20, fewer than 19, fewer than 18, fewer than 17, fewer than 16, fewer than 15, fewer than 14, fewer than 13, fewer than 12, fewer than 11, fewer than 10 or less positively charged amino acids residues, wherein the positively charged amino acid can be histidine, lysine, arginine or combinations thereof.

In some embodiments, the positively charged amino acid-rich region comprises between 2 and 50 amino acids, between 2 and 40 amino acids, between 2 and 30 amino acids, between 2 and 25 amino acids, between 2 and 20 amino acids, between 2 and 10 amino acids or between 2 and 8 amino acids.

In some embodiments, the positively charged amino acid-rich region comprises between 3 and 50 amino acids, between 3 and 40 amino acids, between 3 and 30 amino acids, between 3 and 25 amino acids, between 3 and 20 amino acids, between 3 and 10 amino acids or between 3 and 8 amino acids. In some embodiments, the positively charged amino acid-rich region comprises between 4 and 50 amino acids, between 4 and 40 amino acids, between 4 and 30 amino acids, between 4 and 25 amino acids, between 4 and 20 amino acids, between 4 and 10 amino acids or between 4 and 8 amino acids. In some embodiments, the positively charged amino acid-rich region comprises between 5 and 50 amino acids, between 5 and 40 amino acids, between 5 and 30 amino acids, between 5 and 25 amino acids, between 5 and 20 amino acids, between 5 and 10 amino acids or between 5 and 8 amino acids.

In an embodiment of the invention, the positively charged amino acid-rich region of the fusion protein of the invention is a polyhistidine region. In a preferred embodiment of the invention, the polyhistidine region comprises between 2 and 10 contiguous histidine residues.

In an embodiment of the invention, the positively charged amino acid-rich region of the fusion protein of the invention is a polyarginine region. In a preferred embodiment of the invention, the polyarginine region comprises between 2 and 10 contiguous arginine residues.

In an embodiment of the invention, the positively charged amino acid-rich region of the fusion protein of the invention is a polylysine region. In a preferred embodiment of the invention, the polylysine region comprises between 2 and 10 contiguous polylysine residues.

C. Relative Positions of the Elements of the Fusion Proteins and Linking Elements The different elements of the fusion protein (polycationic peptide, intervening polypeptide region, and positively charged amino acid-rich region) of the invention can be placed in any relative order provided that the polycationic peptide and the positively charged amino acid-rich region are functional on any position of the fusion protein and also the intervening polypeptide region remains functional totally or in part.

As used herein, the terms "N-terminal end", "N-terminus", and "amino-terminal end" of a polypeptide are indistinct. Equally, the terms "C-terminal end", "C-terminus", and "carboxi-terminal end" are considered equivalent. The terms are of common usage for the person skilled in the art regarding the free moieties of the amino acids at the ends of the polypeptide chains comprised by a protein.

Thus, in an embodiment of the invention, the polycationic peptide of the fusion protein is located at the N-terminal end of the protein, while the positively charged amino acid-rich region of the fusion protein is located at the C-terminal end of the protein. In another embodiment of the invention, the positively charged amino acid-rich region of the fusion protein is located at the N-terminal end of the protein, while the polycationic peptide of the fusion protein is located at the C-terminal end of the protein. In another embodiment of the invention, the intervening polypeptide region can be located at either the C-terminal end or the N-terminal end of the fusion protein, while the polycationic peptide is in the middle position of the fusion protein and the positively charged amino acid-rich region is at the end of the fusion protein opposite the Intervening polypeptide region, or the positively charged amino acid-rich region is in the middle position of the fusion protein and the polycationic peptide is located at the end of the fusion protein opposite the Intervening polypeptide region.

Accordingly, the relative order of the elements of the fusion protein according to the invention, can be:

N-Polycationic peptide-Intervening region polypeptide-positively charged amino acid-rich region-C;
N-positively charged amino acid-rich region-Intervening region polypeptide-Polycationic peptide-C;
N-Polycationic peptide-positively charged amino acid-rich region-Intervening region polypeptide-C;
N-positively charged amino acid-rich region-Polycationic peptide-Intervening region polypeptide-C;
N-Intervening region polypeptide-Polycationic peptide-positively charged amino acid-rich region-C; or
N-Intervening region polypeptide-positively charged amino acid-rich region-Polycationic peptide-C The terms "N-terminal end" and "C-terminal end" do not mean that the components need to be directly conjugated end-to-end, but that they maintain that relative order of positions regardless of the presence of additional elements at the end of either component or intercalated between them, such as linkers/spacers.

Therefore, the fusion protein of the invention comprises the aforementioned elements ((1) polycationic peptide, (2) intervening polypeptide region, and (3) positively charged amino acid-rich region) and these can be conjugated end-to-end but also may include one or more optional peptide or polypeptide "linkers" or "spacers" intercalated between them, linked, preferably by peptidic bond.

According to the invention, the spacer or linker amino acid sequences can act as a hinge region between components (1) and (2) and (2) and (3), allowing them to move independently from one another while maintaining the three-dimensional form of the individual domains, such that the presence of peptide spacers or linkers does not alter the functionality of any of the components (1), (2) and (3). In this sense, a preferred intermediate amino acid sequence according to the invention would be a hinge region characterized by a structural ductility allowing this movement. In a particular embodiment, said intermediate amino acid sequence is a flexible linker. The effect of the linker region is to provide space between the components (1) and (2) and (2) and (3). It is thus assured that the secondary and tertiary structure of component (1), (2) or (3) is not affected by the presence of either of the others. The spacer is of a polypeptide nature. The linker peptide preferably comprises at least 2 amino acids, at least 3 amino acids, at least 5 amino acids, at least 10 amino acids, at least 15 amino acids, at least 20 amino acids, at least 30 amino acids, at least 40 amino acids, at least 50 amino acids, at least 60 amino acids, at least 70 amino acids, at least 80 amino acids, at least 90 amino acids or approximately 100 amino acids.

The spacer or linker can be bound to components flanking the two components of the conjugates of the invention by means of covalent bonds, preferably by peptide bonds; and also preferably the spacer is essentially afunctional, and/or is not prone to proteolytic cleavage, and/or does not comprise any cysteine residue. Similarly, the three-dimensional structure of the spacer is preferably linear or substantially linear.

The preferred examples of spacer or linker peptides include those that have been used to bind proteins without substantially deteriorating the function of the bound peptides or at least without substantially deteriorating the function of one of the bound peptides. More preferably the spacers or linkers used to bind peptides comprise coiled coil structures.

Preferred examples of linker peptides comprise 2 or more amino acids selected from the group consisting of glycine, serine, alanine and threonine. A preferred example of a flexible linker is a polyglycine linker. The possible examples of linker/spacer sequences include SGGTSGSTSGTGST (SEQ ID NO: 22), AGSSTGSSTGPGSTT (SEQ ID NO: 23) or GGSGGAP (SEQ ID NO: 24). These sequences have been used for binding designed coiled coils to other protein domains [Muller, K. M., Arndt, K. M. and Alber, T., Meth. Enzymology, 2000, 328: 261-281]. Further non-limiting examples of suitable linkers comprise the amino acid sequence GGGVEGGG (SEQ ID NO: 25), the sequence of 10 amino acid residues of the upper hinge region of murine IgG3 (PKPSTPPGSS, SEQ ID NO: 26), which has been used for the production of dimerized antibodies by means of a coiled coil [Pack, P. and Pluckthun, A., 1992, Biochemistry 31:1579-1584], the peptide of sequence APAETKAEPMT (SEQ ID NO: 27), the peptide of sequence GAP, the peptide of sequence AAA and the peptide of sequence AAALE (SEQ ID NO: 46).

Alternatively, the components of the conjugates of the invention can be connected by peptides the sequence of which contains a cleavage target for a protease, thus allowing the separation of any of the components. Protease cleavage sites suitable for their incorporation into the polypeptides of the invention include enterokinase (cleavage site DDDDK, SEQ ID NO: 28), factor Xa (cleavage site IEDGR, SEQ ID NO: 29), thrombin (cleavage site LVPRGS, SEQ ID NO: 30), TEV protease (cleavage site ENLYFQG, SEQ ID NO: 31), PreScission protease (cleavage site LEVLFQGP, SEQ ID NO: 32), inteins and the like.

Thus, in an embodiment of the invention, the polycationic peptide is bound to the intervening polypeptide region through a linker. In another embodiment of the invention, the intervening polypeptide region is bound to the positively charged amino acid-rich region through a linker. In yet another embodiment of the invention, the polycationic peptide is bound to the intervening polypeptide region through a linker and the intervening polypeptide region is bound to the positively charged amino acid-rich region through a linker also.

As the person skilled in the art will acknowledge, the linkers connecting the polycationic peptide to the intervening polypeptide region and the intervening polypeptide region to the positively charged amino acid-rich region may comprise the same sequence or different ones with the aforementioned limitation that the presence and/or sequence of the linkers does not result in functional alterations of the polycationic peptide, the intervening polypeptide region, and/or the positively charged amino acid-rich region (for instance, but not limited to, due to secondary or tertiary structure modifications of the fusion protein or formation of disulfide bonds).

The aforementioned considerations regarding the relative positions from the N-terminal end to the C-terminal end of the elements of the fusion protein apply also in the presence of linkers between them, independently of the number of them or what elements they are placed between. Therefore, the possible combinations and relative orders of elements will be the following (wherein the numbering stated above for the elements is retained: (1) polycationic peptide, (2) intervening polypeptide region, (3) positively charged amino acid-rich region):

N-(1)-(2)-(3)-C
N-(1)-linker-(2)-(3)-C
N-(1)-(2)-linker-(3)-C
N-(1)-linker-(2)-linker-(3)-C
N-(3)-(2)-(1)-C
N-(3)-linker-(2)-(1)-C
N-(3)-(2)-linker-(1)-C
N-(3)-linker-(2)-linker-(3)-C
N-(2)-(1)-(3)-C
N-(2)-linker-(1)-(3)-C
N-(2)-(1)-linker-(3)-C
N-(2)-linker-(1)-linker-(3)-C
N-(2)-(3)-(1)-C
N-(2)-linker-(3)-(1)-C
N-(2)-(3)-linker-(1)-C
N-(2)-linker-(3)-linker-(1)-C
N-(1)-(3)-(2)-C
N-(1)-(3)-linker-(2)-C
N-(1)-linker-(3)-(2)-C
N-(1)-linker-(3)-linker-(2)-C
N-(3)-(1)-(2)-C
N-(3)-linker-(1)-(2)-C
N-(3)-(1)-linker-(2)-C
N-(3)-linker-(1)-linker-(2)-C In a preferred embodiment of the invention, the linkers of the fusion protein of the invention comprise the sequence GGSSRSS (SEQ ID NO: 33) sequence of the GGGNS sequence (SEQ ID NO: 34).

D. Intervening Polypeptide Region

The terms "intervening polypeptide region" and "intervening region" are herein considered equivalent.

The intervening polypeptide region of the fusion proteins of the invention comprises a physiologically functional peptide, meaning that its interaction with the cellular components results in physiological changes. However, the intervening polypeptide region does not need to be physiologically functional once it is incorporated into the fusion protein of the invention. Accordingly, linker regions connecting the different elements of the fusion protein according to the invention are not considered intervening regions. Thus, in preferred embodiments, the intervening region comprises at least 5, at least 10, at least 15, at least 20, at least 25, at least 30, at least 35, at least 40, at least 50, at least 60, at least 70, at least 80, at least 90, at least 100 or more amino acids.

In a preferred embodiment the intervening polypeptide region is a physiologically functional peptide or a fragment or a mutant thereof with a reduced physiological function once it is incorporated into the fusion protein of the invention. In another embodiment, the intervening polypeptide region does not have any physiological function once incorporated into the fusion protein of the invention. In another preferred embodiment, the intervening polypeptide region is a fragment or a mutant of a physiologically functional polypeptide with an already reduced physiological function, as compared to the wild-type physiologically functional polypeptide before being incorporated into the fusion protein of the invention. More preferably, the intervening polypeptide region is a protein which does not have any physiological function already when not forming part of the fusion protein of the invention, due to the presence of inactivating mutations.

The intervening polypeptide region of the fusion proteins of the invention is a protein bound to a therapeutic agent.

The term "therapeutic", as used herein in relation to the therapeutic agents, is used in a generic sense and includes treating agents, prophylactic agents, and replacement agents.

As it is part of the fusion protein of the invention with the polycationic peptide and the positively charged amino acid-rich region, the nature of the intervening region is substantially polypeptidic, except where the therapeutic agent is concerned. It is intended that the therapeutic agent conjugated to the fusion protein is not limited in its chemical structure.

In an embodiment of the invention, the intervening region of the fusion protein is selected from the group consisting of a fluorescent protein, albumin, nidogens, chorionic gonadotropin, and a cystatin.

"Fluorescent protein", as used herein, relates to proteins whose atomic structure allows them to present fluorescence, which is a phenomenon well-known in the art. Non-limiting examples of commonly used fluorescent proteins suitable for the fusion protein of the invention, are the green fluorescent protein (GFP, first discovered in Aequorea victoria), the red fluorescent protein (RFP), the yellow fluorescent protein (YFP), the blue fluorescent protein (BFP), the cyan fluorescent protein, or any other variant, examples of which can be found in Kremers et al. [Kremers, G-J- et al. 2011. J. Cell Sci. 124:157-160].

Additional non-limiting examples of fluorescent proteins suitable for the fusion protein of the invention are the enhanced green fluorescent protein (eGFP), enhanced cyan fluorescent protein CFP (ECFP), enhanced YFP (EYFP), GFPS65T, Emerald, Topaz (TYFP), Venus, Citrine, mCitrine, GFPuv, destabilized EGFP (dEGFP), destabilised ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2 (12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. In other embodiments, the intervening polypeptide is a fluorescent protein selected from the group consisting of the mHoneydew, mBanana, mOrange, dTomato, tdTomato, mTangerine, mStrawberry, mCherry, mGrapel, mRaspberry, mGrape2, mPlum [Shaner et al. (2005) Nat. Methods 2:905-909], and the like.

In a preferred embodiment, the fluorescent protein of the intervening region of the fusion protein of the invention is GFP (SEQ ID NO: 35).

"Albumin", as used herein, refers to the water-soluble, non-glycosylated globular proteins commonly found in the plasma of animals, especially mammals. In a preferred embodiment, the protein of the intervening region of the fusion protein is albumin, more preferably human albumin (SEQ ID NO: 36).

"Nidogen", as used herein, relates to any protein of the family of nidogens, formerly known as entactins, which are sulfated monomeric glycoproteins located in the basal lamina.

In a more preferred embodiment of the invention, the protein of the intervening region of the fusion protein is selected from the group consisting of the human nidogen 1 (NID1, SEQ ID NO: 37) and the human nidogen 2 (NID2, SEQ ID NO: 38).

"Chorionic gonadotropin" (GC), as used herein, refers to the glycoprotein and hormone produced in the placenta of mammals after the zygote implantation. Human chorionic gonadotropin presents two subunits, alpha (α) and beta (β). It is intended that any one of the two subunits separately and both together are suitable for the purposes of the invention.

Thus, in another embodiment of the invention, the protein of the intervening region of the fusion protein is the chorionic gonadotropin.

In another preferred embodiment of the invention, the protein of the intervening region of the fusion protein is the human chorionic gonadotropin (hGC, SEQ ID NO: 39).

As used herein, the term cystatin refers to a member of a family of protease inhibitors known as cystatins which are capable of inhibiting the activity of peptidase enzymes belonging to peptidase families C1 (papain family) and C13 (legumain family). In a preferred embodiment, the cystatin is selected from the group consisting of cystatin A, cystatin B, cystatin C, cystatin D and cystatin M. In yet another preferred embodiment, the cystatin is a cystatin A, also known as Stefin A. In a preferred embodiment, Stefin A is of human origin having the sequence SEQ ID NO:40. In yet another embodiment, the cystatin is a stefin A variant having one or more mutations selected from the group consisting of the G4W, the G4R, the V48D, the V48L, the G50S, the K71N, the S72G, the L73P, the L82R, the T83S mutations. In other embodiments, the stefin A variant contains the following mutations with respect to the sequence shown in SEQ ID NO:40:

G4W, V48D, K71N, S72G and L73P, corresponding to the mutant defined as STM mutant in Woodward et al. (J. Mol. Biol. (2005) 352, 1118-1133) and in Hoffman et al., Protein Engineering, Design & Selection vol. 23 no. 5 pp. 403-413, 2010).

G4R, V48L, G50S, K71N, S72G, L73P, L82R and T83S, corresponding to the mutant defined as SQM mutant in Hoffman et al., supra.) and in.

G4R corresponding to the mutant defined as SUN mutant in Hoffman et al., supra.).

V48L and G50S corresponding to the mutant defined as SUM mutant in Hoffman et al., supra.).

K71N, S72G, L73P, L82R and T83S corresponding to the mutant defined as SUC mutant in Hoffman et al., supra.).

V48L, G50S, K71N, S72G, L73P, L82R and T83S, corresponding to the mutant defined as SDM mutant in Hoffman et al., supra.).

Other suitable polypeptides and proteins that can be used as components of the intervening region include any polypeptide or protein without any physiological or biological activity on their own, as well as any biologically non-reactive peptide or protein.

In another embodiment of the invention the protein of the intervening region of the fusion protein is an inert protein.

As used herein, "Inert protein" refers to polypeptides or proteins or fragments or domains of proteins without known physiological or biological activity, or without the ability to specifically interact with other macromolecules for a biological function, and fragments or domains of proteins devoid of known therapeutic activity (e.g. antitumor activity). The inert protein that is part of the fusion protein is non-reactive and functions as a physical structure for the binding of the therapeutic agents. It is intended that the inert proteins do not comprise any motifs that have intrinsic enzymatic, physiological, or biological activity on their own, nor do they present immune reactivity, meaning that they stimulate neither the adaptive, nor the innate immune responses.

In general, wherein the protein of the intervening region of the fusion protein is concerned, it is intended that any intrinsic activity of said protein is irrelevant for the purposes of the invention and does neither contribute, nor hinder the biological activity of the therapeutic agent.

In a particular embodiment, the intervening polypeptide of the fusion proteins of the invention is a fragment of any of the proteins described in any of the embodiments of this section D.

In another preferred embodiment, the intervening polypeptide of the fusion protein of the invention is a mutant of any of the proteins described in any of the embodiments of this section D.

E. The Therapeutic Agent

The term "therapeutic agent", as used herein, is drawn to any compound, without chemical structure limitations, suitable for therapy and/or treatment of a condition, disorder or disease.

The nature of the therapeutic agent is not particularly limiting for the present invention provided it remains active in the fusion protein or can be activated once it is delivered to the inside of the cell. Accordingly, any therapeutic agent can be used in the fusion protein provided that it shows an activity or can reach an activity once it is delivered to the inside of the cell of at least 100%, at least 90%, at least 80%, at least 70%, at least 60%, at least 50% or less of the activity of the unconjugated therapeutic agent. Alternatively, since the purpose of the invention is to facilitate the action of the therapeutic agent by increasing its selectivity and reducing its off-target effects, it is contemplated that the effects of the therapeutic agent conjugated to the fusion protein may be synergic and exceed the parametrized values already known for the specific therapeutic agent. Accordingly, it is intended that some embodiments of the therapeutic agent conjugated to the fusion protein of the invention also show at least 101%, at least 105%, at least 110%, at least 115%, at least 120%, at least 125%, at least 130%, at least 135%, at least 140%, at least 145%, at least 150%, at least 175%, at least 200%, at least 300%, at least 400%, at least 500%, at least 1000%, or more of the functionality of the therapeutic agent alone.

In an embodiment of the invention, the therapeutic agent of the intervening region of the fusion protein of the invention is selected from the group consisting of
(i) a chemotherapy agent,
(ii) a cytotoxic polypeptide,
(ii) an antiangiogenic polypeptide,
(iii) a polypeptide encoded by a tumor suppressor gene,
(iv) a pro-apoptotic polypeptide,
(v) a polypeptide having anti-metastatic activity,
(vi) a polypeptide encoded by a polynucleotide which is capable of activating the immune response towards a tumor,
(vii) an antiangiogenic molecule, and
(viii) a toxin.

(i) Chemotherapy Agent

It will be understood that the term "chemotherapeutic agents" refers to anti-cancer agents. As used herein, an anti-cancer agent is an agent that at least partially inhibits the development or progression of a cancer, including inhibiting in whole or in part symptoms associated with the cancer even if only for the short term.

Several anti-cancer agents can be categorized as DNA damaging agents and these include topoisomerase inhibitors (e.g., etoposide, ramptothecin, topotecan, teniposide, mitoxantrone), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), anthracyclines, vinca alkaloids, or epipodophyllotoxins.

Additional examples of anti-cancer agents include without limitation Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE); Brequinar Sodium; Bropirimine; Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE); Doxorubicin; Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA), Esorubicin; Estramustine; Etanidazole; Etoposide; Etoprine; Fadrozole; Fazarabine; Fenretinide; Floxuridine; Fludarabine; 5-Fluorouracil; Flurocitabine; Fosquidone; Fostriecin; Gefitinib (IRES SA), Gemcitabine; Hydroxyurea; Idarubicin; Ifosfamide; Ilmofosine; Imatinib mesylate (GLEEVAC); Interferon alpha-2a; Interferon alpha-2b; Interferon alpha-nl; Interferon alpha-n3; Interferon beta-I a; Interferon gamma-I b; Iproplatin; Irinotecan; Lanreotide; Lenalidomide (REVLLM1D, REVIMID); Letrozole; Leuprolide; Liarozole; Lometrexol; Lomustine; Losoxantrone; Masoprocol; Maytansine; Mechlorethamine; Megestrol; Melengestrol; Melphalan; Menogaril; Mercaptopurine; Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemetrexed (ALIMTA), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR); Teniposide; Teroxirone; Testolactone; Thalidomide (THALOMID) and derivatives thereof; Thiamiprine; Thioguanine; Thiotepa; Tiazofurin; Tirapazamine; Topotecan; Toremifene; Trestolone; Triciribine; Trimetrexate; Triptorelin; Tubulozole; Uracil; Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

In one embodiment, the anti-cancer agent is provided as an oligomer containing several units of the anti-cancer molecule. In one embodiment, the anti-cancer agent is a floxuridin poly- or oligonucleotide, which comprises several floxuridine molecules. The floxuridine poly- or poligonucleotide contains at least 2, 3, 4, 5, 6, 7, 8, 9, 10, 15, 20, 25, 30, 35, 40, 45, 50 or more floxuridine molecules. In a preferred embodiment the floxuridine polynucleotide is a floxuridine pentanucleotide, i.e. a oligonucleotide containing 5 floxuridine molecules.

The anti-cancer agent may be an enzyme inhibitor including without limitation tyrosine kinase inhibitor, a CDK inhibitor, a MAP kinase inhibitor, or an EGFR inhibitor. The tyrosine kinase inhibitor may be without limitation Genistein (4', 5, 7-trihydroxyisoflavone), Tyrphostin 25 (3,4, 5-trihydroxyphenyl), methylene]-propanedinitrile, Herbimycin A, Daidzein (4',7-dihydroxyisoflavone), AG-126, trans-1-(3'-carboxy-4'-hydroxyphenyl)-2-(2",5"-dihydroxyphenyl)ethane, or HDBA (2-Hydroxy5-(2,5-Dihydroxybenzylamino)-2-hydroxybenzoic acid. The CDK inhibitor may be without limitation p21, p27, p57, p15, p16, p18, or p19. The MAP kinase inhibitor may be without limitation KY12420 (C23H24O8), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA), gefitinib (IRESSA), WHI-P97 (quinazoline derivative), LFM-A12 (leflunomide metabolite analog), ABX-EGF, lapatinib, canertinib, ZD-6474 (ZACTIMA), AEE788, and AG1458.

The anti-cancer agent may be a VEGF inhibitor including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin. The anti-cancer agent may be an antibody or an antibody fragment including without limitation an antibody or an antibody fragment including but not limited to bevacizumab (AVASTIN), trastuzumab (HERCEPTIN), alemtuzumab (CAMPATH, indicated for B cell chronic lymphocytic leukemia), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), I0R-C5, 10R-T6 (anti-CD 1), IOR EGF/R3, celogovab (ONCOSCINT OV 103), epratuzumab (LYMPHOCIDE), pemtumomab (THERAGYN), and Gliomab-H (indicated for brain cancer, melanoma).

It is contemplated that in certain embodiments of the invention a protein that acts as an angiogenesis inhibitor is targeted to a tumor. These agents include, in addition to the anti-angiogenic polypeptides mentioned above, Marimastat; AG3340; COL-3, BMS-275291, Thalidomide, Endostatin, SU5416, SU6668, EMD121974, 2-methoxyoestradiol, carboxiamidotriazole, CMlOl, pentosan polysulphate, angiopoietin 2 (Regeneron), herbimycin A, PNU145156E, 16K prolactin fragment, Linomide, thalidomide, pentoxifylline, genistein, TNP470, endostatin, paclitaxel, accutin, angiostatin, cidofovir, vincristine, bleomycin, AGM-1470, platelet factor 4 or minocycline.

Other suitable active agents are DNA cleaving agents. Examples of DNA cleaving agents suitable for inclusion as the cell toxin in the conjugates used in practicing the methods include, but are not limited to, anthraquinone-oligopyrrol-carboxamide, benzimidazole, leinamycin; dynemycin A; enediyne; as well as biologically active analogs or derivatives thereof (i.e., those having a substantially equivalent biological activity). Known analogs and derivatives are disclosed, for examples in Islam et al., J. Med. Chem. 34 2954-61, 1991; Skibo et al., J. Med. Chem. 37:78-92, 1994; Behroozi et al., Biochemistry 35:1568-74, 1996; Helissey et al., Anticancer Drug Res. 11:527-51, 1996; Unno et al., Chem. Pharm. Bull. 45:125-33, 1997; Unno et al., Bioorg. Med. Chem., 5:903-19, 1997; Unno et al., Bioorg. Med. Chem., 5: 883-901, 1997; and Xu et al., Biochemistry 37:1890-7, 1998). Other examples include, but are not limited to, endiyne quinone imines (U.S. Pat. No. 5,622, 958); 2,2r-bis (2-aminoethyl)-4-4'-bithiazole [Lee et al., Biochem. Mol. Biol. Int. 40:151-7, 1996]; epilliticine-salen-.copper conjugates [Routier et al., Bioconjug. Chem., 8: 789-92, 1997].

Some of the aforementioned chemotherapy agents can be grouped together under a common category as antimetabolites. "Antimetabolite" as used herein, refers to the compounds which inhibit the use of a metabolite that is part of normal metabolism. Antimetabolites are often similar in structure to the metabolite that they interfere with, such as the antifolates that interfere with the use of folic acid. Non-limiting examples of antimetabolites include the following compounds: bleomycin, busulfan, capecitabine, carmustine, carboplatin, chlorodeoxyadenosine, cisplatin, cyclophosphamide, cytarabine, dacarbazine, daunorubicin, docetaxel, doxorubicin, etoposide, fludarabine, fluorouracil, gemcitabine, hydroxyurea, idarubicin, ifosfamide, irinotecan, lomustine, melphalan, mercaptopurine, methotrexate mitomycin, mitoxantrone, oxaliplatin, paclitaxel, procarbazine, SN-38, thioguanine, thiotepa, teniposide vinblastine, vincristine, and vinorelbine.

(ii) Cytotoxic Polypeptides

As used herein, the term "cytotoxic polypeptide" refers to an agent that is capable of inhibiting cell function. The agent may inhibit proliferation or may be toxic to cells. Any polypeptides that when internalized by a cell interfere with or detrimentally alter cellular metabolism or in any manner inhibit cell growth or proliferation are included within the ambit of this term, including, but not limited to, agents whose toxic effects are mediated when transported into the cell and also those whose toxic effects are mediated at the cell surface. Useful cytotoxic polypeptides include proteinaceous toxins such as bacterial toxins.

Examples of proteinaceous cell toxins useful for incorporation into the conjugates according to the invention include, but are not limited to, type one and type two ribosome inactivating proteins (RIP). Useful type one plant RIPs include, but are not limited to, dianthin 30, dianthin 32, lychnin, saporins 1-9, pokeweed activated protein (PAP), PAP II, PAP-R, PAP-S, PAP-C, mapalmin, dodecandrin, bryodin-L, bryodin, Colicin 1 and 2, luffin-A, luffin-B, luffin-S, 19K-protein synthesis inhibitory protein (PSI), 15K-PSI, 9K-PSI, alpha-kirilowin, beta-kirilowin, gelonin, momordin, momordin-II, momordin-Ic, MAP-30, alpha-momorcharin, beta-momorcharin, trichosanthin, TAP-29, trichokirin; barley RIP; flax RIP, tritin, corn RIP, Asparin 1 and 2 [Stirpe et al., 1992. Bio/Technology 10:405-12]. Useful type two RIPs include, but are not limited to, volkensin, ricin, nigrin-b, CIP-29, abrin, modeccin, ebulitin-[alpha], ebulitin-[beta], ebultin-[gamma], vircumin, porrectin, as well as the biologically active enzymatic subunits thereof [Stirpe et al., 1992. Bio/Technology 10:405-12; Pastan et al., 1992. Annu. Rev. Biochem. 61:331-54; Brinkmann and Pastan, 1994. Biochim. et Biophys. Acta 1198: 27-45; and Sandvig and Van Deurs, 1996. Physiol. Rev. 76:949-66].

Examples of bacterial toxins useful as cell toxins include, but are not limited to, shiga toxin and shiga-like toxins (i.e., toxins that have the same activity or structure), as well as the catalytic subunits and biologically functional fragments thereof. These bacterial toxins are also type two RIPs [Sandvig and Van Deurs, 1996. Physiol. Rev. 76:949-66; Armstrong, 1995. J. Infect. Dis., 171:1042-5; Kim et al., 1997. Microbiol. Immunol. 41:805-8; and Skinner et al., 1998. Microb. Pathog. 24:117-22]. Additional examples of useful bacterial toxins include, but are not limited to, *Pseudomonas* exotoxin and Diphtheria toxin [Pastan et al., 1992. Annu. Rev. Biochem. 61:331-54; and Brinkmann and Pastan, 1994. Biochim. et Biophys. Acta 1198:27-45]. Truncated forms and mutants of the toxin enzymatic subunits also can be used as a cell toxin moiety (Pastan et al., Annu. Rev. Biochem. 61:331-54; Brinkmann and Pastan, Biochim. et Biophys. Acta 1198:27-45, 1994; Mesri et al., J. Biol. Chem. 268:4852-62, 1993; Skinner et al., Microb. Pathog. 24:117-22, 1998; and U.S. Pat. No. 5,082,927). Other targeted agents include, but are not limited to the more than 34 described Colicin family of RNase toxins which include colicins A, B, D, E1-9, cloacin DF13 and the fungal RNase, [alpha]-sarcin [Ogawa et al. 1999. Science 283: 2097-100, Smarda et al., 1998. Folia Microbiol (Praha) 43:563-82; Wool et al., 1992. Trends Biochem. Sci., 17: 266-69].

(iii) Antiangiogenic Polypeptides

Proliferation of tumor cells relies heavily on extensive tumor vascularization, which accompanies cancer progression. Thus, inhibition of new blood vessel formation with anti-angiogenic agents and targeted destruction of existing blood vessels have been introduced as effective and relatively non-toxic approaches to tumor treatment.

The term "anti-angiogenic polypeptide", as used herein, denotes a polypeptide capable of inhibiting angiogenesis. Suitable antiangiogenic polypeptides include, without limitation, angiostatin, endostatin, anti-angiogenic anti-thrombin III, sFRP-4 as described in WO2007115376, and an anti-VEGF antibody such as anibizumab, bevacizumab (avastin), Fab IMC 1121 and F200 Fab.

(iv) Polypeptides Encoded by a Tumor Suppressor Gene

As used herein, a "tumor suppressor" is a gene or gene product that has a normal biological role of restraining unregulated growth of a cell. The functional counterpart to a tumor suppressor is an oncogene—genes that promote normal cell growth may be known as "proto-oncogenes" A mutation that activates such a gene or gene product further converts it to an "oncogene", which continues the cell growth activity, but in a dysregulated manner Examples of tumor suppressor genes and gene products are well known in the literature and may include PTC, BRCA1, BRCA2, p16, APC, RB, WT1, EXT1, p53, NF1, TSC2, NF2, VHL, ST7, ST14, PTEN, APC, CD95 or SPARC.

(v) Pro-Apoptotic Polypeptides

The term "pro-apoptotic polypeptides", as used herein, refers to a protein which is capable of inducing cell death in a cell or cell population. The overexpression of these proteins involved in apoptosis displaces the careful balance between anti-apoptotic and pro-apoptotic factors towards an apoptotic outcome. Suitable pro-apoptotic polypeptides include, without limitation, pro-apoptotic members of the BCL-2 family of proteins such as BAX, BAK, BOK/MTD, BID, BAD, BIK/NBK, BLK, HRK, BIM/BOD, BNIP3, NIX, NOXA, PUMA, BMF, EGL-I, and viral homologs, caspases such as caspase-8, the adenovirus E4orf4 gene, p53 pathway genes, pro-apoptotic ligands such as TNF, FasL, TRAIL and/or their receptors, such as TNFR, Fas, TRAIL-R1 and TRAIL-R2.

(vi) Polypeptides with Anti-Metastatic Activity

The term "metastasis suppressor" as used herein, refers to a protein that acts to slow or prevent metastases (secondary tumors) from spreading in the body of an organism with cancer. Suitable metastasis suppressor include, without limitation, proteins such as BRMS 1, CRSP3, DRG1, KAI1, KISS-1, NM23, a TIMP-family protein and uteroglobin.

(vii) Polypeptides Encoded by a Polynucleotide Capable of Activating the Immune Response Towards a Tumor As used herein, an immunostimulatory polypeptide agent is a polypeptide encoded by a polynucleotide which is capable of activating or stimulating the immune response (including enhancing a pre-existing immune response) in a subject to whom it is administered, whether alone or in combination with another agent. Suitable non-limiting examples of immunostimulatory peptides include flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), immunostimulatory antibodies (e.g., anti-CTLA-4, anti-CD28, anti-CD3, or single chain/antibody fragments of these molecules), and the like.

(viii) Antiangiogenic Molecules

It is also contemplated that in certain embodiments the intervening region of the fusion protein of the invention corresponds to a protein that acts as an angiogenesis inhibitor is targeted to a tumor. These agents include, in addition to the anti-angiogenic polypeptides mentioned above, Marimastat; AG3340; COL-3, BMS-275291, Thalidomide, Endostatin, SU5416, SU6668, EMD121974, 2-methoxyoestradiol, carboxiamidotriazole, CMIOl, pentosan polysulphate, angiopoietin 2 (Regeneron), herbimycin A, PNU145156E, 16K prolactin fragment, Linomide, thalidomide, pentoxifylline, genistein, TNP470, endostatin, paclitaxel, accutin, angiostatin, cidofovir, vincristine, bleomycin, AGM-1470, platelet factor 4 or minocycline. Also included are VEGF inhibitors including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin.

(ix) Toxins

As used herein, the term "toxins" refers to non-proteinaceous/non-polypeptidic cytotoxic compounds obtained from different organisms, as well as chemically modified derivatives of those same compounds and compounds obtained through chemical synthesis. The compounds of this category with biological origin may be obtained from microorganisms (whether bacteria, archaea, protozoa or unicellular fungi) or pluricellular organisms (pluricellular fungi, plants, or animals, like mollusks). It is intended that the chemical composition and structure of these toxins is not limited in any way beyond their non-polypeptidic nature, therefore one or more amino acids may be part of their structure, whether as part of their basic composition or as result of chemical derivation, as long as all the amino acids participating in the structure are not bound together by peptide bonds.

Examples of toxins suitable for the invention are calicheamycin γ1, dolastatin 10, maytansinoid (DM1) and pyrolobenzodiazepine dimer (PBD).

F. Linkage of the Therapeutic Agent to the Intervening Region

The therapeutic agent of the invention is conjugated to the fusion protein of the invention. It is intended that the therapeutic agent, as aforementioned, is conjugated to the intervening region of the fusion protein without limitation of the position of the conjugation inside the intervening region with regards to the N-terminal and C-terminal ends. Accordingly, the therapeutic agent can be conjugated to the intervening polypeptide region in an equidistant position with respect to the N-terminal and C-terminal ends or it can be closer to either of them. Hence, the therapeutic agent can be conjugated to the intervening polypeptide region at a distance of 100, 90, 80, 75, 70, 65, 60, 55, 50, 45, 40, 35, 30, 25, 30, 25, 20, 15, 20, 10, or less amino acid residues from the N-terminal or C-terminal end, or at the same residue of the N-terminal or C-terminal end.

The only intended limitation in the conjugation position of the therapeutic agent is that the therapeutic agent and the elements of the fusion protein are functional and the conjugation of the therapeutic agent does not interfere with the activity of either therapeutic agent or the fusion protein. So, the therapeutic agent, the polycationic peptide, and the positively charged amino acid-rich region conserve at least 45%, at least 50%, at least 55%, at least 60%, at least 65%, at least 70%, at least 75%, at least 80%, at least 85%, at least 90%, preferably 95%, more preferably 99%, even more preferably 100% of their functionality with respect to the non-conjugated forms of the fusion protein and the therapeutic agent respectively.

It is intended that the therapeutic agent can either be conjugated directly to a residue of the intervening polypeptide of the fusion protein or its bond may be mediated by a linking moiety. "Linking moiety" as used herein, relates to a molecule connecting the therapeutic peptide to the intervening region of the fusion protein. It is also intended that the linking moiety is not limited in its chemical nature and/or structure; therefore, the linking moiety may be a polysaccharide, a polypeptide, a fatty acid, a phospholipid, or a chemical derivative thereof, among others. It is further intended that the therapeutic agent may be bound to the linking moiety through any chemical bond, such as peptide bond, isopeptide bond, amide bond, imine bond, and etcetera.

The person skilled in the art will acknowledge that the previous provisions regarding the functionality of the elements of the fusion protein and the therapeutic agent apply also whenever a coupler mediates the conjugation between the therapeutic agent and the fusion protein. Therefore, whenever the therapeutic agent is conjugated to the fusion protein through a linking moiety, the therapeutic agent, the polycationic peptide, and the positively charged amino acid-rich region conserve at least 45%, at least 50%, at least 55%, at least 60%, at least 65%, at least 70%, at least 75%, at least 80%, at least 85%, at least 90%, preferably 95%, more preferably 99%, even more preferably 100% of their functionality with respect to the non-conjugated forms of the fusion protein and the therapeutic agent respectively, regardless of the position of the conjugation in the intervening region, the chemical composition or structure of the linking moiety and the chemical nature of the bond/s between the linking moiety and the therapeutic agent and between the linking moiety and the intervening region.

Thus, in an embodiment of the invention, the therapeutic agent is bound to the intervening polypeptide region of the fusion protein directly.

In another embodiment of the invention, the therapeutic agent is bound to the intervening region of the fusion protein though a linking moiety.

In a preferred embodiment of the invention, the linking moiety that mediates the bond of the therapeutic agent to the intervening region of the fusion protein through is 6-Maleimidohexanoic acid N-hydroxysuccinimide ester. In another preferred embodiment, the linking moiety that mediates the bond of the therapeutic agent to the intervening region of the fusion protein through is 4-Maleimido hexanoic acid N-hydroxysuccinimide ester.

In some embodiments of the invention, the linking moiety binding the therapeutic agent to the intervening region of the fusion protein is susceptible to be processed by enzymes present in the cytoplasm, releasing the therapeutic agent from the fusion protein once the therapy agent conjugated to the fusion protein has been internalized in a cell.

As the person skilled in the art will recognize, the numerous residues of the polypeptidic chain of the intervening region of the fusion protein offer not only multiple positions wherein a therapeutic agent can be bound or linked but also the possibility of linking more than one molecule of the same or different therapeutic agents to the same fusion protein. As previously, it is intended that the provisions regarding the functionality of the elements of the fusion protein as well as the therapeutic agent/s are upheld and that the increase of the number of molecules of the same or of a different therapeutic agent, the binding of different therapeutic agents, their chemical nature, or their binding positions do not affect the effectiveness and functionality of each therapeutic agent.

Besides, some therapeutic agents may be polymerized in such a way that multiple copies of the same molecule may be bound together like polymers of analogs of nucleotides can oligonucleotides, for instance 5-Fluoro-2'-deoxyUridine (FdU), which result in oligo-FdU. It is intended that some embodiments of the invention may comprise such polymers. Also, it is intended that some other embodiments of the invention may comprise polymers of 2 or more different molecules of therapeutic agents provided that the therapeutic agents do not interfere with the physiological or biological effects of each other. The person skilled in the art will recognize that those embodiments of the invention featuring polymers of therapeutic agents may feature 2, 3, 4, 5, 6, 7, 8, 9, 10, 15, 20, 15, 30, 40, 50 or more molecules polymerized together of 1 or more different therapeutic agents in a proportion of 1:1, 1:2, 1:3, 1:4, 1:5, 1:6, 1:7, 1:8, 1:9, 1:10, or more.

Thus, in another embodiment of the invention, the intervening polypeptide of the fusion protein is conjugated to a plurality of therapeutic agents, wherein said plurality of therapeutic agents are the same or different.

In a preferred embodiment of the invention, the therapeutic agent conjugated to the intervening polypeptide region of the fusion protein is a chemotherapy agent.

In a more preferred embodiment of the invention, the chemotherapy agent conjugated to the intervening region of the fusion protein is an antimetabolite.

In an even more preferred embodiment of the invention, the chemotherapy agent conjugated to the intervening region of the fusion protein is an antimetabolite.

In an even yet more preferred embodiment of the invention, the antimetabolite conjugated to the intervening region of the fusion protein is a pyrimidine analogue or an oligomeric form thereof.

In a most preferred embodiment of the invention, the pyrimidine analogue conjugated to the intervening region of the fusion protein is floxuridine.

G. Reporter Proteins

In another embodiment of the invention, the fusion protein of the invention further comprises a reporter protein.

The person skilled in the art will acknowledge the term "reporter protein" as referring to a protein resulting from the expression of a "reporter gene". Reporter proteins are well known and commonly used in the art as markers suitable for multiple purposes, such as location of the expression of the reporter genes in tissues, cells or subcellular locations, protein-protein interactions, transport across the plasmatic membranes or endomembranes, vesicular traffic, ligand-receptor interactions, etcetera.

Useful reporter proteins in the context of the present invention include luciferase-4-monooxygenase from *Photinus pyralis*, β-galactosidase, thymidine kinase, and the like. The reporter proteins also include fluorescent proteins, which have already been discussed.

The reporter protein comprised by the fusion protein of the invention is directly adjacent to the positively charged amino acid-rich region or separated by a linker. The relative position of the positively charged amino acid-rich region, however, remains as per the the aforementioned considerations about the relative position of the elements of the fusion protein. Hence, independently of the position of the fusion protein, the fluorescent protein is always adjacent to it, either directly or separated by a linker.

Accordingly, in the embodiments of the invention comprising a fluorescent protein, the possible relative positions of the elements of the fusion protein of the invention would fit the following scheme (wherein RP refers to a reporter protein and the numbering stated above for the elements is retained: (1) polycationic peptide, (2) intervening polypeptide region, (3) positively charged amino acid region):

N-(1)-(2)-RP-(3)-C
N-(1)-linker-(2)-RP-(3)-C
N-(1)-(2)-linker-RP-(3)-C
N-(1)-linker-(2)-linker-RP-(3)-C
N-(3)-RP-(2)-(1)-C
N-(3)-RP-linker-(2)-(1)-C
N-(3)-RP-(2)-linker-(1)-C
N-(3)-RP-linker-(2)-linker-(3)-C
N-(1)-(2)-RP-linker-(3)-C
N-(1)-linker-(2)-RP-linker-(3)-C
N-(1)-(2)-linker-RP-linker-(3)-C
N-(1)-linker-(2)-linker-RP-linker-(3)-C
N-(3)-linker-RP-(2)-(1)-C
N-(3)-linker-RP-linker-(2)-(1)-C
N-(3)-linker-RP-(2)-linker-(1)-C
N-(3)-linker-RP-linker-(2)-linker-(3)-C
N-(2)-(1)-RP-(3)-C
N-(2)-linker-(1)-RP-(3)-C
N-(2)-(1)-linker-RP-(3)-C
N-(2)-linker-(1)-linker-RP-(3)-C
N-(2)-RP-(3)-(1)-C
N-(2)-(3)-RP-(1)-C
N-(2)-linker-RP-(3)-(1)-C
N-(2)-linker-(3)-RP-(1)-C
N-(2)-RP-(3)-linker-(1)-C
N-(2)-(3)-RP-linker-(1)-C
N-(2)-linker-RP-(3)-linker-(1)-C
N-(2)-linker-(3)RP-linker-(1)-C
N-(1)-RP-(3)-(2)-C
N-(1)-(3)-RP-(2)-C
N-(1)-RP-(3)-linker-(2)-C
N-(1)-(3)-RP-linker-(2)-C
N-(1)-linker-RP-(3)-(2)-C
N-(1)-linker-(3)-RP-(2)-C
N-(1)-linker-RP-(3)-linker-(2)-C
N-(1)-linker-(3)-RP-linker-(2)-C
N-RP-(3)-(1)-(2)-C
N-(3)-RP-(1)-(2)-C
N-RP-(3)-linker-(1)-(2)-C
N-(3)-RP-linker-(1)-(2)-C
N-RP-(3)-(1)-linker-(2)-C
N-(3)-RP-(1)-linker-(2)-C
N-RP-(3)-linker-(1)-linker-(2)-C
N-(3)-RP-linker-(1)-linker-(2)-C Preferred Fusion Proteins of the Invention In a preferred embodiment, the fusion protein is the T22-GFP-H6-5FdU which comprises:
  (i) The T22 peptide as polycationic peptide,
  (ii) GFP as intervening polypeptide region,
  (iii) A hexahistidine region as positively charged amino acid-rich region,
  (iv) A floxuracile pentanucleotide as therapeutic agent In a more preferred embodiment, the T22-GFP-H6-5FdU is formed by a linkage between an amino group in the side chain of the GFP protein and a thiol group in the therapeutic agent connected by a 6 atom spacer region.

In a preferred embodiment, the fusion protein is the T22-STM-H6-5FdU which comprises:
  (i) The T22 peptide as polycationic peptide,
  (ii) The STM variant of Ste2 as defined above as intervening polypeptide region,
  (iii) A hexahistidine region as positively charged amino acid-rich region,
  (iv) A floxuracile pentanucleotide as therapeutic agent.

In a more preferred embodiment, the T22-STM-H6-5FdU is formed by a linkage between an amino group in the side chain of the STM protein and a thiol group in the therapeutic agent connected by a 6 atom spacer region.

Stoichiometry of the Fusion Protein and Nanoconjugates of the Invention

The number of therapeutic agents which are conjugated to the fusion protein of the invention, while not being particularly limitative, will depend on the number of available residues in the intervening polypeptide which are available for chemical conjugation with the therapeutic agent. Since most conjugations occur via amino- or sulfhydryl groups present in the side chains of the amino acids forming part of the intervening polypeptide, the number of therapeutic agents conjugated to the fusion protein will depend on the number of lysine and arginine residues (for a conjugation via an amino groups in the side chains) or on the number of cysteine residues (for conjugation via sulphidryl groups in the side chains) as well as on the yield of the conjugation reaction. Thus, in a particular embodiment of the invention, the fusion protein of the invention is conjugated to at least 1, 2, 3, 4, 5, 6, 7, 8, 9, 10, 12, 15, 17, 20, 25, 30 therapeutic agents.

It will be understood that, in the particular case wherein the therapeutic agent is provided as a polymer, the number of therapeutic agents will also depend on the number of the monomers in the polymer. In the particular case of a FdU oligomer, the number of therapeutic agents in a given fusion protein will be the result of multiplying the number of oligomers attached to the fusion protein by the number of monomers. In the preferred case of a FdU pentamer, preferred embodiments include fusion proteins comprising at least 5, 10, 15, 20, 25, 30, 35, 40, 45, 50, 60, 75, 85, 100, 125, 150 or more therapeutic agents per fusion protein, corresponding, respectively, to 1, 2, 3, 4, 5, 6, 7, 8, 9, 10, 12, 15, 17, 20, 25 or 30 FdU pentamers conjugated per molecule.

In addition, the nanoparticles according to the invention result from the assembly of multiple copies of the fusion proteins of the invention. In preferred embodiments, the nanoparticle comprises t least 2, 3, 4, 5, 6, 7, 8, 9, 10, 11, 12, 13, 14, 15, 17, 20, 25, more preferably at least 15 monomers of the fusion protein of the invention.

Accordingly, the total number of therapeutic agents attached to each nanoparticle will depend on (i) the number of therapeutic agents conjugated to each fusion protein, (ii) the oligomerization state of the therapeutic agents and (iii) the number of fusion proteins forming the nanoparticle. In preferred embodiments, the nanoparticle is conjugated to at least 30, 35, 40, 45, 50, 60, 65, 70, 57, 80, 85, 90, 59, 100, 125, 150, 175, 200, 225, 250, 275, 300 therapeutic agents. In a further preferred embodiment, the nanoparticle is conjugated to at least 30, 35, 40, 45, 50, 60, 65, 70, 57, 80, 85, 90, 59, 100, more preferably at least 60 molecules of FdU pentamer.

Method for Preparing the Fusion Proteins of the Invention

In a second aspect, the invention relates to a method to prepare the fusion proteins of the invention comprising the steps of:
  a) providing a fusion protein comprising
    i. a polycationic peptide,
    ii. an intervening polypeptide region and
    iii. a positively charged amino acid-rich region,
    wherein the polycationic peptide and the positively charged amino acid-rich region are located at the ends of the protein and b) contacting said fusion protein with an activated form of a therapeutic agent or of an oligomeric form thereof wherein said activated form of a therapeutic agent or of an oligomeric form thereof contains a reactive group which is capable of reacting with at least one group in the intervening region of the fusion protein and wherein the contacting is carried out under conditions adequate for the formation of a bond between the reactive group in the therapeutic agent and the group in the intervening polypeptide region In another embodiment, the invention relates to a method to prepare the fusion proteins of the invention comprising the steps of:
 a) providing a fusion protein comprising
  i. a polycationic peptide,
  ii. an intervening polypeptide region and
  iii. a positively charged amino acid-rich region,
  wherein the polycationic peptide and the positively charged amino acid-rich region are located at the ends of the protein and wherein the fusion protein is provided in an activated form, wherein said activated form of the fusion protein contains a reactive group in the intervening region and
 b) contacting said fusion protein with a therapeutic agent or an oligomeric form thereof, wherein said therapeutic agent contains a group which is capable of reacting with the reactive group in the fusion protein, wherein said contacting is carried out under conditions adequate for the formation of a bond between the reactive group in the fusion protein and the group in the therapeutic agent.

The person skilled in the art will recognize that "reactive group", as used herein, refers to any moiety of a molecule which is capable of chemically reacting with another moiety from another molecule in such a fashion so as to bind the two molecules together, usually with the release of one or more additional molecules. Many such reactions are known in the art such as the formation of the peptide bond between a carboxyl and an amine group being one non-limiting example among them.

"Activated", as used herein when referring to a molecule, refers to a modified version of the molecule which contains a chemical modification whereby said molecule is capable to chemically react in a manner not previously present in the molecule (for instance, the activation adds a moiety not present previously, allowing for a bond that was unfeasible before) or with an increased reactivity (meaning that the reaction of the molecule with another molecule requires a lower activation energy than in the inactivated state). The present invention contemplates the possibility of activating the therapeutic agent and then contacting the activated therapeutic agent with the fusion protein or of activating the fusion protein and then contacting the activated fusion protein with the therapeutic agent. In both cases, the activation of the fusion protein or of the therapeutic agent is usually carried out by reacting the molecule to be activated with a reagent that introduces the reactive group in a suitable moiety in the molecule to be activated. Examples of reactive groups that allow the therapeutic agent or fusion proteins to be activated include, but are not limited, to carboxyl, amine, imine, thiol, sulfone, hydroxyl, sulfate, and phosphate moieties, among many others which are commonly known to the person skilled in the art. The activated form of the therapeutic agent is also herein referred to as the "activated therapeutic agent". The activated form of the fusion protein is also herein referred to as the "activated fusion protein". The reactive group or groups in the activated fusion protein is or are located in the intervening region, although it is not excluded that additional reactive groups can also be found in other regions of the fusion protein.

In those embodiments of the invention wherein a linking moiety mediates the bond between the fusion protein and the therapeutic agent, the linking moiety is a bifunctional cross-linker and, more preferably, a heterobifunctional cross-linker, tjhat reacts with the groups in the therapeutic agent and in the fusion protein, either sequentially (either reacting with the activated therapeutic agent first and then with the fusion protein, or first with the fusion protein and then with the activated therapeutic agent) or simultaneously, using among other linkages such as thioethers, amide bonds, carbon-nitrogen double bonds, or linkages generated by cycloaddition as disclosed in Kalia J et al. Advances in bioconjugation. Curr Org Chem 2010 January, 14(2):138-147). As a way of example typical thiol-reactive functional groups include iodoacetamides, maleimides, and disulfides. In addition, a protein can be treated with a small molecule or surface displaying an activated ester (e.g., an N-hydroxysuccinimidyl ester) to form amide bonds with the amino groups on lysine side chains and the N terminus. In another embodiment, the linking moiety is a heterobifunctional cross-linker which contains reactive groups capable of reacting with a thiol group and with an amino group. In one embodiment, the heterobifunctional cross-linker is 6-maleimidohexanoic acid N-hydroxysuccinimide ester.

In a preferred embodiment, the linking moiety reacts in a first step with the activated therapeutic agent and in a second step with the fusion protein. In another embodiment, the linking moiety reacts in a first step with the fusion protein and, in a second step, with the therapeutic agent.

It is intended that the step of contacting the fusion protein of the invention with the activated form of the therapeutic agent is carried out in a medium which favors the reaction establishing the bond between them. Media suitable for the reactions are commonly known to the person skilled in the art, including aqueous buffers and non-aqueous buffers. It is also intended that solid supports can be used in conjunction with the media for any of the reaction steps conducing to the synthesis of the activated therapeutic agent and the conjugate of the fusion protein, the therapeutic agent, and also the linking moiety in the embodiments that include one. Furthermore, it is intended that the method for the preparation of the conjugates between the fusion protein and the therapeutic agent is not limited to the fusion protein, the activated therapeutic agent, and the linking moiety, but that some embodiments include also the use of one or more catalysts and co-factors in the reaction.

Thus, in one embodiment of the invention, the activated form of the therapeutic agent contains a group which reacts with at least one of the side chains of a residue in a peptide region of the fusion protein, preferably in the intervening region of the fusion protein.

In another preferred embodiment said residue is an external lysine. In a further preferred embodiment of the invention, the group of the activated therapeutic agent, preferably the chemotherapeutic agent, which reacts with the side chain of the intervening region of the fusion protein is a thiol group.

In an even more preferred embodiment of the invention, the activated therapeutic agent is an activated chemotherapeutic agent, more preferably a thiol-functionalized oligofloxuridine.

In a further preferred embodiment, the linking moiety is 4-maleimido hexanoic acid N-hydroxysuccinimide ester mediates the conjugation between the activated therapeutic agent and the side chain of the residue of the peptide region of the fusion protein indicated in the previous embodiments of this section. In a yet more preferred embodiment, the linking moiety 4-maleimido hexanoic acid N-hydroxysuccinimide ester is bound in a first step to the therapeutic agent, preferably the activated FdU, yet more preferably FdU functionalized with a sulfhydryl, and in a second step to the side chain in a residue of the fusion protein, more preferably to external lysines of the fusion protein, even more preferably to external lysines of the intervening region of the fusion protein.

It is also intended that the step of contacting the activated fusion protein of the invention with the therapeutic agent is carried out in a medium which favors the reaction establishing the bond between them. Media suitable for the reactions are commonly known to the person skilled in the art, including aqueous buffers and non-aqueous buffers. It is also intended that solid supports can be used in conjunction with the media for any of the reaction steps leading to the synthesis of the conjugate of the fusion protein and the therapeutic agent, and also the linking moiety in the embodiments that include one. Furthermore, it is intended that the method for the preparation of the conjugates between the fusion protein and the therapeutic agent is not limited to the fusion protein, the activated therapeutic agent, and the linking moiety, but that some embodiments include also the use of one or more catalysts and co-factors in the reaction.

Thus, in one embodiment of the invention, the activated form of the fusion protein contains a group which reacts with at least one moiety in the therapeutic agent. In a further preferred embodiment of the invention, the group of the therapeutic agent, preferably the chemotherapeutic agent, which reacts with the activated fusion protein is a thiol group.

In an even more preferred embodiment of the invention, the activated fusion protein agent is an amino functionalized fusion protein wherein one or more amino groups in the side chain of the amino acids forming part of the intervening polypeptide is modified with an activated group having thiol reactivity. In a further preferred embodiment, the linking moiety is 4-maleimido hexanoic acid N-hydroxysuccinimide ester mediates the conjugation between an amino group in the fusion protein and a thiol group in the therapeutic agent In a yet more preferred embodiment, the linking moiety 4-maleimido hexanoic acid N-hydroxysuccinimide ester is bound in a first step to the fusion protein, more preferably to external lysines of the fusion protein and in a second step to the therapeutic agent side chain in a residue of the fusion protein.

Nanoparticles of the Invention and Methods for Preparing Them with the Fusion Proteins of the Invention In a third aspect, the invention relates to a method to prepare nanoparticles comprising multiple copies of the fusion protein according to the first aspect of the invention comprising placing a preparation of said fusion protein in a low salt buffer.

As the person skilled in the art will recognize, "nanoparticles" are microscopic particles whose size is measured in nanometers. The nanoparticles of the invention comprise the nanoparticles that result from the aggregation of multiple copies of the fusion protein of the invention as defined in the previous section. In the method for preparing nanoparticles with the fusion proteins of the invention, the preparation of the fusion protein of the invention comprises the monomeric form of the fusion proteins of the invention, which are thermodynamically favored to form non-covalent electrostatic unions and spontaneously aggregate in the conditions of the low salt buffer.

The person skilled in the art will acknowledge that the size of the nanoparticles can be in the range between 1 and 1000 nm, more preferably between 2,5 and 500 nm, even more preferably between 5 and 250 nm, and yet even more preferably between 10 and 100 nm. It will be understood that the expression "low salt buffer" comprises any buffer solution resulting from the dissolution of one or more salts in water with the capability to moderate changes in pH, wherein the amount of dissolved salt or salts results in an osmolarity lower or equal to that of the physiological fluids, such as the cytoplasm or the extracellular medium, for instance. Thus, the low salt buffer is understood to keep pH and osmolarity inside the range of physiological values and will be used inside the range of physiological temperatures.

The person skilled in the art will recognize that the range of physiological temperatures can oscillate between 15 and 45° C., more preferably between 20 and 40° C., even more preferably between 25 and 39° C., yet even more preferably between 30 and 37° C. The person skilled in the art will also acknowledge that the osmolarity of the low salt buffer will be in the range between 100 and 400 milli-osmoles/L (mOsm/L), preferably between 150 and 350 mOsm/L, more preferably between 200 and 300 mOsm/L, even more preferably between 225 and 275 mOsm/L.

Low salt buffers suitable for the invention, for instance, are the Tris-dextrose buffer (20 mM Tris +5% dextrose, pH 7.4), the Tris-NaCl buffer (20 mM Tris, 500 NaCl, pH 7.4), the PBS-glycerol buffer (phosphate buffered saline, PBS, pH 7.4, which is well known in the art, +10% glycerol), Tris Buffered Saline (TBS)-dextrose (20 mM Tris-HCl buffer pH 7.5, well known in the art, 200NaCl, +5% dextrose), Tris Buffered Saline-Tween 20 (TBST) buffer (10 mM Tris-HCl pH 7.5, 200 mM NaCl, +0.01% Tween 20), or any physiological buffer known in the art with a pH not lower than 6.

In a preferred embodiment of the invention, the low salt buffer of the method of the invention is selected from the group consisting of a carbonate buffer, a Tris buffer and a phosphate buffer.

In a particularly preferred embodiment of the invention, the low salt buffer of the method of the invention is a carbonate buffer that comprises sodium bicarbonate at a concentration between 100 and 300 nM. In another particularly preferred embodiment of the invention, the low salt buffer of the method of the invention is a Tris buffer that comprises Tris at a concentration of between 10 and 30 nM. In another particularly preferred embodiment of the method of the invention, the low salt buffer of the invention is a phosphate buffer that comprises $Na_2HPO_4$ and $NaH_2PO_4$ at a total concentration of between 5 mM and 20 mM.

In an even more preferred embodiment of the invention, the low salt buffer of the method of the invention further comprises dextrose and/or glycerol.

In a yet more preferred embodiment of the invention, the low salt buffer of the method of the invention has a pH between 6.5 and 8.5.

In an even yet more preferred embodiment of the invention, the low salt buffer of the method of the invention is selected from the group consisting of
 (i) 166 mM $NaHCO_3$, pH 7.4
 (ii) 20 mM Tris, 500 mM NaCl, 5% dextrose, pH 7.4
 (iii) 140 mM NaCl, 7.5 mM $Na_2HPO_4$, 2.5 mM $NaH_2PO_4$, 10% glycerol, pH 7.4

In another aspect of the invention, the invention relates to nanoparticles comprising multiple copies of the fusion protein of the first aspect of the invention or prepared according to the method or the invention for preparing nanoparticles.

Thus, the nanoparticles of the invention comprise aggregates of multiple copies of the fusion proteins of the invention, which result from the electrostatic interaction between regions in their structures favoring their non-covalent binding and coupling in physiological conditions. Since the method of the invention for the preparation of nanoparticles comprises placing a preparation of the fusion protein of the invention in a low salt buffer, it is understood that the nanoparticles thus formed comprise also an aggregate of multiple copies of the fusion protein.

In a preferred embodiment of the invention, the nanoparticles of the invention have a diameter between 10 and 100 nm.

Uses in Medicine of the Fusion Protein and the Nanoparticle of the Invention

In another aspect, the invention relates to a fusion protein or a nanoparticle according to the invention for use in medicine. In another aspect, the invention relates to the use of a fusion protein or a nanoparticle according to the invention for the treatment of a patient suffering from a disease that responds to the therapeutic agent forming part of the fusion protein of the invention.

As used herein, the terms "treat", "treatment" and "treating" refer to the reduction or amelioration of the progression, severity and/or duration of a condition, disorder or disease, or the amelioration of one or more symptoms (preferably, one or more discernible symptoms) of a condition, disorder or disease. The terms "treat", "treatment" and "treating" also refer to the amelioration of at least one measurable physical parameter of a condition, disorder or disease not necessarily discernible by the patient. Furthermore, "treat", "treatment" and "treating" refer also to the inhibition of the progression of a condition, disorder or disease, either physically by, e.g., stabilization of a discernible symptom, physiologically by, e.g., stabilization of a physical parameter, or both. "Treat", "treatment" and "treating" may refer, too, to the reduction or stabilization of the condition, disorder or disease.

It will be understood by the person skilled in the art that by use in medicine, the fusion protein or nanoparticle of the invention can be administered to a patient in order to induce a therapeutic response.

The therapeutic response comprises the suppression, reduction or arrest of the causes of the pathological condition or the disease suffered by a patient; the elimination, reduction, arrest or amelioration of the symptoms of the condition or disease; or the extinction, arrest or slowing down of the progression of the condition or disease in the patient.

The person skilled in the art will acknowledge that the fusion protein or nanoparticle of the invention suitable for use in medicine may be presented accompanied by a pharmaceutically acceptable carrier. As used herein, the term "pharmaceutically acceptable carrier" means a non-toxic, inert solid, semi-solid or liquid filler, diluent, encapsulating material or formulation auxiliary of any type. Remington's Pharmaceutical Sciences. Ed. by Gennaro, Mack Publishing, Easton, Pa., 1995 discloses various carriers used in formulating pharmaceutical compositions and known techniques for the preparation thereof.

Accordingly, the compositions comprising the fusion protein or nanoparticle of the invention and a pharmaceutically acceptable carrier are pharmaceutical compositions.

The pharmaceutical compositions of this invention can be administered to a patient by any means known in the art including oral and parenteral routes. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

A—Use of the Fusion Protein or the Nanoparticle of the Invention in the Treatment of Cancer.

Another embodiment of the invention relates to a fusion protein and the nanoparticle of the invention, or their corresponding pharmaceutical compositions, wherein the polycationic peptide is a sequence capable of specifically interacting with a receptor on a cell surface which is capable of promoting the internalization of the fusion protein into the cell, wherein said cell expressing the receptor is a tumor cell present in cancer, and wherein the therapeutic agent is selected from the group consisting of (i) A chemotherapy agent,
(ii) a cytotoxic polypeptide,
(iii) an antiangiogenic polypeptide,
(iv) a polypeptide encoded by a tumor suppressor gene,
(v) a pro-apoptotic polypeptide,
(vi) a polypeptide having anti-metastatic activity,
(vii) a polypeptide encoded by a polynucleotide which is capable of activating the immune response towards a tumor and
(viii) an antiangiogenic molecule.
(ix) a toxin for use in the treatment of cancer.

As used herein, the terms "treat", "treatment" and "treating" refer to the reduction or amelioration of the progression, severity and/or duration of cancer, or the amelioration of one or more symptoms (preferably, one or more discernible symptoms) of cancer. The terms "treat", "treatment" and "treating" also refer to the amelioration of at least one measurable physical parameter of cancer, such as growth of a tumor, not necessarily discernible by the patient. Furthermore, "treat", "treatment" and "treating" refer also to the inhibition of the progression of cancer, either physically by, e.g., stabilization of a discernible symptom, physiologically by, e.g., stabilization of a physical parameter, or both. "Treat", "treatment" and "treating" may refer, too, to the reduction or stabilization of tumor size or cancerous cell count.

The term "cancer" refers to a group of diseases involving abnormal, uncontrolled cell growth and proliferation (neoplasia) with the potential to invade or spread (metastasize) to other tissues, organs or, in general, distant parts of the organism; metastasis is one of the hallmarks of the malignancy of cancer and cancerous tumors. The abnormal growth and/or proliferation of cancerous cells is the result of a combination of genetic and environmental factors that alter their normal physiology. The growth and/or proliferation abnormalities of cancerous cells result in physiological disorders and, in many cases, death of the individual, due to the dysfunctionality or loss of functionality of the cell types, tissues and organs affected.

The term "cancer" includes, but is not restricted to, cancer of the breast, heart, small intestine, colon, spleen, kidney, bladder, head, neck, ovaries, prostate gland, brain, pancreas, skin, bone, bone marrow, blood, thymus, womb, testicles, hepatobiliary system and liver; in addition to tumors such as, but not limited to, adenoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, hepatobiliary cancer, osteosarcoma, retinoblastoma, rhabdomyosarcoma, sarcoma and teratoma. Furthermore, this term includes acrolentiginous melanoma, actinic keratosis adenocarcinoma, adenoid cystic carcinoma, adenomas, adenosarcoma, adenosquamus carcinoma, astrocytic tumors, Bartholin gland carcinoma, basal cell carcinoma, bronchial gland carcinoma, capillary carcinoid, carcinoma, carcinosarcoma, cholangiocarcinoma, cystadenoma, endodermal sinus tumor, endometrial hyperplasia, endometrial stromal sarcoma, endometrioid adenocarcinoma, ependymal sarcoma, Ewing sarcoma, focal nodular hyperplasia, germ cell tumors, glioblastoma, glucagonoma, hemangioblastoma, hemagioendothelioma, hemagioma, hepatic adenoma, hepatic adenomastosi s, hepatocellular carcinoma, hepatobilliary cancer, insulinoma, intraepithelial neoplasia, squamous cell intraepithelial neoplasia, invasive squamous-cell carcinoma, large cell carcinoma, leiomyosarcoma, melanoma, malignant melonoma, malignant mesothelial tumor, medulobastoma, medulloepithelioma, mucoepidermoid carcinoma, neuroblastoma, neuroepithelial adenocarcinoma, nodular melanoma, osteosarcoma, papillary serous adenocarcinoma, pituitary tumors, plasmacytoma, pseudosarcoma, pulmonary blastoma, renal cell carcinoma, retinoblastoma, rhabdomyosarcoma, sarcoma, serous carcinoma, microcytic carcinoma, soft tissue carcinoma, somatostatin secreting tumor, squamous carcinoma, squamous cell carcinoma, undifferentiated carcinoma, uveal melanoma, verrucous carcinoma, vipoma, Wilm tumor, intracerebral cancer, head and neck cancer, rectal cancer, astrocytoma, glioblastoma, microcytic cancer and non-microcytic cancer, metastatic melanoma, androgen-independent metastatic prostate cancer, androgen-dependent metastatic prostate cancer and breast cancer.

Thus, in a preferred embodiment of the invention, the therapeutic agent is selected from the group consisting of
 (i) a cytotoxic polypeptide,
 (ii) an antiangiogenic polypeptide,
 (iii) a polypeptide encoded by a tumor suppressor gene,
 (iv) a pro-apoptotic polypeptide,
 (v) a polypeptide having anti-metastatic activity,
 (vi) a polypeptide encoded by a polynucleotide which is capable of activating the immune response towards a tumor,
 (vii) a chemotherapy agent and
 (viii) an antiangiogenic molecule.

In a more preferred embodiment of the invention, the antitumor peptide of the fusion protein or the nanoparticle of the invention is selected from the group consisting of the BH3 domain of BAK, PUMA, GW-H1, and the active segment of diphtheria toxin I, and the *Pseudomonas aeruginosa* exotoxin A.

As used herein "BAK" refers to the well-known pro-apoptotic factor belonging to the Bcl-2 protein family that triggers programmed cell death by caspase-dependent apoptotic pathway through inactivating anti-apoptotic proteins, permeabilizing the mitochondrial membrane, and consequently, releasing cytochrome C and other mitochondrial cell death factors. [as seen in Llambi, F. et al. 2011. Mol. Cell, 44:517-31]. In one embodiment, BAK refers to full length BAK (SEQ ID NO: 41). In other embodiment, BAK refers to any truncated form thereof containing the functional BH3 domain (SEQ ID NO: 42).

As used herein, "PUMA" refers to a protein characterized by a full sequence corresponding to SEQ ID NO: 43 which is a (Bcl-2 homology 3) BH3-only protein that triggers cell death by interacting with pro and antiapoptotic proteins of the Bcl-2 family.

As used herein, GW-H1 refers to a polypeptide having the sequence of SEQ ID NO: 14 which exerts its cytolytic activity by folding into an amphipathic helix Diphtheria toxin I (produced by the bacteria of the species *Corynebacterium diphtherias*) (SEQ ID NO: 44) and the exotoxin of *P. aeruginosa* (SEQ ID NO: 45) belong to the family of ADP-ribosilating toxins. Both toxins are proteins that act on eukaryotic Elongation Factor-2 (eEF-2), basically inhibiting the translational activity of the cell that incorporates them and inducing apoptosis. The structure of both toxins presents a receptor-binding domain (that binds to a surface receptor of the cell and induces endocytosis; heparin binding epidermal growth factor precursor in the case of diphtheria toxin, CD91 in the case of the exotoxin A), a translocation domain, and a catalytic domain that performs the action on eEF-2 (an overview is provided in Shapira, A. & Benhar, I., 2010, Toxins, 2:2519-2583).

In an even more preferred embodiment of the invention, the polycationic peptide of the fusion protein or the nanoparticle of the invention is a CXCR4 ligand, and the cancer targeted to be treated with the fusion protein or the nanoparticle of the invention is characterized by comprising cells which express the CXCR4 receptor. In a more preferred embodiment, the cells cancer cells that express or overexpress CXCR4 are metastatic stem cells. The term "metastatic stem cells", as used herein, refers to cells that are responsible for metastasis initiation and metastasis maintenance In a yet more preferred embodiment of the invention, the CXCR4 ligand of the fusion protein or the nanoparticle of the invention is selected from the group comprising the T22 peptide, the V1 peptide, the CXCL12 peptide, the vCCL2 peptide or a functionally equivalent variant thereof.

In another more preferred embodiment of the invention, the cancer to be treated with the fusion protein or the nanoparticle of the invention is selected from the group consisting of pancreatic and colorectal cancer.

In another preferred embodiment of the invention, the fusion protein and the nanoparticle of the invention are used for the treatment of cancerous tumor, wherein the cancerous tumor is a primary tumor or a metastasis.

The invention will be described by way of the following examples which are to be considered as merely illustrative and not limitative of the scope of the invention.

EXAMPLES

Materials and Methods

Synthesis of 5'-dimethoxytrityl-5-fluoro-2'-deoxyuridine

5-Fluoro-2'-deoxyuridine (FdU) (3.2 mmol) was reacted with dimethoxytrityl chloride (4.4 mmol) in dry pyridine. The solution was stirred overnight and the solvent was evaporated. The residue was purified by column chromatography using a gradient from pure CH2Cl2 to 10% methanol in CH2Cl2 to afford the desired dimethoxytrityl-5-fluoro-2'-deoxyuridine (DMT-FdU) in 65%.

Synthesis of 5'-Dimethoxytrityl-5-fluoro-2'-deoxyuridine phosphoramidite

5'-Dimethoxytrityl-5-fluoro-2'-deoxyuridine (1 mmol) was dried by evaporation with anhydrous acetonitrile under reduced pressure. Next the product was dissolved in anhydrous $CH_2Cl_2$ (20 mL) under argon and diisopropylethylamine (5 mmol) was added with exclusion of moisture. The solution was cooled with an ice bath and 2-cyanoethoxy-N,N-diisopropylamino-chlorophosphine (2 mmol) was added dropwise with a syringe. The solution was stirred at room temperature for 1 h and, then, the solution was diluted with $CH_2Cl_2$ and washed with saturated aqueous NaCl. After drying the organic phase with anhydrous $Na_2SO_4$, the solvent was evaporated and the product was purified by column chromatography. The column was packed with silica gel using a 10% tritehylamine solution in ethyl acetate/hexane 1:1 and the compound was eluted with a gradient from ethyl acetate/hexane 1:1 to pure ethyl acetate. The desired phosphoramidite was obtained in 70% yield.

Preparation of the Solid Support Functionalized with 5'-dimethoxytrityl-5-fluoro-2'-deoxyuridine The DMT-FdU derivative (0.4 mmol) was dried by evaporation with anhydrous acetonitrile and reacted with succinic anhydride (0.6 mmol) and N,N-dimethylaminopyridine (0.6 mmol) in CH2Cl2 (20 mL). The reaction mixture was stirred overnight at room temperature. The reaction mixture was diluted with 30 mL of $CH_2Cl_2$ and the solution was washed with saturated aqueous NaCl, 10% citric acid aqueous solution and again with saturated aqueous NaCl. The organic layer was dried over anhydrous $Na_2SO_4$ and evaporated to dryness. The resulting DMT-FdU hemisuccinate was obtained as a white solid (89% yield) and was used in the next step without further purification. The DMT-FdU hemisuccinate derivative was incorporated on a long-chain alkylamine-controlled pore glass support (LCAA-CPG). Amino-LCAA-CPG (CPG New Jersey; 450 mg, 70 μmol amino/g) was placed into a polypropylene syringe fitted with a polypropylene disc and washed sequentially with methanol, $CH_2Cl_2$ and acetonitrile. Then 2,2'-dithiobis(5-nitropyridine) (0.18 mmol) dissolved in 0.6 mL of a mixture of acetonitrile/$CH_2Cl_2$ (1:3) was added to a solution of DMT-FdU hemissuccinate (0.9 mmol) and N.N-dimethylaminopyridine (0.18 mmol) in acetonitrile (1.5 mL). Next, triphenylphosphine (0.18 mmol) was added and the mixture was stirred for a few seconds, added to the support and allowed to react for 1 h. The support was washed with methanol, $CH_2Cl_2$ and acetonitrile and dried under vacuum. The functionality of the resin was determined by DMT quantification (42 μmol/g). Finally, the solid support was treated with an acetic anhydride solution during 30 min to cap the unreacted amino groups.

Synthesis of the Floxuridine Oligonucleotide (oligo-FdU)

Two pentanucleotide sequences were prepared: 1) 5'-(FdU)5-3' is the control FdU pentamer: and 2) 3'-thiolated FdU pentamer: 5'-(FdU)5-HEG-propyl-SH 3' with FdU 5-fluoro-2'-deoxyuridine and HEG as hexaethyleneglycol spacer. To synthetize the control 5'-(FdU)5-3' pentamer, a controlled pore glass (CPG) support functionalized with DMT-FdU prepared as described above was used. Then, the control pentamer sequence was assembled on a DNA synthesizer (392 Applied Biosystems, Foster City, CA, USA) using a 1 μmol synthesis cycle by successive additions of DMT-protected FdU phosphoramidite. After assembling of the sequence, oligonucleotide support was treated with aqueous ammonia (32%) for 2 hrs at room temperature and the resulting product was purified by HPLC. HPLC conditions: column X-bridge™ OST C18 (10×50 mm, 2.5 μm); 20 min linear gradient from 0% to 40%, flow rate 2 mL/min; solution A was 5% acetonitrile in 0.1 M aqueous triethylammonium acetate (TEAA) and solution B 70% acetonitrile in 0.1 M aqueous TEAA. Pentamer was characterized by mass spectrometry (MALDI-TOF).

Several batches of pentamer FdU oligonucleotide were synthesized in 1 μmol scale on an automated RNA/DNA synthesizer using β-cyanoethylphosphoramidite chemistry and following standard protocols. 3'-Thiol-Modifier C3 solid support (Link Technologies) was used for the introduction of the thiol group at the 3'-end, then hexaethyleneglycol phosphoramidite (Glen Research, VA, USA) was used as spacer. Finally, the synthesis was completed by addition the repetitive additions of the DMT-protected FdU phosphoramidite. After the assembly of the sequence, oligonucleotide support was treated with aqueous ammonia (32%) with 0.1 M 1,4-dithiothreitol (DTT) for 2 h at room temperature. The ammonia solution was concentrated to dryness and the product was desalted on NAP-10 (Sephadex G-25) columns eluted with water prior to use. The purity of the pentamer FdU-HEG-SH was analyzed by HPLC using the conditions described above (see FIG. 1). Pentamer was quantified by absorption at 260 nm and confirmed by MALDI mass spectrometry (MALDI-TOF).

Characterization of the T22-GFP-H6-FdU Therapeutic Nanoconjugate and Determination of Drug/Nanoparticle Ratio The products obtained after the T22-GFP-H6-FdU synthesis reaction were characterized using mass spectroscopy to measure their molecular mass. The volume and size distribution of the nanoparticles was determined by dynamic light scattering at 633 nm (Zetasizer Nano ZS, Malvern Instruments Limited, Malvern, Worcestershire, UK). Nanoconjugate size was also measured using purified samples, diluted to 0.2 mg/mL and contrasted by evaporation of 1 nm platinum layer in carbon-coated grids, before being visualized in a Hitachi H-7000 transmission electron microscope (TEM), as described33. The drug to nanoparticle ratio was obtained by analyzing the UV spectra of T22-GFP-H6 and T22-GFP-H6-FdU nanoconjugate and calculating the number of FdU molecules per T22-GFP-H6 nanoparticle.

T22-GFP-H6-FdU Internalization, CXCR4 Specificity and Cytotoxicity in CXCR4$^+$ HeLa Cells T22-GFP-H6-FdU capacity to internalize in a second cell type was assessed: the CXCR4$^+$ HeLa human cervical carcinoma cell line, cultured in Minimum Essential Medium medium supplemented with 10% FBS and 2 mM Glutamax (Gibco), by exposing cells for 1 hour to 1 μM T22-GFP-H6-FdU concentration and measuring the green fluorescence emitted by the internalized cells in the flow cytometer FACS-Canto system (Becton Dickinson). To assess specificity for CXCR4 receptor mediated internalization, competition studies incubating CXCR4$^+$ HeLa cells with the CXCR4 antagonist AMD3100 (octahydrochloride hydrate, Sigma-Aldrich) were performed in a 1:10 (Protein:antagonist) molar ratio for 1 h before exposure to the nanoconjugate, as previously described for the T22-GFP-H6.

The T22-GFP-H6-FdU subcellular localization was assessed using confocal microscopy. Briefly: for confocal analysis, cells were grown on culture dishes (Mat-Tek Co.); then, T22-GFP-H6-FdU was added in OptiPro medium supplemented with L-Glutamine. Nuclei were labeled with Hoechst 33342 (Life Technologies) and plasma membranes CellMask™ Deep Red (Life Technologies). Micrographs were taken by TCS-SP5 confocal laser scanning microscopy (Leica Microsystems, Wetzlar, Germany) and 3D models of T22-GFP-H6-FdU localization were generated using Imaris software (Bitplane).

T22-GFP-H6-FdU cytotoxic activity was also studied by using the MTT metabolic test (Roche). To that purpose, CXCR4+ HeLa cells were exposed to T22-GFP-H6-FdU at 1-1,000 nM concentration range and their viability measured at 48 hours as compared to equimolecular concentrations or free oligo-FdU. Afterwards, a graphic displaying the linearized T22-GFP-H6-FdU dose-response trend line representation to compare cell viability for both compounds was constructed. Reduction of cell viability was also determined by optical microscope images of HeLa cells exposed to 1 μM T22-197 GFP-H6-FdU for 48 h, as compared to T22-GFP-H6 or free FdU.

Generation of CCR Model and Protocol for the Treatment of Established Metastases A CXCR4+ SW1417 orthotopic CCR model in Swiss nude mice was used to evaluate the possible inhibition of established metastasis. T22-GFP-H6-FdU administration was started two month after tumor cell implantation (when metastases were already present in the mice measured by bioluminescence images using IVIS spectrum). To this purpose, 32 Swiss nude mice were randomized into four groups (buffer, T22-GFP-H6-FdU, T22-GFP-H6 and free FdU pentamer (n=10/each group). Single i.v. doses for each compound (T22-GFP-H6-FdU: 20 ug, T22-GFP-H6: 20 ug, free oligo-FdU at equimolecular doses or Buffer) were administered every three days for a total of 10 doses. The experiment was finished when the first animal of the buffer-treated group was euthanized.

Evaluation of Antimetastatic Effect

The same evaluation applied in the treatment protocol was applied for metastasis prevention. Briefly, at necropsy the number and size of visible metastasis in all organs were recorder per mouse, ex vivo the number of metastatic foci that emitted bioluminiscence in the target organs were counted using the IVIS® 200-Spectrum and the histopathological and immunohistochemical analyses to confirm location and number of metastases were performed.

T22-GFP-H6-FdU Biodistribution and Toxicity in Bone Marrow and Circulating Blood Cells The T22-GFP-H6-FdU uptake measuring fluorescence emission, in bone marrow and circulating blood cells, was assessed 5 h after the administration of T22-GFP-H6-FdU at 10-100 μg doses. At necropsy, bone marrow was extracted and registered ex vivo in the IVIS® 200-Spectrum equipment. Mouse blood was collected by punction in the maxillary plexus. The erythrocytes, leucocytes and platelets were isolated by the Ficoll density gradient method using the standard protocol. Further, pellets were obtained by centrifugation of the isolated cell extracts at 600 g, 10 min and then recorded to measure fluorescence using IVIS® 200-Spectrum.

Synthesis of the T22-GFP-H6-FdU Therapeutic Nanoconjugate.

The nanoconjugate was synthesized by covalent binding of the targeting vector T22-GFP-H6, a protein nanoparticle produced in bacteria using a recombinant DNA strategy and oligo-FdU, a pentameric oligonuclotide of Floxuridine (5-Fluoro-2'-deoxyuridine) (Sigma Aldrich Chemie GmbH, Steinheim, Germany), both functionalized before their conjugation. The oligo-FdU was functionalized with sulfhydryl as described in FIG. 1. T22-GFP-H6 was functionalized by reacting with the linker MBHS (4-maleimido hexanoic acid N-hydroxysuccinimide ester) (Thermo Fisher), following the protocol for biofunctionalization of proteins described by Hermanson [Hermanson, G. 2013. Bioconjugate Techniques, 3rd Edition, ISBN9780123822390, Academic Press, London, pp. 1200]. This linker binds the amino groups of the external lysines of the T22-GFP-H6 protein adding maleimido groups. The final T22-GFP-H6-FdU nanoconjugate was obtained reacting T22-GFP-H6 functionalized with maleimide and oligo-FdU-thiol (Michael reaction). The final reaction product was purified by dialysis. The functionalization and physicochemical characterization of oligo-FdU with thiol is described in FIG. 1. The physicochemical and functional characterization of the reaction products for the synthesis of T22-GFP-H6-FdU is described in FIG. 2.

Determination of the ratio of oligo-FdU to T22-GFP-H6 in the resulting nanoconjugate was determined based on the absorbances of a 1 mg/ml solution of the T22-GFP-H6 conjugate and of a 1 mg/ml solution of the T22-GFP-H6-FdU conjugate at 260 nm of UV light. The difference in the absorbances between both solutions provides the absorbance of the FdU molecules present in the T22-GFP-H6-FdU solution. Taking into account Lamber Beer law (Abs=mg/ml*E*L wherein E=44500 $M^{-1} \cdot Cm^{-1}$) and the molecular weight of the T22-GFP-H6 protein (MW=30,691 KDa), the number of moles of FdU per mg of T22-GFP-H6 protein were determined. Considering that the Absorbance of the T22-GFP-H6 is about 0.7/mg of protein, and the absorbance of the T22-GFP-H6-FdU is about 7.32/mg of fusion protein, results showed that 4.56 molecules of oligo-FdU are bound to each fusion protein.

T22-GFP-H6-FdU Internalization, CXCR4 Specificity and Cytotoxicity in CXCR4+ Cells In Vitro.

CXCR4+ SW1417-luc CRC cells were cultured in modified Eagle's medium (Gibco, Rockville, MD) supplemented with 10% fetal calf serum (Gibco), and incubated at 37° C. and 5% CO2 in a humidified atmosphere. The internalization capacity of the nanoconjugate was assessed by exposing CXCR4+ SW141-luc cells (expressing the luciferase reporter gene) for 1 hour to 1 mM T22-GFP-H6-FdU concentration, treating them with 1 mg/mL trypsin (Gibco) for 15 minutes, and measuring the green emitted fluorescence of the internalized nanconjugate particles in the flow cytometer FACS Canto system (Becton Dickinson, Franklin Lakes, NJ), using a 15 mW air-cooled argon ion laser at 488 nm excitation. Fluorescence emission was measured with a D detector (530/30 nm band pass filter). To assess specificity for CXCR4 receptor-mediated internalization, competition studies were performed incubating CRC SW1417 cells with the CXCR4 antagonist AMD3100 (Sigma Aldrich) in a 1:10 (protein:antagonist) molar ratio for 1 h before exposure to the nanoconjugate at 1 mM for an additional hour.

To assess T22-GFP-H6-FdU subcellular localization, the cells were cultured in MatTek culture dishes (MatTek Corporation, MA, USA); then, T22-GFP-H6-FdU was added in OptiPro medium supplemented with L-Glutamine. The nuclei were labeled with 0.2 μg/mL Hoechst 33342 (Molecular Probes, Eugene, OR) and the plasma membranes with 2.5 μg/mL CellMaskTM Deep Red (Molecular Probes) for 10 minutes in the dark. The cells were washed in phosphate-buffered saline (Sigma-Aldrich). Live cells were recorded by TCS-SP5 confocal laser scanning microscopy (Leica Microsystems, Heidelberg, Germany) using a Plan Apo 63×/1.4 (oil HC×PL APO lambda blue) objective as described. To determine particle localization inside the cell, stacks of 10-20 sections forevery 0.5 μm of cell thickness were collected and three-dimensional models were generated using Imaris version 6.1.0 software (Bitplane, Zurich, Switzerland).

T22-GFP-H6-FdU cytotoxic activity was also studied by measuring cell viability and using the metabolic test 3-(4, 5-dimethylthiazol-2-yl)-2,5-diphenyltetrazolium bromide (MTT, Roche, Basilea, Switzerland), following manufacturer recommendations. To that purpose, SW1417 CRC cells were exposed to T22-GFP-H6-FdU at 1.0-1,000 nM concentration range and measured their viability at 72 hours as compared to equimolecular concentrations of T22-GFP-H6 or free oligo-FdU. A dose-response curve was then constructed and the linearized T22-GFP-H6-FdU dose-response trend line for each compound was determined using the Sigmaplot vs.10.0 software.

Generation of CRC Mouse Models.

Three different CRC mouse models were used: one generated by subcutaneous CRC cell implantation to study nanoconjugate biodistribution and induction of CRC apoptosis and two generated by orthotopic cell implantation to study nanoconjugate biodistribution and antimetastaic effect, either for prevention of metastases or for induction of the regression of established metastases. To generate two of these models, five-week-old Swiss nude mice were used, whereas in one model NOD-SCID mice were employed. They were all female mice weighing 18 to 20 g (Charles River, L'Arbresle, France) and were housed in a sterile environment with bedding, water and γ-ray-sterilized food ad libitum. Experiments were approved by the Mouse Ethics Committee at Hospital de la Santa Creu i Sant Pau.

Subcutaneous (SC) Mouse CRC Model.

A subcutaneous CRC model was generated by injecting $1\times10^7$ CXCR4$^+$ human SW1417-luci CRC cells (expressing luciferase, to allow bioluminescence follow-up of tumor growth) resuspended in 250 µl of media in the mouse flank. When tumors reached 700 mm3, they were excised and implanted SC tumor aliquots (3×3×3 mm) by the trocher system in a cohort of mice. SC model was used to assess tumor uptake and nanoconjugate internalization and in vivo competition studies using co-administration of the CXCR4 antagonist AMD3100. It was also used to determine the induction of DNA double strand breaks, tumor cell apoptosis and the fraction of CXCR4$^+$ cancer cells remaining in tumor tissue (CXCR4$^+$ CCF) along time after treatment, as described below. These data were then used to design the required dosage interval for the nanoconjugate repeated dose therapy in subsequent experiments aimed to determine its antimetastatic effect.

Orthotopic (ORT) CRC Mouse Model Used to Study Regression of Established Metastases.

Swiss nude mice were anesthetized with ketamine and xylazine, exteriorizing their cecum by a laparotomy. $2\times10^6$ CXCR4$^+$ SW1417-luci CRC cells (expressing luciferase, to allow ex vivo bioluminescent identification of metastatic foci in affected organs at the end of therapy) were suspended in 50 ml of modified Eagle's medium, and loaded into a sterile micropipette. The cell suspension was slowly injected, under a binocular lens, with an approximate 30° angle and its tip introduced 5 mm into the cecal wall. Afterward, a slight pressure was applied with a cotton stick at approximately 2 mm from the injection point in the direction of the pipette axis. The pipette was pulled out and the area around the injection cleaned with 3% iodine. After injection, the gut was returned to the abdominal cavity and closed with surgical staples. This model was used to evaluate the capacity of the T22-GFP-H6-FdU nanoconjugate to induce the regression of established metastases.

Orthotopic (ORT) CRC Mouse Model to Study Prevention of Metastases.

A highly efficient metastatic model was generated in NOD/SCID mice, that received an intracecal microinjection (ORT) of SW1417-luci CRC cells disaggregated from SC tumours previously generated in a different cohort of NOD/SCID mice. Thus, a SC+ORT model, was produced: when SC tumors reached a volume of 700 mm3, mice were sacrificed by cervical dislocation and tumours were excised, discarding the necrotic areas. Three hundred mg of viable tumour tissue was then cut into pieces and disaggregated in a mix of 0.05% trypsin (Invitrogen) and 100 mg/ml DNase (Sigma-Aldrich). The mix was pipetted 30 times, using a 10 ml pipette, and incubated for 10 minutes at 37° C. with shaking. It was then re-pipetted 30 times, using 10 ml, 3 ml and 1 ml pipettes, and re-incubated for 5 minutes at 37° C. with shaking. This re-pipetting step was then repeated. The obtained SW1417 single-cell suspension was filtered through a cell strainer and centrifuged at 1,000 g for 10 minutes before counting the cells. Then 2×106 cells, previously grown in culture and resuspended in 50 µl of media, were microinjected in the cecum of each mouse, following the method described above. This model was used to evaluate the capacity of the T22-GFP-H6-FdU nanoconjugate to prevent metastasis development.

T22-GFP-H6-FdU Tumor Uptake, Tumor Cell Internalization and Induction of DNA Damage and Apoptosis 'In Vivo'.

The SC CXCR4$^+$ SW1417 CRC model was used to assess the internalization of the T22-GFP-H6-FdU nanoconjugate into the cytosol of CXCR4$^+$ tumor cells after the administration of 100 mg T22-GFP-H6-FdU as an i.v. single bolus compared with buffer, T22-GFP-H6 (untargeted nanoconjugate) and oligo-FdU (unconjugated free drug). Two hours, 5 h and 24 h after the administration, the mouse was euthanized to resect the tumor and register ex vivo the intensity of the green fluorescence emitted by the nanoconjugated that biodistributed to tumor tissue using the IVIS® 200-Spectrum (Perkin Elmer, MA, USA). Following, tumor tissue samples were taken, processed and performed immunohistochemistry (IHC) to determine the presence or absence of the corresponding nanoconjugate into cytosol of tumor cells using an anti-GFP antibody (1:300; Santa-Cruz Biotechnology, CA, USA). Double strand breaks (DSBs) formation was also measured by IHC using an anti-gH2AX mAb (1:400, Novus Biologicals, Cambridge, UK) and counted the number of stained cells in five magnification fields of different tumor sections in each mouse. Finally, the capacity of T22-GFP-H6-FdU for apoptosis induction was compared 24 h after the administration of an equimolecular dose of oligo-FdU or Buffer. Apoptosis was assessed determining nuclear condensation with Hoechst staining of tumor tissue sections and counting the number of condensed or defragmented nuclei in five high-power magnification fields in different sections for each tumor using the Olympus DP73 digital camera and the CellD Imaging 3.3 programme (Olympus, Tokyo, Japan).

Definition of the Optimal Dose Interval by Changes in CXCR4+ Tumor Cell Number After T22-GFP-H6-FdU Administration.

The SC SW1417 mouse model was used to determine the capacity of the nanoconjugate to induce DNA damage and apoptosis in tumor tissue, as well as the kinetics of CXCR4 expression in the membrane of tumor cells after treatment, regarding the fraction of CXCR4 expressing tumor cells and their intensity, since CXCR4$^+$ are the target cells for the nanoconjugate. To that purpose 24, 48, 72 h after the administration of a single i.v. bolus of 100 µg T22-GFP-H6-FdU, the mice were euthanized and tumor samples taken, which later were fixed and paraffin-embedded to determine the levels and the percent of tumor cells expressing CXCR4 using IHC with an anti-CXCR4 antibody (1:300, Abcam, UK). The mice had been treated with equimolecular dosages of T22-GFP-H6, free oligo-FdU or Buffer, in which also were determined the levels of CXCR4 expression in tumor tissue at the different time points. The results of the kinetics of CXCR4 expression in tumor cells were used to establish the optimal T22-GFP-H6-FdU nanoconjugate administration interval in the repeated dose schedule used to evaluate antimetastatic effect.

Treatment Protocol for the Evaluation of T22-GFP-H6-FdU Induction of Metastasis Regression.

Figure 3:
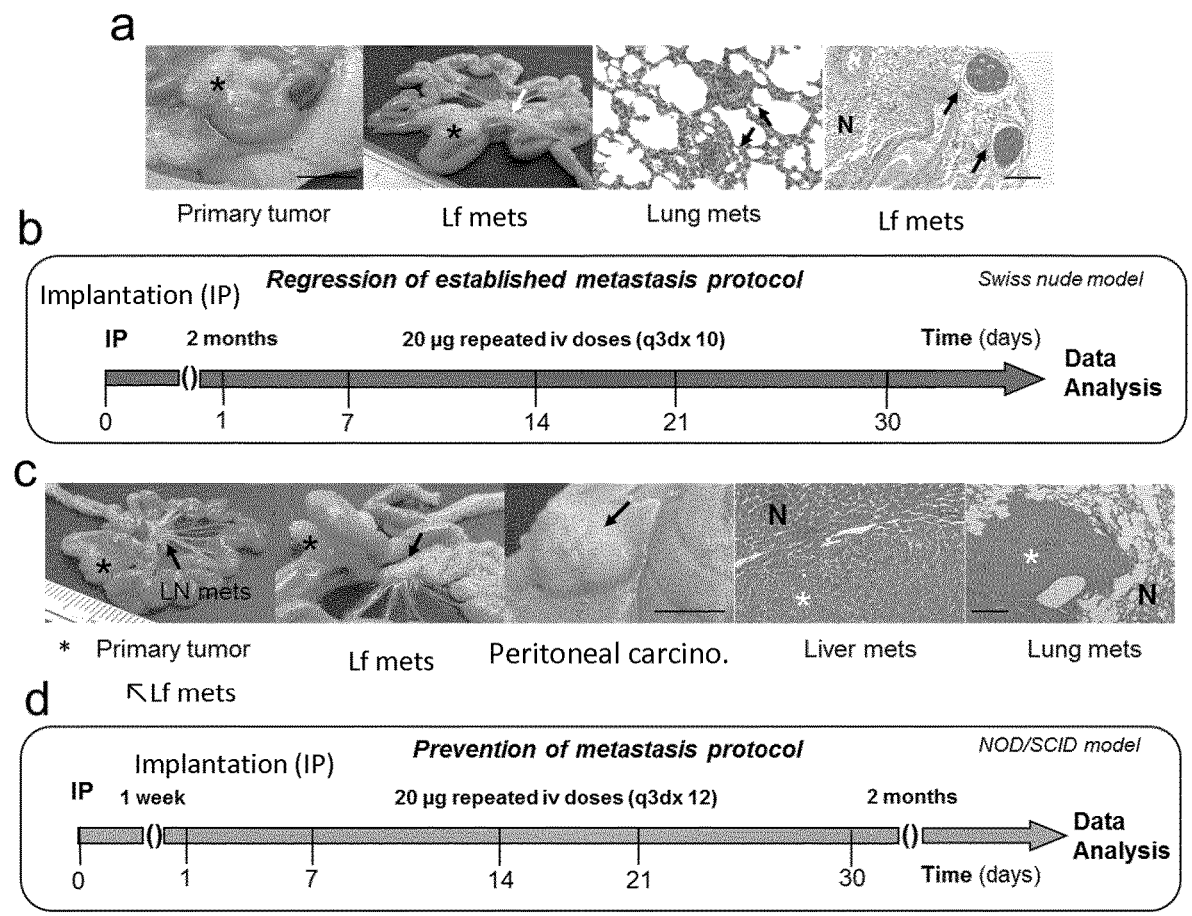
FIG. 3. Mouse models, experimental setting and T22-GFP-H6-FdU dosage used to evaluate antimetastatic effect in the regression and prevention of metastasis protocols. (a) Mouse model used in the regression of established metastasis protocol: Direct orthotopic implantation of CXCR4$^+$ bioluminescent SW1417 CRC cells in Swiss nude mice, which generates metastases in the lymph nodes and lung. Scale bar, 1 cm. (b) T22-GFP-H6-FdU administration, at a dosage of 20 µg q3d per 10 doses, was started 2 months after cecal implantation of CRC cells (when established metastases are already present) to evaluate the nanoconjugate capacity to induce the regression of established metastases. (c) Mouse model used in the prevention of metastasis protocol: subcutaneous passage of CXCR4$^+$ bioluminescent SW1417 cells followed by orthotopic implantation of disaggregated tumor cells (SC+ORT) in NOD/SCID mice, which generates metastases in LN, liver, lung and peritoneum. (d) T22-GFP-H6-FdU administration, at a dosage of 20 µg q3d per 12 doses, was started one week after cecal implantation of CRC cells (when no metastases could yet develop), to evaluate the nanoconjugate capacity to prevent metastasis development. In both experiments, T22-GFP-H6-FdU antimetastatic effect is compared to that achieved by equimolecular doses of free oligo-FdU. Prior to initiating the prevention of metastasis experiment we confirmed in separate mice that the mouse model used lacked micro or macrometastases before treatment start. Prior to the initiation of the regression of metastasis experiment, we confirmed in separate mice that metastatic foci were already present before treatment start. Scale bar, 100 µm.

The orthotopic and metastatic CRC model developed in Swiss nude mice was employed to perform experiments of metastasis regression. 40 mice were randomized into four groups: buffer, T22-GFP-H6, T22-GFP-H6-FdU and free oligo-FdU (n=10/group) and administered repeated i.v. boluses at equimolecular doses, as follows: T22-GFP-H6-FdU 20 μg, free oligo-FdU: 2.6 nmols, or buffer), every three days (q3d) for a total of 10 doses. The T22-GFP-H6-FdU administration was initiated two months after tumor cell implantation, the time at which it was determined, in previous experiments, that lymph node and lung metastases were present (FIG. 3). The experiment was finished when the first animal of the buffer-treated-group had to be euthanized. See below the studied parameters to evaluate the antimetastatic effect.

Treatment Protocol for the Evaluation of T22-GFP-H6-FdU Metastasis Prevention Effect.

The SC+ORT metastatic CRC model developed in NOD/SCID mice was used to evaluate the capacity of the nanoconjugate for metastasis prevention. 34 mice were randomly assigned into three groups: buffer (n=11), T22-GFP-H6-FdU (n=12) and free oligo-FdU (n=11) and administered repeated i.v. boluses at equimolecular doses, as follows: T22-GFP-H6-FdU 20 ug, free oligo-FdU: 2.6 nmols, or buffer), every three days (q3d) for a total of 12 doses. The T22-GFP-H6-FdU administration was initiated one week after tumor cell implantation before metastatic dissemination has occurred (FIG. 3). The experiment was finished when the first animal of the buffer-treated-group had to be euthanized.

Evaluation of Antimetastatic Effect and Determination of the CXCR4+ Cancer Cell Fraction in Tumor Tissue at the End of Therapy.

At the end of both the regression and the prevention of metastasis experiments, the same methodology was applied to determine T22-GFP-H6-FdU antimetastatic effect. At necropsy, the number and size of visible metastases in the organs where dissemination is expected in colorectal cancer (lymph nodes, liver, lung and peritoneum) were recorded for each mouse in all compared groups. Also the number of metastatic foci that emitted bioluminiscence (derived from the SW1417-luci CRC cells) were counted ex vivo in the target organs for metastasis, using the IVIS® 200-Spectrum (Perkin-Elmer). Samples for histopathological and immunohistochemical analyses were collected and processed. Two independent observers analyzed H&E stained samples to count the number and measure the size of all observed metastatic foci in three (metastasis prevention experiment) or six (regression of metastasis experiment) sections of each organ in each mouse. The images were taken and the measurements were performed with an Olympus microscope with the CellD Olympus software (v3.3). CXCR4 expression in tumor tissue was determined using IHC with an anti-CXCR4 antibody, as described above, to determine the fraction of CXCR4$^+$ cancer cells remaining in tumor tissue (CXCR4$^+$ CCF) after treatment, including primary tumor and metastatic foci at the different organs affected by metastases (peritoneum, liver, lung and lymph nodes). The obtained results were used to study a possible correlation between CXCR4$^+$ CCF and antimetastatic effect at the different sites.

T22-GFP-H6-FdU Biodistribution and Toxicity in Normal Organs.

The T22-GFP-H6-FdU uptake was assessed by measuring the green fluorescence emitted by the GFP domain of the nanoconjugate, as well as DNA DSBs and apoptotic induction in normal (non-tumor) tissues using the methodology described above. In addition, two independent observers evaluated the possible histopathological alterations observed in H&E stained non-tumor tissue samples, searching for signs of toxicity. These tissues included CXCR4-expressing organs (despite expressing this receptor to a significantly lower level than in tumor tissue) where the nanoconjugate could accumulate such as the bone marrow and spleen and the toxicity in non-CXCR4 expressing organs, especially those in which the unconjugated oligo-FdU such as the liver, was also assessed.

Statistical Analysis.

In order to analyze differences between control and experimental groups of affected mice in metastatic rates at the different organs, Fisher's exact test was used. The Mann-Whitney test was used to compare number and size of metastatic foci in the affected organs among groups. All quantitative values were expressed as mean±SE and the statistical tests were performed using SPSS version 11.0 (IBM, New York, USA). Differences among groups was considered significant at a p<0.05.

Example 1

Physicochemical Characterization of HS-oligo-FdU

The functionalized pentamer FdU-HEG-SH was quantified by absorption at 260 nm and confirmed by MALDI mass spectrometry (MALDI-TOF), yielding a MW of 1976.2, being the expected MW 1974.0. The control pentanucleotide (free oligo-FdU) characterized by mass spectrometry (MALDI-TOF) yield a MW of 1476.5, being the expected MW: 1478.1.

Example 2

Figure 2:
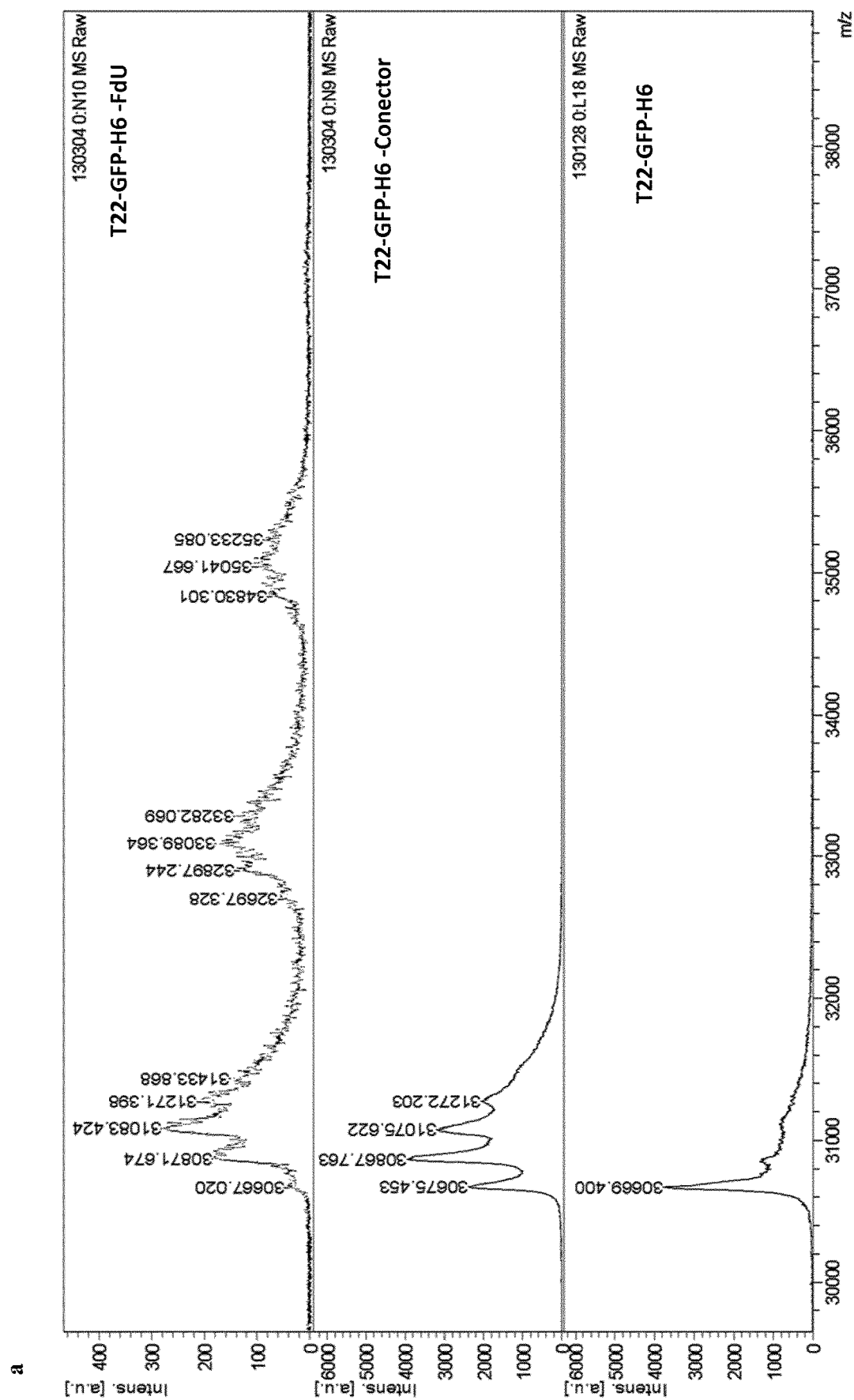
FIG. 2. Physicochemical characterization of the T22-GFP-116-FdU nanoconjugate and drug to nanoparticle ratio. The analysis of the products of the conjugation was performed by MALDI-TOFF spectra. (a) Mass spectrometry of the T22-GFP-H6-FdU conjugation products identifying the molecular mass of the products carrying 1 oligo-FdU or 2 oligo-FdU payloads, the unconjugated T22-GFP-H6 protein and the coupler-conjugated T22-GFP-H6. (b) T22-GFP-H6-FdU size as determined by dynamic light scattering, as compared to T22-GFP-H6 nanoparticle. (c) Representative T22-GFP-H6-FdU image as detected by transmission electron microscopy. (d) Molecular modeling of T22-GFP-H6-FdU self-assembled nanoparticle (source: Rueda, F. et al. Adv Mater 27, 7816-7822 (2015). Printed with permission from John Wiley & Sons).
Figure 2:
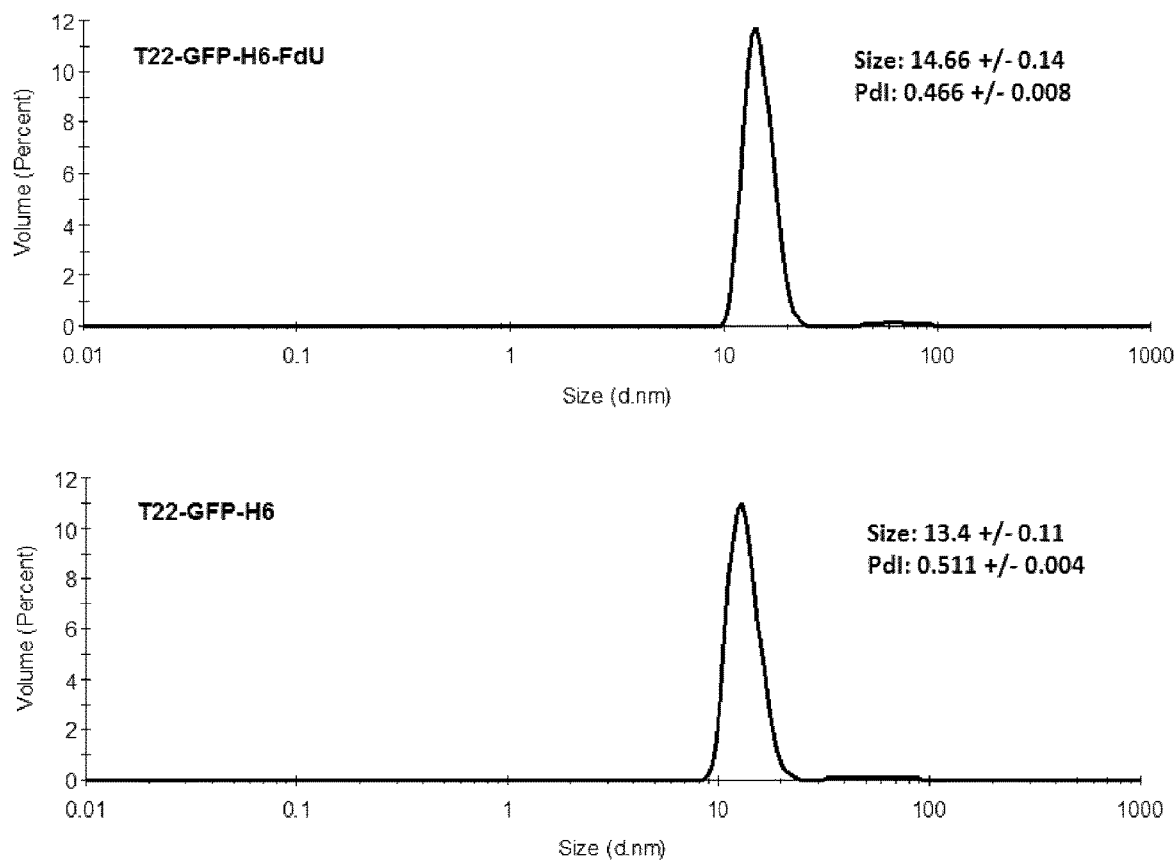
Figure 2:
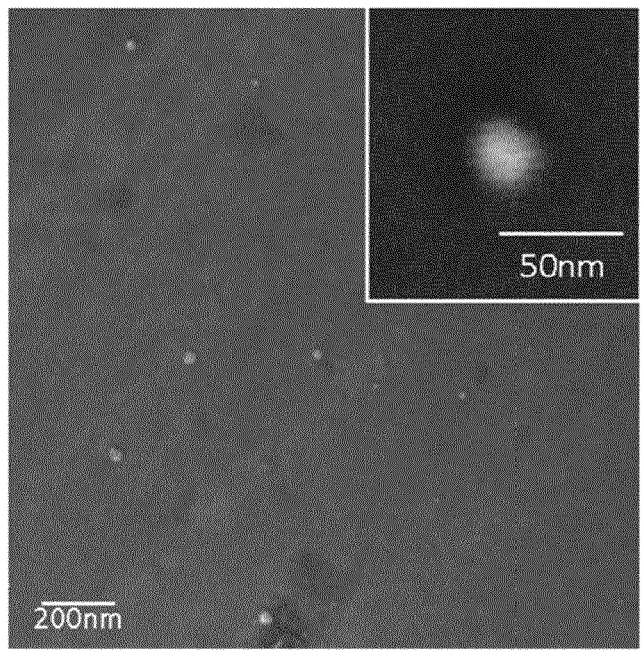
Figure 2:
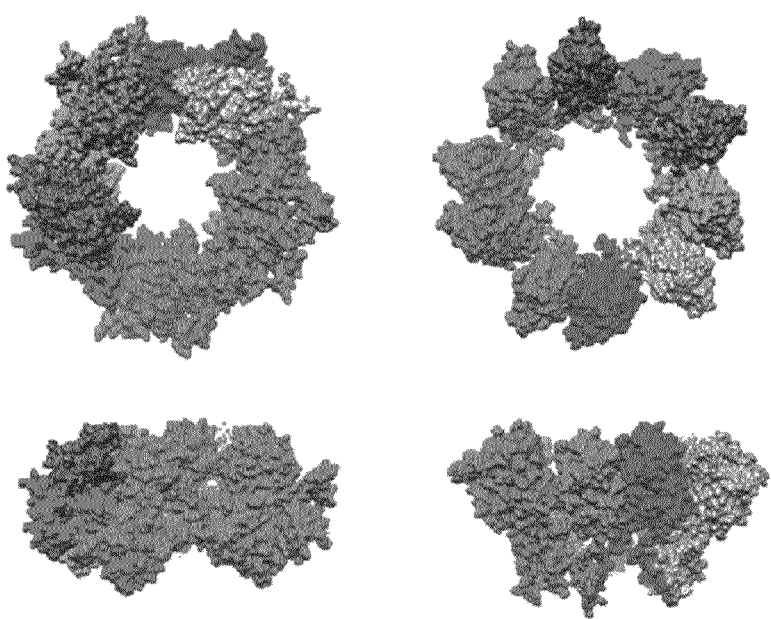

Physicochemical Characterization of the T22-GFP-H6-FdU Nanoconjugate and Determination of the Drug to Nanoparticle Ratio The analysis of the conjugation products was performed by MALDI-TOFF spectra identifying the peaks corresponding to one or two molecules of pentaoligonucleotides of FdU bound to the nanoparticle with the MW indicated in FIG. 2. The T22-GFP-H6-FdU size was determined by dynamic light scattering, being 14.6+0.14, as compared to 13.4+0.11 for the control T22-GFP-H6 nanoparticle, a size consistent with that determined by transmission electron microscopy. The molecular weight of the T22-GFP-H6 nanoparticles, determined by SEC-MALS is of 477 kDa. Considering that the molecular weight of the T22-GFP-H6 polypeptide is of 30,691 kDa, this results in that each nanoparticle has approximately 15 monomers. A drug/nanoparticle ratio of 60 was obtained for the product obtained in the T22-GFP-H6-FdU nanoconjugate synthesis reaction based on the UV spectra of T22-GFP-H6 and T22-GFP-H6-FdU nano-conjugate. This product incorporates an average of 4 molecules of the pentamer oligo-FdU which, when assembled into a nanoparticle containing 15 fusion proteins monomers, correspond to a total of 60 FdU molecules, per T22-GFP-H6 nanoparticle.

Example 3

Development of T22-GFP-H6-FdU, a Nanoconjugate that Targets CXCR4+ CRC Cells

Figure 4:
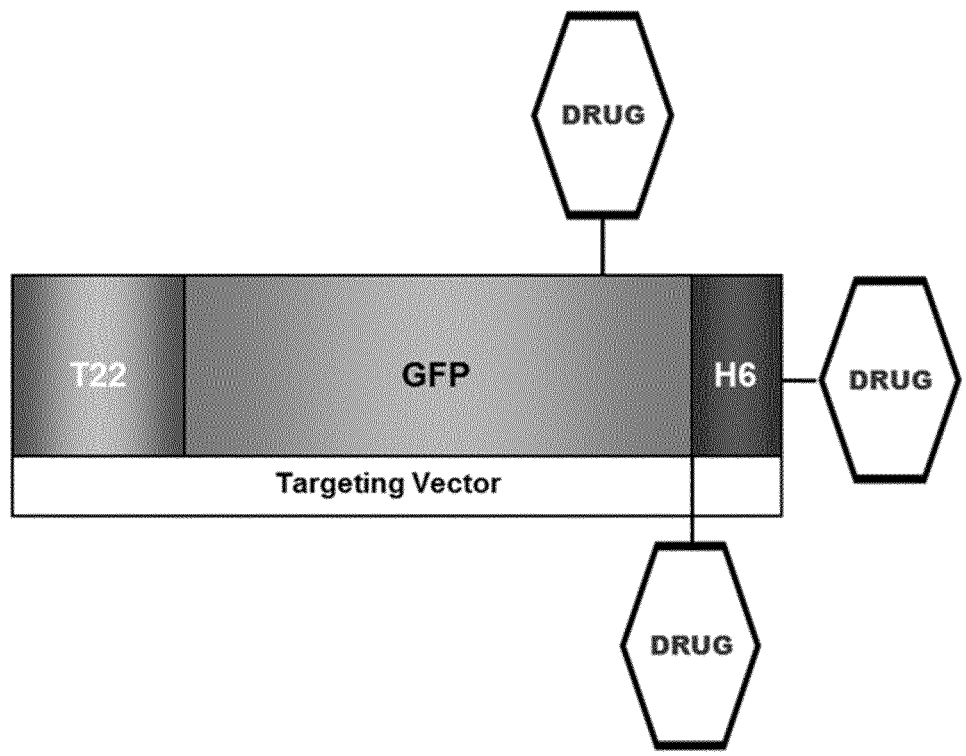
FIG. 4. T22-GFP-H6-FdU nanoconjugate synthesis and demonstration of selective internalization and killing of CXCR4$^+$ CRC cells in vitro. (a) The nanoconjugate contains a fusion protein, T22-GFP-H6 (described in Unzueta 2012)—composed of the peptide T22 as a CXCR4 ligand, a green fluorescent protein and a Histidine tail—bound to the payload drug. (b) Seven to nine pentameric oligonucleotides (approximately 40 molecules) of the antitumor drug 5-Fluoro-2'-deoxyUridine (FdU), named oligo-FdU, are conjugated to the T22-GFP-H6 targeting vector using a coupler. (c) T22-GFP-H6-FdU chemical synthesis: T22-GFP-H6 is first covalently bound to the MBHS (6-Male-imidohexanoic acid N-hydroxysuccinimide ester) coupler through its amino groups in the external lysines. The thiol-functionalized oligo-FdU (oligo-(FdU)5-SH) is then reacted with T22-GFP-H6 functionalized with maleimide (Michael reaction). (d) Nanoconjugate internalization in CXCR4 overexpressing (CXCR4$^+$) SW1417 CRC cells after 1 hour exposure at 1 as measured by fluorescence emission using flow cytometry.
Figure 4:
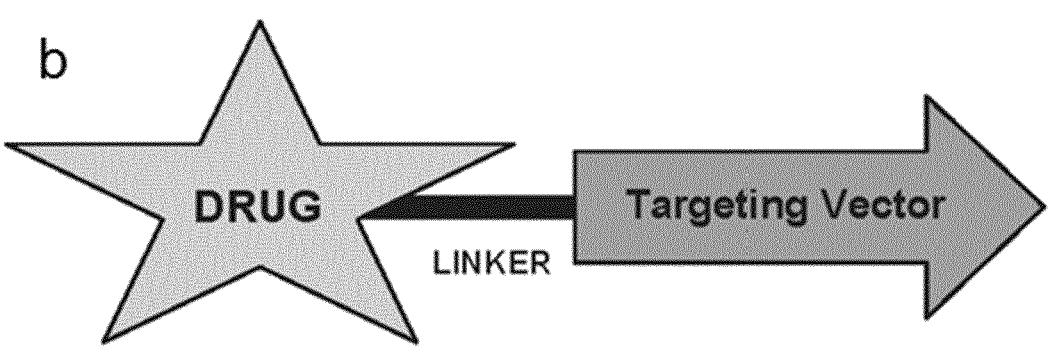
Figure 4:
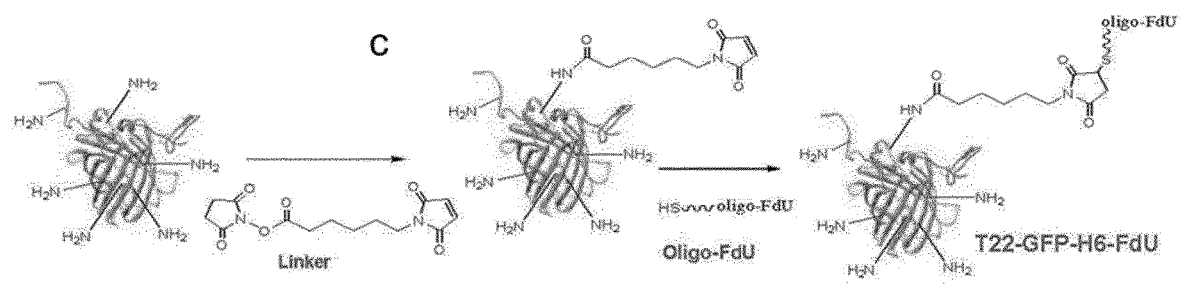
Figure 4:
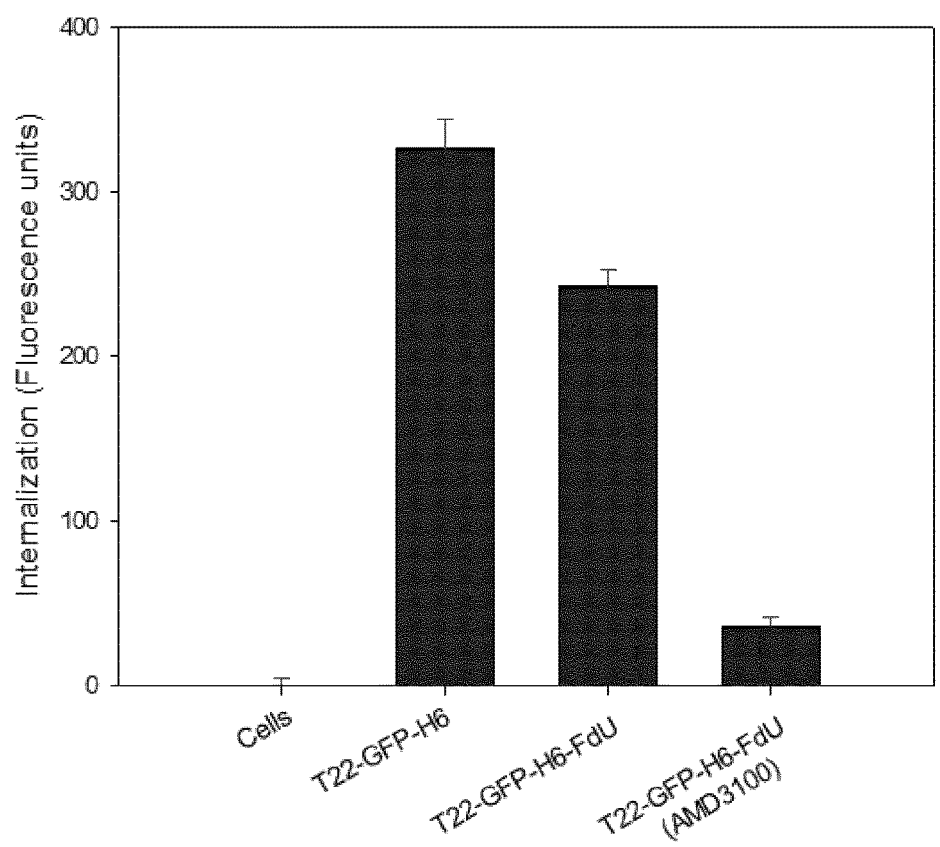

It has been previously demonstrated that CXCR4 overexpressing (CXCR4+) colorectal cancer (CRC) cells have metastasis initiation capacity (MIC) [Croker, A. K. & Allan, A. L. 2008. J Cell Mol Med 12, 374-390; Zhang, S. S. et al. 2012. BMC Med 10, 85 (2012)], and its inhibition by CXCR4 downregulation [Murakami, T. et al. 2012. BMC Med 10, 85; Wang, T. B. et al. 2014. Int J Oncol 44, 1861-1869] identifies these cells as metastatic stem cells (MetSCs). On this basis, the inventors generated a CXCR4-targeted nanoconjugate to evaluate if it could achieve antimetastatic effect by selectively eliminating CXCR4+ CRC cells. The structure and physicochemical characterization of this new T22-GFP-H6-FdU nanoconjugate is described in FIGS. 1, 2 and 4a-c. The conjugate contains T22 (a ligand that targets the CXCR4 receptor), a green fluorescent protein (allowing its in vivo follow-up) and oligo-FdU, an oligonucleotide of a drug active against CRC31, which allows to load a high number of drug molecules into the nanoconjugate. T22-GFP-H6-FdU was synthesized by functionalizing oligo-FdU with thiol (FIG. 4c and FIG. 1a), which was subsequently conjugated to a T22-GFP-H6 protein nanoparticle once bound to a chemical coupler (FIG. 4c). The inventors physico-chemically characterized the HS-oligo-FdU by HPLC, UV spectrometry and MALDI-TOF (FIG. 1b-e) and the final T22-GFP-H6-FdU product, by MALDI-TOF, dynamic light scattering (DLS) and Field Emission Scanning Electron Microscopy (FESEM) (FIG. 2a-c). This product had an approximate drug/nanoparticle (DNR) ratio of 40 (FIG. 2), a size slightly higher (14.66+0.14 nm) than T22-GFP-H6 and maintained its capacity for self-assembling (FIG. 2d). Moreover, its size was higher than the renal filtration cut-off (6-7 nm) ensuring a high recirculation time in blood, a requirement for effective targeted drug delivery.

Figure 13:
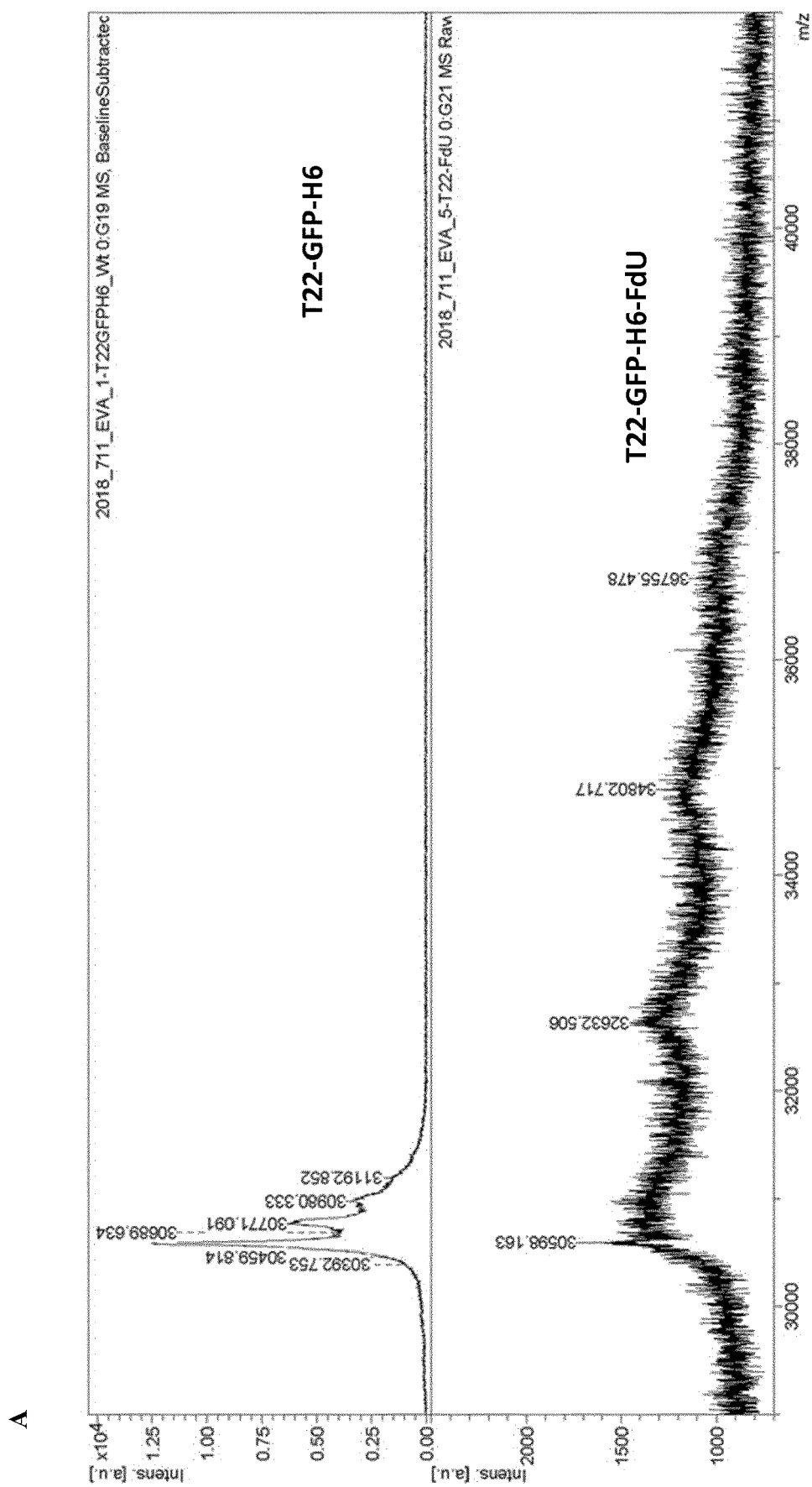
FIG. 13. Physicochemical characterization of the T22-GFP-116-FdU nanoconjugate and demonstration of selective internalization and killing of CXCR4$^+$ CRC cells in vitro. (A). Mass spectrometry of the initial T22-GFP-H6 protein and the T22-GFP-H6-FdU conjugates. (B) DLS of the T22-GFP-H6-FdU conjugate using inverted reaction. (C) Dose-response representation of CXCR4+ HeLa cells exposed to different concentration of T22-GFP-H6-FdU conjugates for 48 h, analyzed by MTT viability assay.
Figure 13:
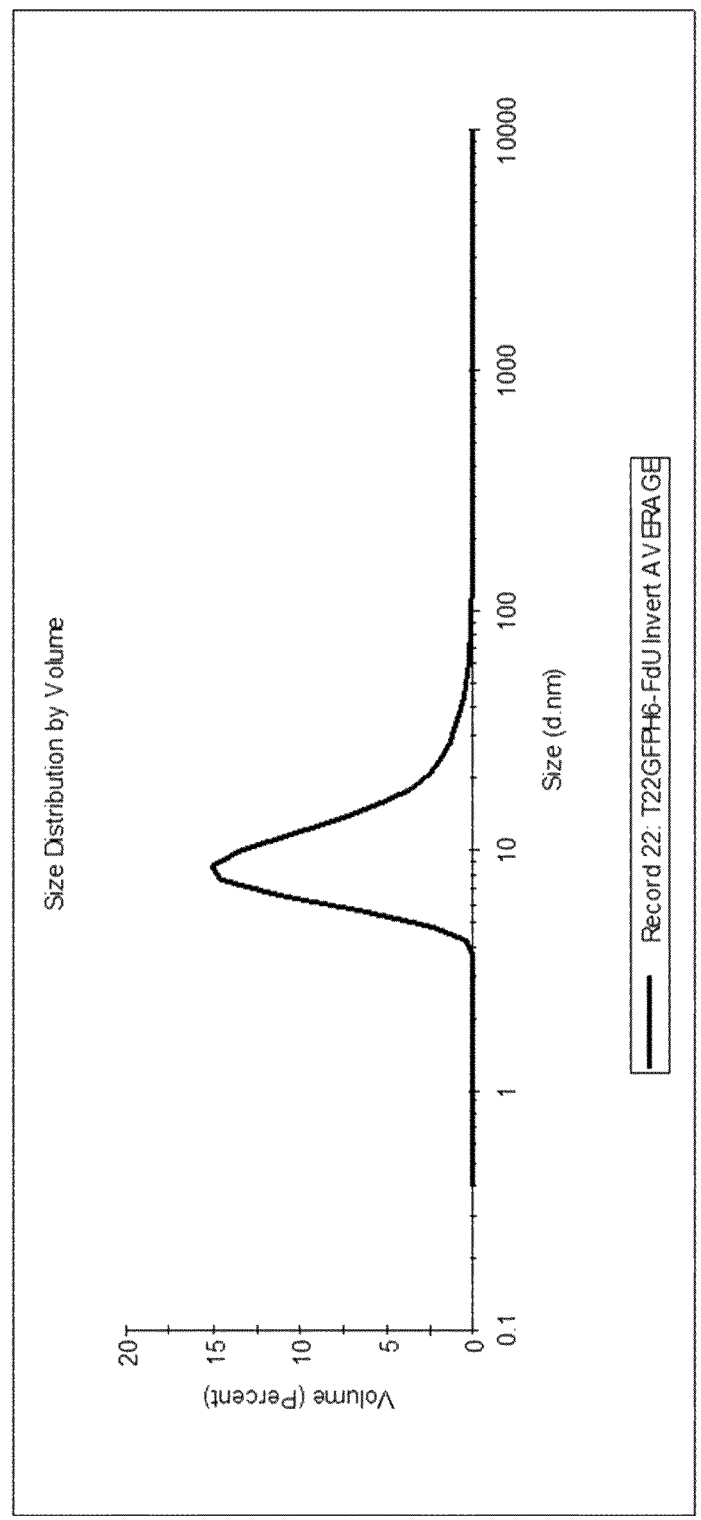
Figure 13:
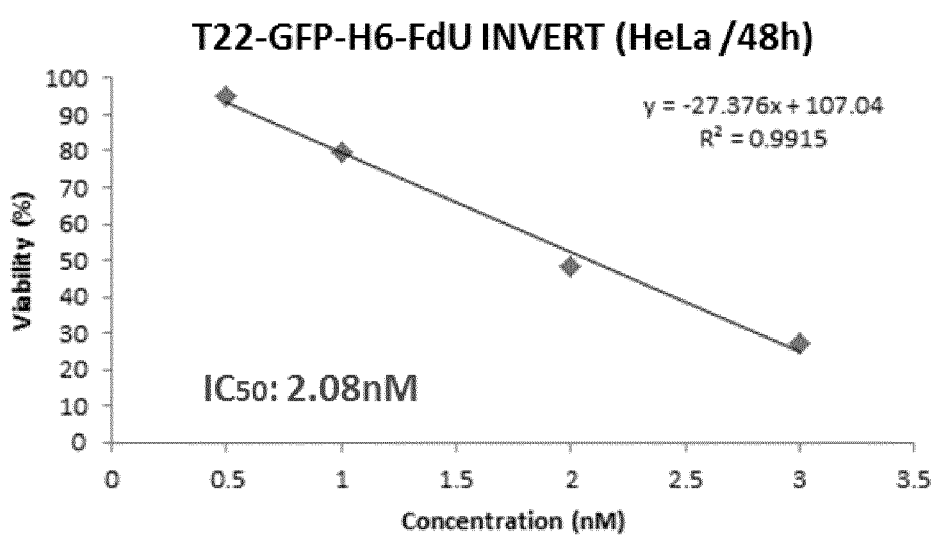

An inverted method was also used to produce T22-GFP-H6-FdU in which T22-GFP-H6 was first functionalized with a chemical coupler and then contacted with thiol-functionalized oligo-FdU. The conjugate obtained using this method (known as T22-GFP-H6-FdU INVERT) was then physicochemically characterized by MALDI-TOF and dynamic light scattering (DLS) (FIGS. 13A and B).

Example 4

T22-GFP-H6-FdU Selectively Internalizes and Kills CXCR4+ CRC Cells In Vitro

Figure 5:
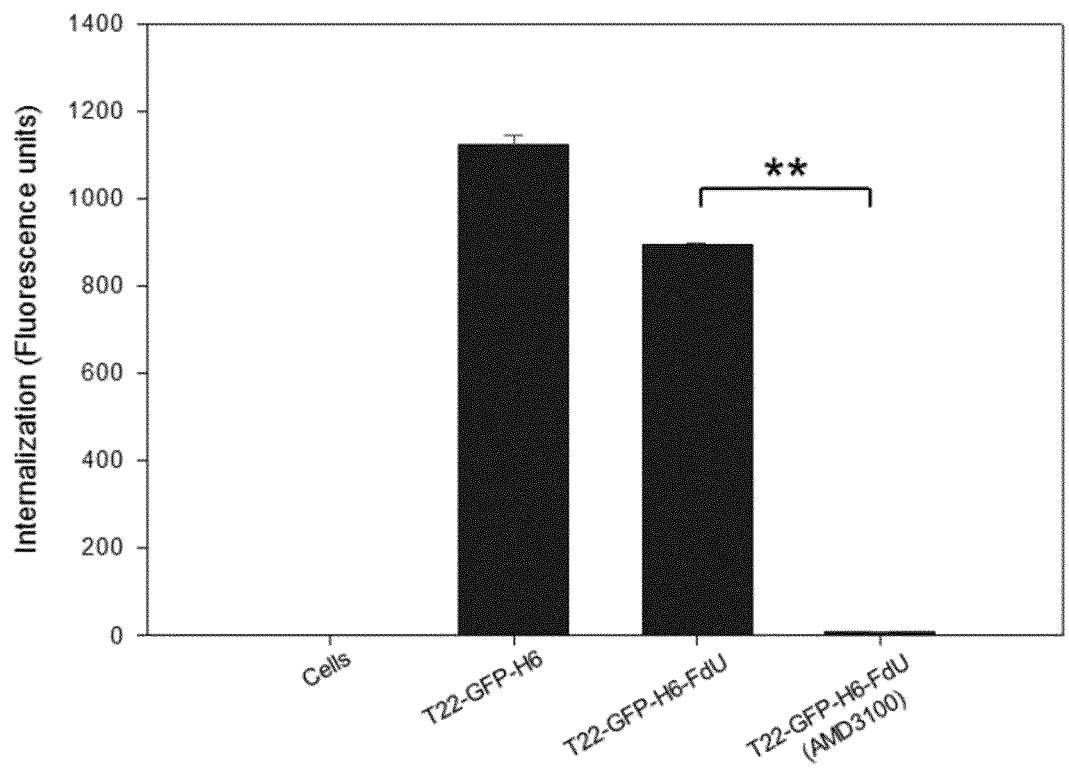
FIG. 5. T22-GFP-H6-FdU selectively internalizes and kills CXCR4$^+$ HeLa cells in vitro. (a) T22-GFP-H6-FdU nanoconjugate or T22-GFP-H6 internalization in HeLa cells detected as emitted fluorescence in by flow cytometry after 1 hour cell exposure at 1 µM concentration. Complete internalization block obtained by pre-treatment of cells with the CXCR4 antagonist ADMD3100. (b) Intracellular trafficking of T22-GFP-H6-FdU in HeLa cells by confocal microscopy after exposure at 1 µM for 24 h. (c) Linearized T22-GFP-H6-FdU dose-response trend line representation compared with free oligo-FdU exposure. Antitumor effect was measured as HeLa cell viability by MTT after 72 h exposure as the described concentrations. (d) Reduction of cell viability as recorded by optical microscope images of HeLa cells exposed to T22-GFP-H6-FdU nanconjugates for 48 h, as compared to T22-GFP-H6 or free oligo-FdU. Scale bar, 100 µm.
Figure 5:
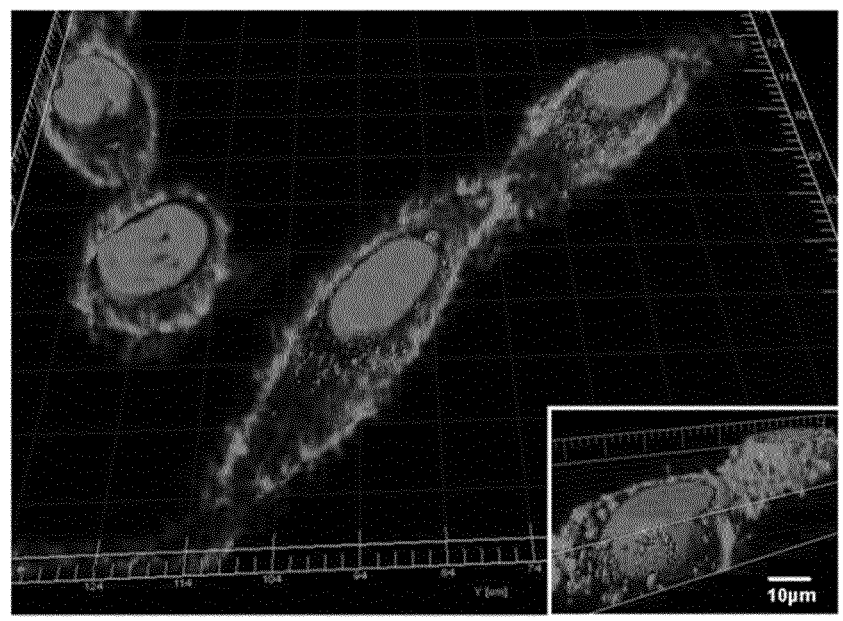
Figure 5:
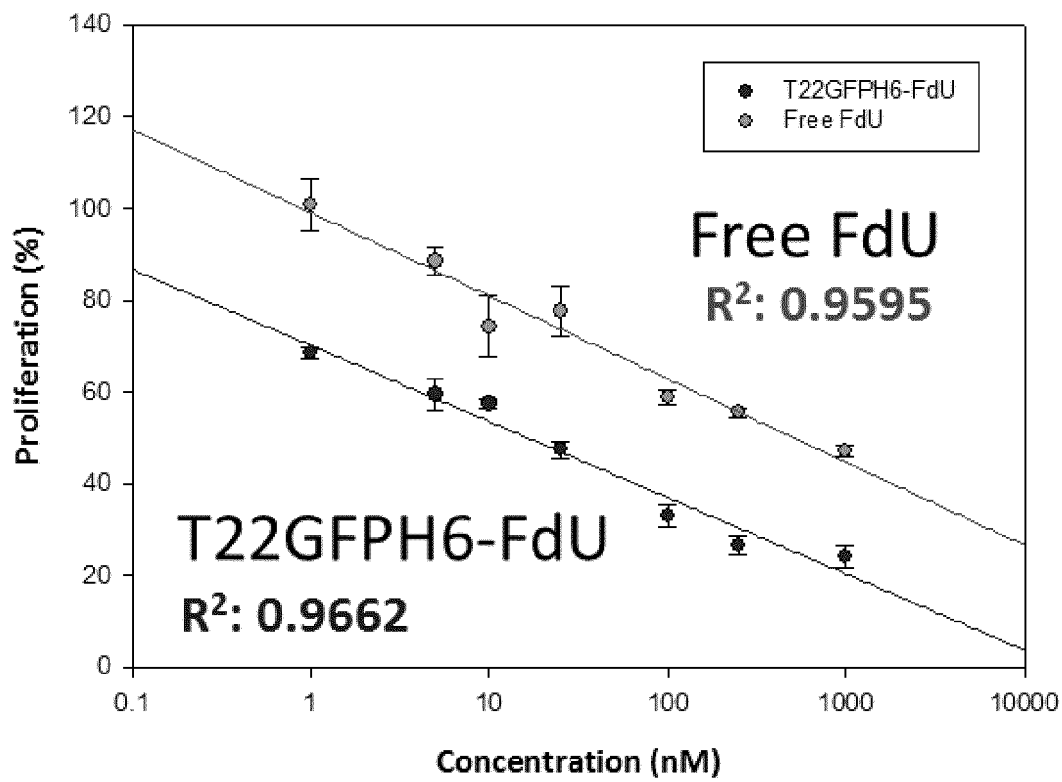
Figure 5:
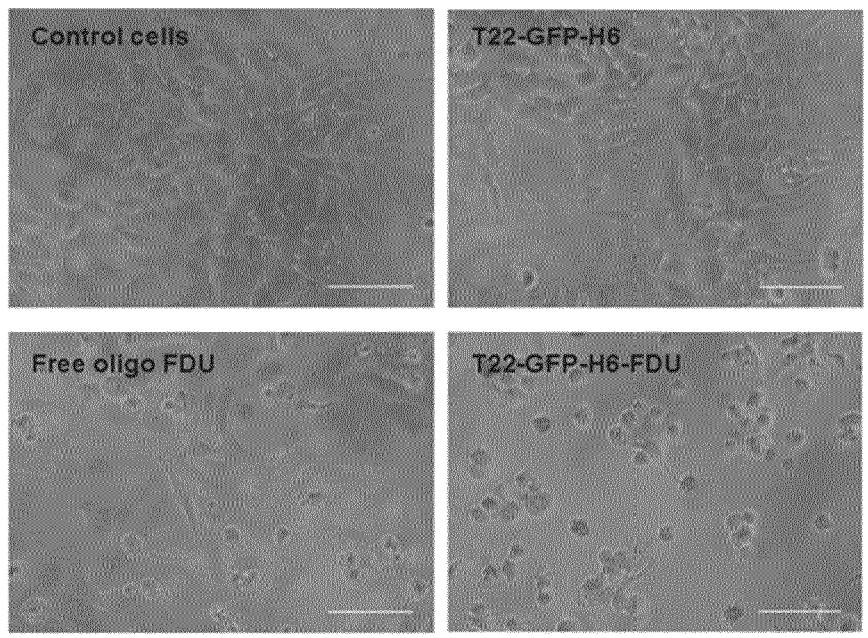

Following, the inventors assessed if the loaded oligo-FdU conferred the nanoparticle cytotoxic activity while maintaining its CXCR4 targeting capacity, provided that drug conjugation can alter protein conformation and function. T22-GFP-H6-FdU internalized in human CXCR4+ SW1417 CRC cells, as measured by fluorescence emission using flow cytometry, and accumulates and traffics in its cytosol, as observed by confocal microscopy (FIGS. 4d and 5a). The nanoconjugate maintains also its dependence on CXCR4 for internalization, since the AMD3100 CXCR4 antagonist was able to downregulate CXCR4 receptor in the membrane and completely blocked nanoconjugate internalization (FIG. 1d). In addition, T22-GFP-H6-FdU induced significantly higher cytotoxicity than free oligo-FdU in the same cells, as measured by cell viability or phase-contrast microscopy (FIG. 1g). The inventors confirmed CXCR4-dependent nanoconjugate internalization and higher cytotoxicity than free oligo-FdU in human CXCR4− HeLa cells (FIG. 5a-d).

The T22-GFP-H6-FdU INVERT conjugate obtained using the inverted method was also characterized in terms of its cytotoxic effect on of CXCR4+ HeLa cells (FIG. 13C).

Example 5

T22-GFP-H6-FdU Selectively Targets CXCR4+CRC Cells In Vivo

Figure 6:
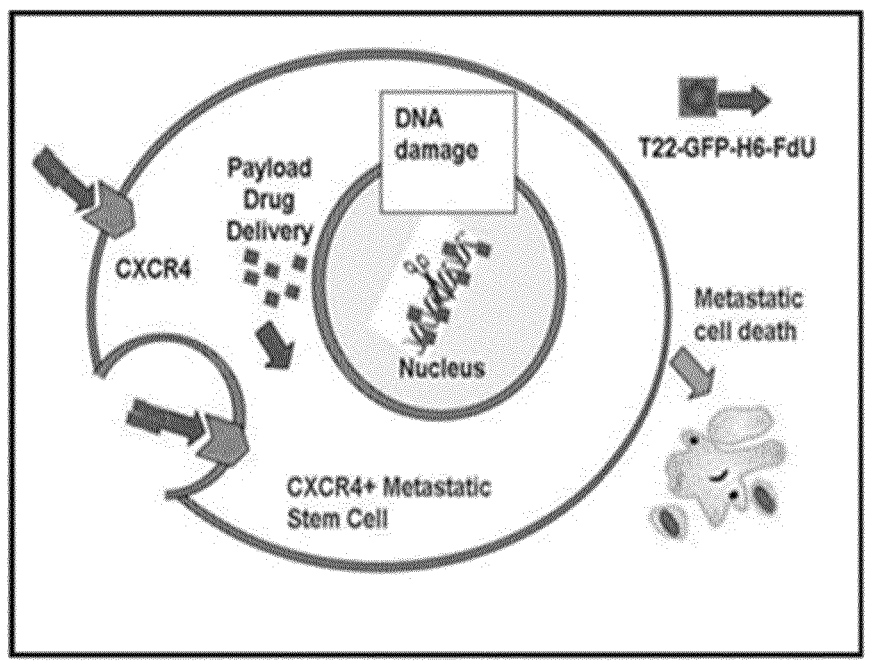
FIG. 6. Selective and receptor-dependent uptake of T22-GFP-H6-FdU in CXCR4$^+$ cells in vivo. (a) Approach to achieve targeted drug delivery and selective killing of metastatic stem cells: CXCR4-nanoconjugate interaction triggers CXCR4-mediated internalization in MetSCs, in primary tumors and metastatic foci, followed by FdU release to the cytosol and diffusion to the nucleus to induce double stand breaks leading to selective killing of CXCR4$^+$ cells. (b) Selective T22-GFP-H6-FdU nanoconjugate biodistribution in subcutaneous CXCR4$^+$ SW1417 CRC tumor tissue 5 h after a 100 µg single intravenous dose, as measured by fluorescence emission using IVIS Spectrum 200. Biodistribution is similar to that achieved by the T22-GFP-H6 targeting vector and undetectable after buffer or free oligo-FdU treatment. (c) Detection of T22-GFP-H6-FdU accumulation in tumor tissue, at a level similar to T22-GFP-H6, as measured by anti-GFP IHC. Absence of GFP detection in Buffer or free oligo-FdU controls. (d) Administration of the CXCR4 antagonist AMD3100 completely blocks T22-GFP-H6-FdU tumor biodistribution, as measured by fluorescence emission. Fluorescence is not detected in Buffer or free oligo-FdU controls. (e) The uptake of T22-GFP-H6-FdU observed in CXCR4$^-$ SW1417 tumor tissues is almost completely blocked by prior AMD3100 administration, as quantified using the anti-GFP IHC H-score. (f) Representative images of T22-GFP-H6-FdU uptake and AMD3100 competition by anti-GFP inmunostaining, which quantitation is reported in panel e. Scale bar, 50 µm.
Figure 6:
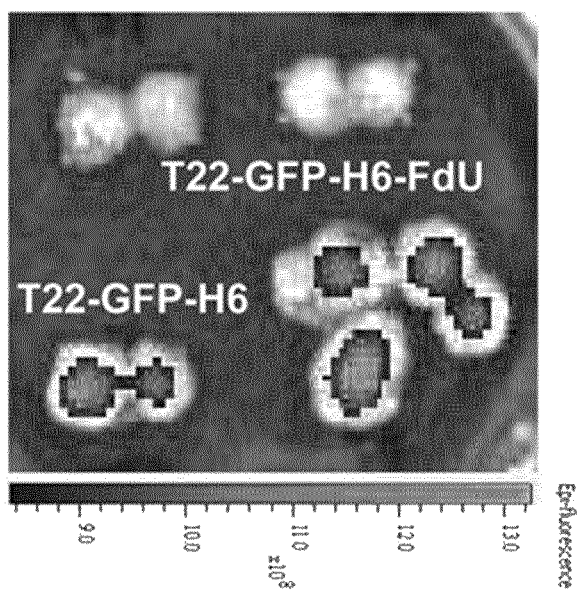
Figure 6:
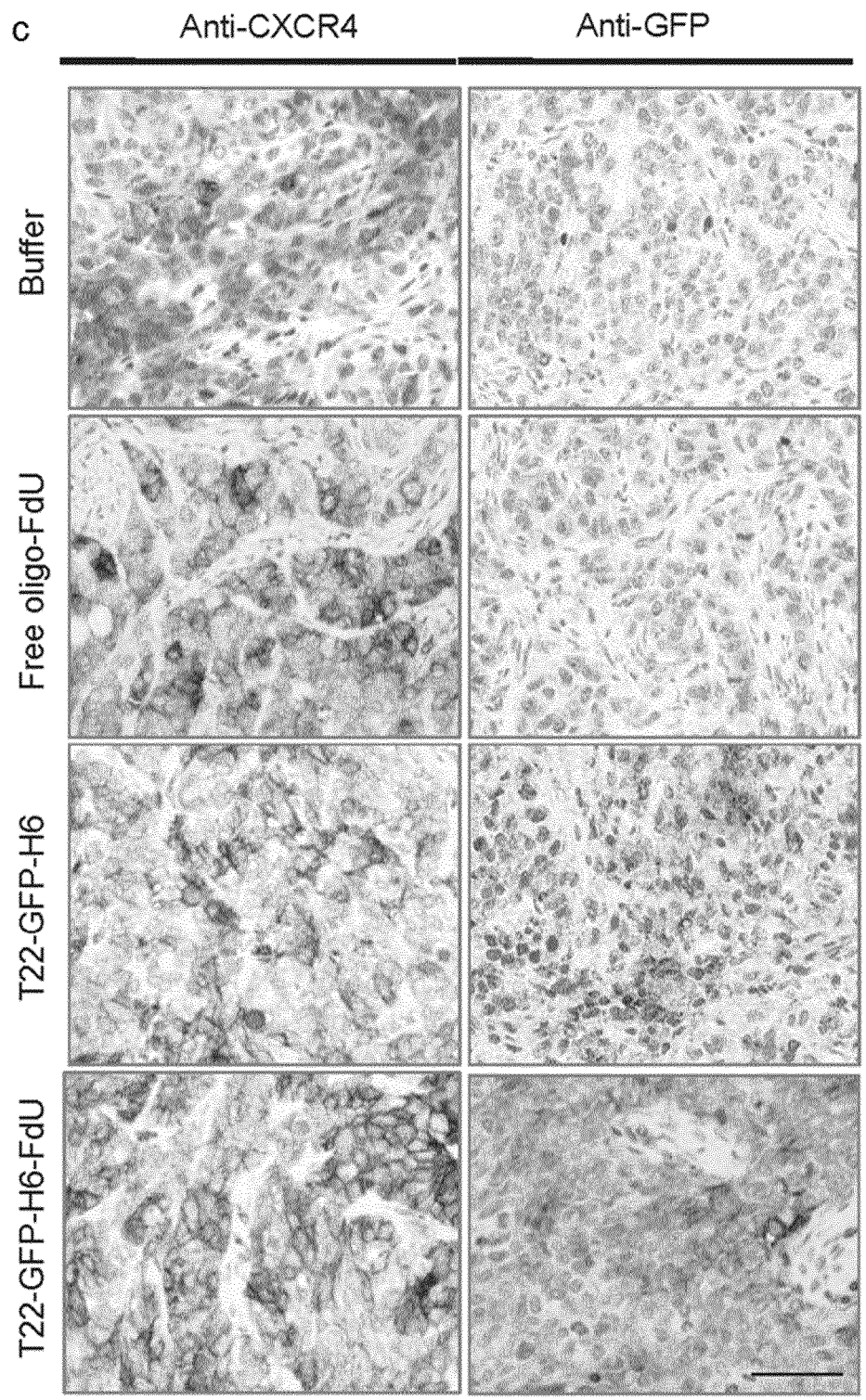
Figure 6:
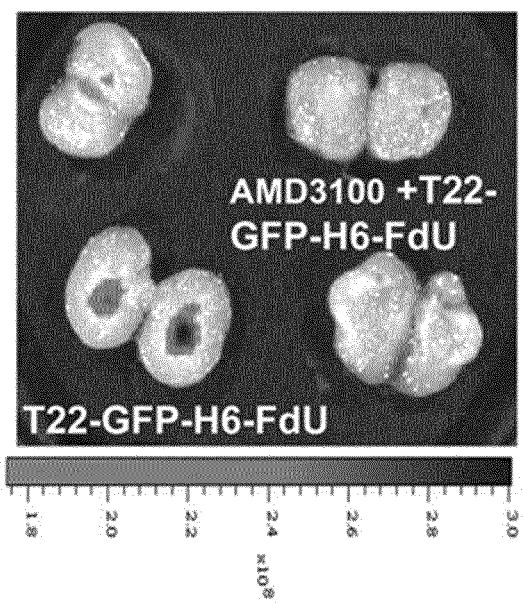
Figure 6:
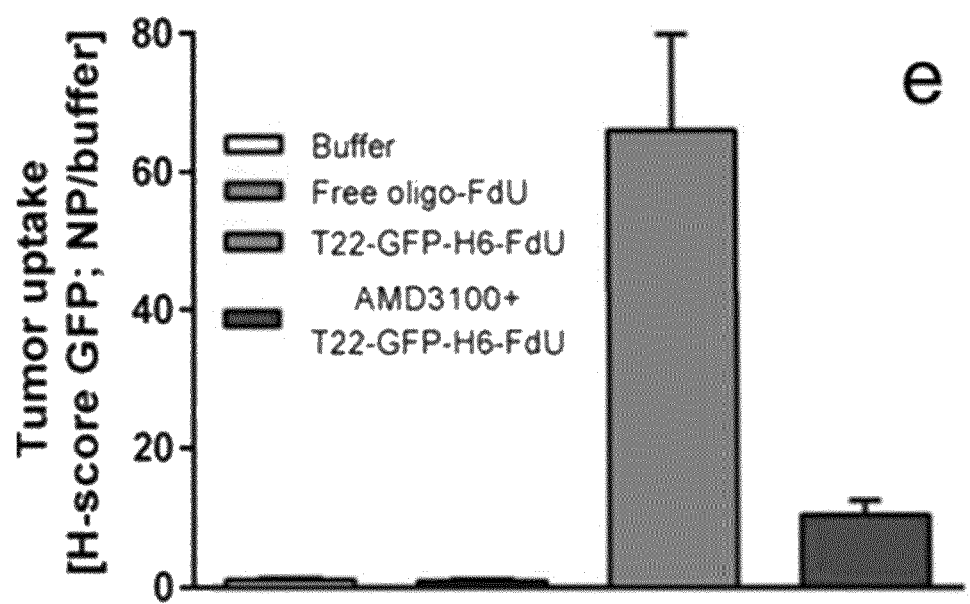
Figure 6:
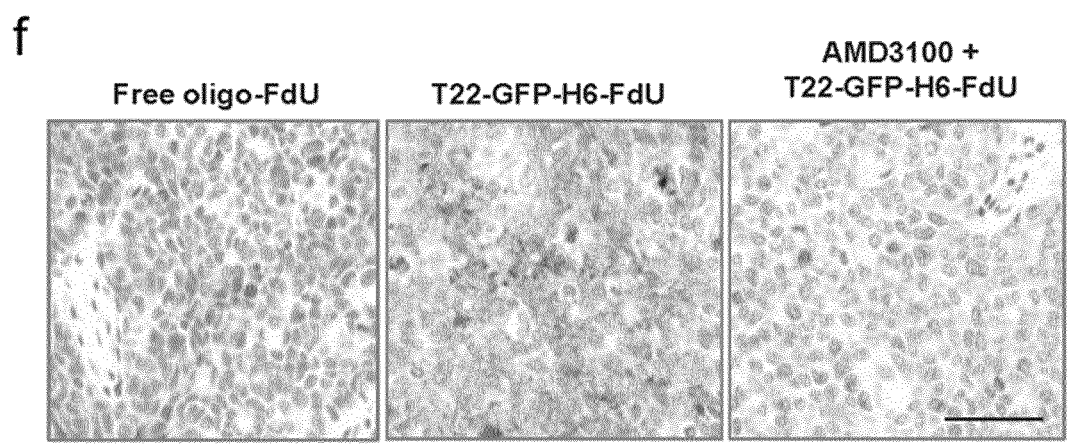

Once CXCR4-dependence for T22-GFP-H6-FdU in vitro activity was established, the inventors investigated in a subcutaneous (SC) CXCR4+ SW1417 CRC model if the nanoconjugate could achieve targeted drug delivery, after its intravenous administration, by assessing its selectivity and CXCR4-dependence regarding tumor tissue uptake, internalization in CXCR4 overexpressing MetSCs (target cells), intracellular release of the cytotoxic drug FdU and selective CXCR4+ MetSC killing (FIG. 6a). T22-GFP-H6-FdU showed selective tumor uptake, as measured by fluorescence emission, 5 h after the injection of a 100 mg dose in mice (FIG. 6b), as demonstrated for T22-GFP-H6 [Céspedes, M. V. et al. 2016. Nanomedicine. 12, 1987-1996.]. Moreover, both T22-GFP-H6-FdU and T22-GFP-H6 internalized into CXCR4+ tumor cell cytosol as measured by anti-GFP immunohistochemistry (FIG. 6c), a signal undetectable in buffer or free oligo-FdU negative controls. In addition, administering to mice the CXCR4 antagonist AMD3100 prior to the nanoconjugate completely blocked its tumor uptake (FIG. 6d) as well as its internalization in CXCR4− cancer cells (FIG. 6e-f). Therefore, the nanoconjugate achieves not only selective tumor biodistribution, but also its specific internalization into the cytosol of target CXCR4− cancer cells, in a CXCR4-dependent manner.

Example 6

Figure 7:
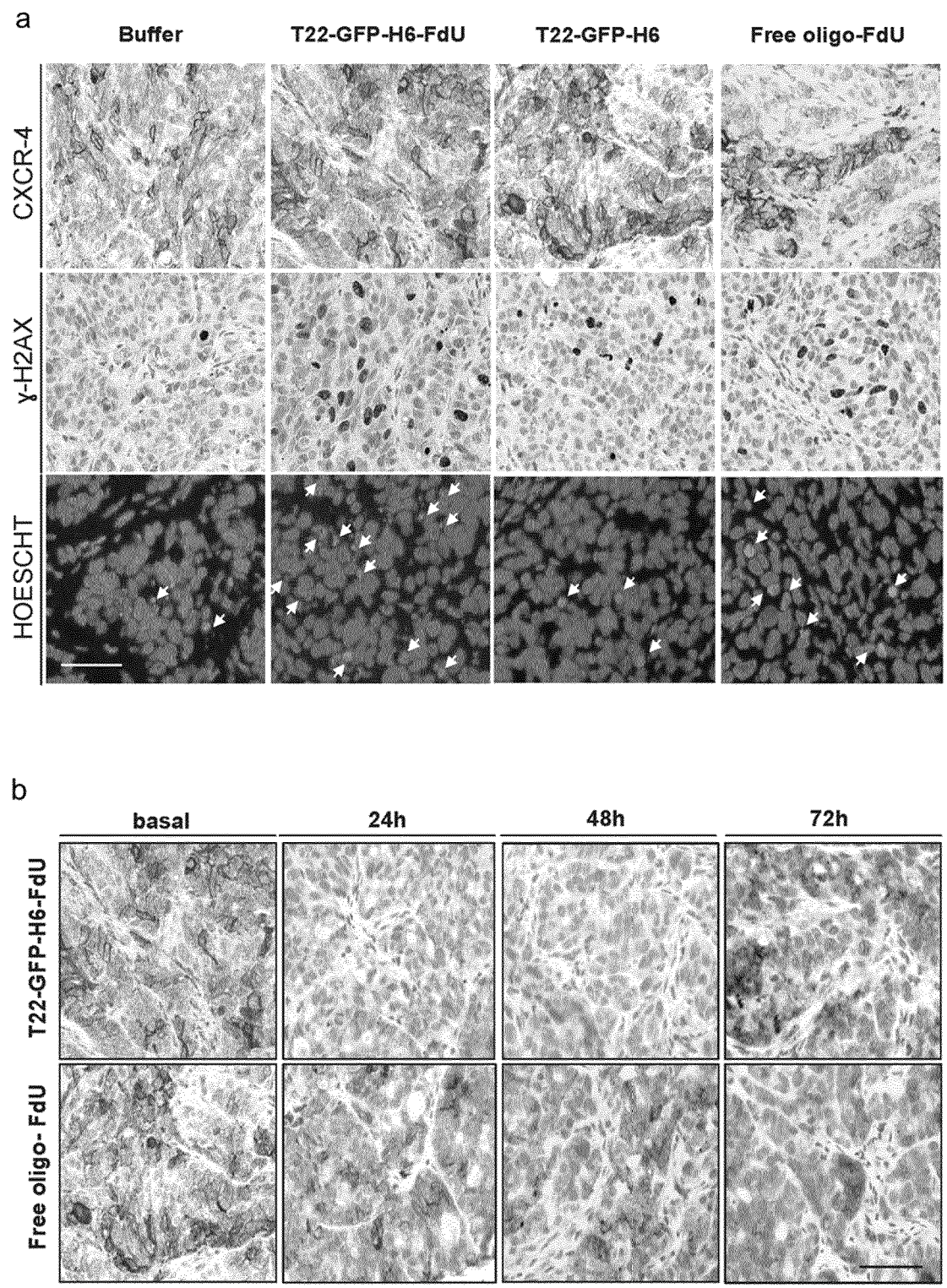
FIG. 7. T22-GFP-H6-FdU-induced depletion of CXCR4-overexpressing cancer cells in tumor tissue and definition of dosage interval. (a) Similar level of CXCR4 overexpression in subcutaneous tumor tissue among compared groups (Buffer, T22-GFP-H6-FdU, T22-GFP-H6 and free oligo-FdU) before treatment (upper panels). Representative images of DNA double-strand break induction (measured with anti-gH2AX IHC, 5 h post-administration, middle panels) and apoptotic induction (Hoechst staining, at 24 h, lower panels). Note the higher level of DSBs and apoptosis induction in the T22-GFP-H6-FdU as compared to free oligo-FdU. White arrows indicate apoptotic cells. (b) T22-GFP-H6-FdU depletes CXCR4$^+$ cancer cells from SW1417 CRC tumor tissue after a 100 µg single dose administration. Note the reduction in CXCR4$^+$ cell fraction in the tumor 24 h after injection, their complete elimination at 48 h and the re-emergence of CXCR4$^+$ cells 72 h post-administration, to reach a percent similar to the basal level, using anti-CXCR4 IHC. In contrast, the CXCR4$^+$ cancer cell fraction (CXCR4$^+$ CCF) in tumor tissue remains constant along time after free oligo-FdU treatment. The three day time-lapse for CXCR4$^+$ tumor cell re-appearance defines the dosage interval used in a repeated dose schedule of nanoconjugate administration in the experiments that evaluate its antimetastatic effect. Scale bar, 50 µm.

T22-GFP-H6-FdU Achieves Targeted Drug Delivery Leading to Selective Depletion of CXCR4+ CRC Cells in CRC Tumors Next the same SC CRC model was used to assess if the selective internalization into the cytosol of CXCR4+ target cancer cells achieved by the nanoconjugate leads to selective FdU delivery. The inventors also evaluated if the delivered FdU could induce DNA damage and apoptosis, triggering the specific elimination of CXCR4+ tumor cells, and if these effects differed from those achieved by free oligo-FdU. To that aim, H2AXg IHC was used to measure the generation of DNA double strand breaks (DSBs), since DSBs mediate FdU antitumor activity38. Five hours after T22-GFP-H6-FdU treatment the number of DSBs foci in tumors (22.8±1.4) was significantly higher p=0.02) than after free oligo-FdU (13.4±0.7), whereas DSBs were undetectable in T22-GFP-H6 or buffer-treated mice (FIG. 7a). T22-GFP-H6-FdU induction of DSBs indicated its capacity to release FdU in target cells to reach the nucleus and incorporate into DNA to induce DNA damage. Moreover, increased DSBs led to higher antitumor activity, since the number of apoptotic figures in tumor tissue, as measured by Hoechst nuclear condensation or defragmentation, 24 h after T22-GFP-H6-FdU injection (13.9±0.5) was significantly higher (p<0.05) than after free oligo-FdU (7.1±0.6), T22-GFP-H6 (3.0±0.3) or buffer (1.9±0.4) treatment (FIG. 7a).

Following, the fraction of CXCR4+ cancer cells (CXCR4+ CCF) remaining in tumor tissue was measured along time after a single 100 mg T22-GFP-H6-FdU dose, as compared to free oligo-FdU, using the SC CXCR4+ SW1417 CRC model. Before treatment, both groups showed a similar CXCR4+ CCF in tumor tissue (FIG. 7b); however, after T22-GFP-H6-FdU treatment the CXCR4+ CCF was reduced at 24 h and become undetectable at 48 h (FIG. 7b). Thus, 48 h post-administration T22-GFP-H6-FdU achieved selective elimination of CXCR4+ tumor cells in vivo. In contrast, the CXCR4+ CCF in tumor tissue after an equimolecular dose of free oligo-FdU remained similar to its basal level along time. Taken together, these results indicate that T22-GFP-H6-FdU achieves selective biodistribution to tumor tissue and FdU delivery to target CXCR4+ cancer cells, as indicated by an enhancement in DNA damage and tumor cell death, associated with selective elimination of CXCR4+ cancer cells, achieving, therefore, targeted FdU delivery to target cancer cells.

Example 7

Transient Target Cell Elimination and Definition of a Dose Interval for Repeated T22-GFP-H6-FdU Injection Despite T22-GFP-H6-FdU achieving selective depletion of CXCR4+ target cells in tumor tissue 48 h after its administration, this effect was found to be transient, since 72 h post-injection CXCR4+ cancer cell fraction in tumor tissue became similar to its level before therapy (FIG. 7b). In contrast, the CXCR4+ CCF in tumor tissue after free oligo-FdU therapy was maintained along time, remaining the same 24 h, 48 h or 72 h after treatment as before therapy (FIG. 7b). Therefore, in contrast to T22-GFP-H6-FdU effect, cancer killing by free oligo-FdU did not show selectivity towards CXCR4+ cancer cells. Based on these results, and in order to evaluate T22-GFP-H6-FdU antimetastatic effect, the inventors defined as optimal a 72 h (3 days) dose interval for its administration in a repeated dose schedule. It was expected that this schedule would maintain sufficiently low the fraction of CXCR4+ cancer cells (CXCR4+ CCF) remaining in primary tumors and metastatic foci, along the treatment period, so as to efficiently block metastatic dissemination and/or foci growth, provided that CXCR4+ cancer cells act as MetSCs. The T22-GFP-H6-FdU capacity to inhibit growth of established metastases was assessed by comparison to equimolecular doses of T22-GFP-H6 or free oligo-FdU by using an orthotopic bioluminescent CXCR4+ CRC model in Swiss nude mice, which generates Lymph node (LN) and lung metastases (FIG. 3a), and starting therapy 2 month after CRC cell implantation, at a 20 mg i.v. q3d dosage (FIG. 3b). The capacity of T22-GFP-H6-FdU to prevent metastasis, as compared to free oligo-FdU, was also assessed by using an orthotopic luminescent CXCR4− CRC NOD/SCID model, with improved metastatic efficiency and dissemination at the LN, liver, lung and peritoneum (FIG. 3c), which started dosing one week after CRC implantation (FIG. 3d).

Example 8

Figure 8:
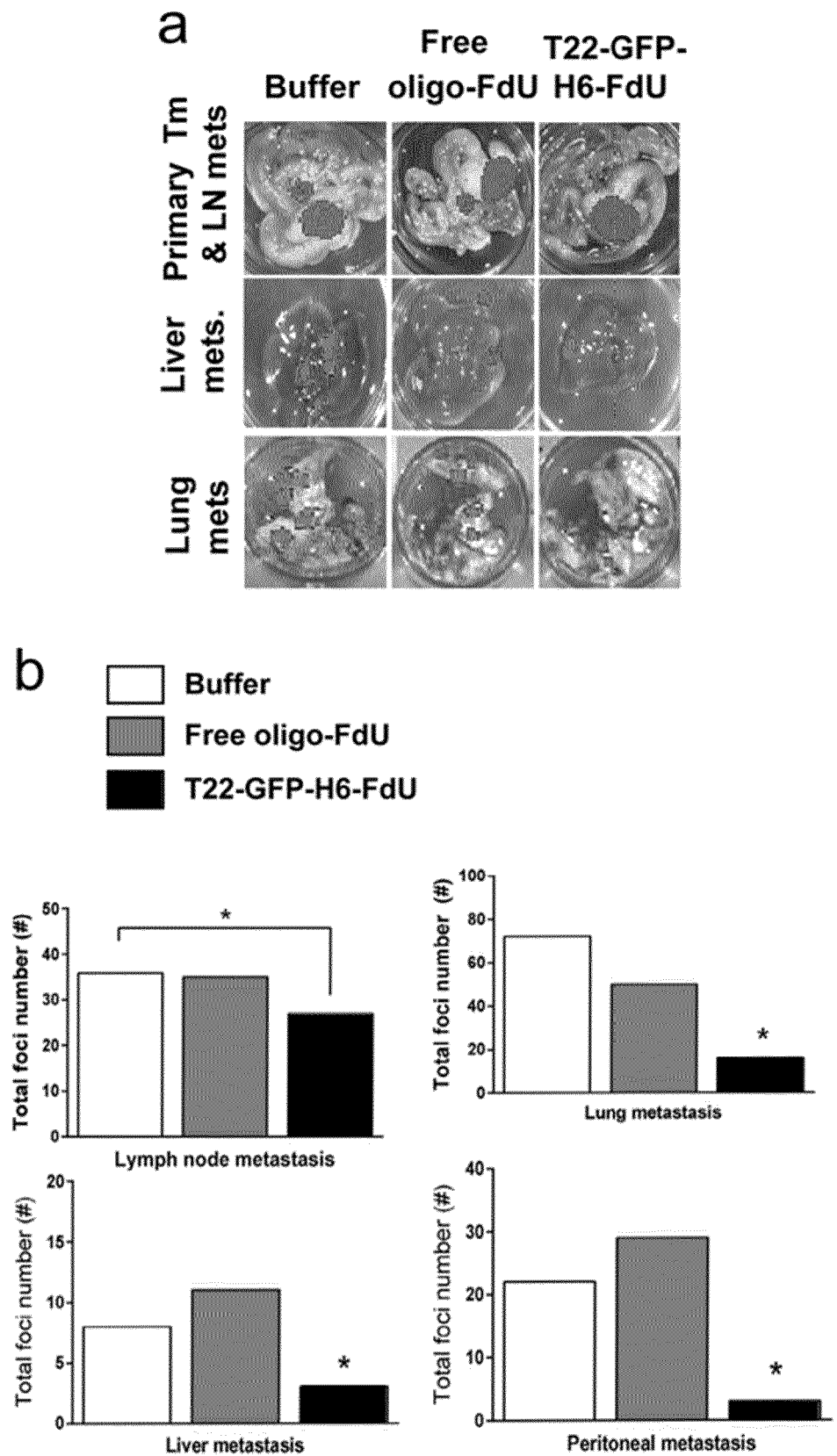
FIG. 8. T22-GFP-H6-FdU prevents metastasis in a CXCR4-dependent manner. (a) T22-GFP-H6-FdU blocks the appearance of bioluminescent lymph node (LN), liver and lung metastases (mets) in the CXCR4$^+$ SW1417 orthotopic model at the end of the prevention of metastases experiment as compared to free oligo-FdU. (b) T22-GFP-H6-FdU prevents metastases by potently reducing the total number of liver, lung and peritoneal mets, as recorded in H&E stained histology sections at the end of the prevention of metastasis experiment, in comparison to free oligo-FdU. In contrast, the number of LN mets is not reduced after T22-GFP-H6-FdU or free oligo-FdU administration *P<0.05, Mann-Withney test. See Table 1 for the results on nanoconjugate-induced reduction in mean foci number. (c) T22-GFP-H6-FdU induces a higher reduction of the remaining CXCR4$^+$ cancer cell fraction (CXCR4$^+$ CCF) in liver, lung and peritoneal metastatic tissue at the end of the experiment than free oligo-FdU, as measured by anti-CXCR4 IHC. In contrast, T22-GFP-H6 FdU or free oligo-FdU do not reduce the CXCR4$^+$ CCF remaining in LN mets or primary tumor tissue after therapy. (d) Representative images of the reduction in CXCR4$^+$ CCF induced by T22-GFP-H6-FdU or free oligo-FdU at the end of therapy, which quantitation is reported in panel c. Note the correlation between the reduction in CXCR4$^+$ CCF induced by T22-GFP-H6-FdU (panel c) and its antimetastatic effect at each metastatic site (panel b). Scale bar, 100 µm. Asterisks: tumor tissue; vL: lymphatic vessel, LN: lymphatic metastasis.
Figure 8:
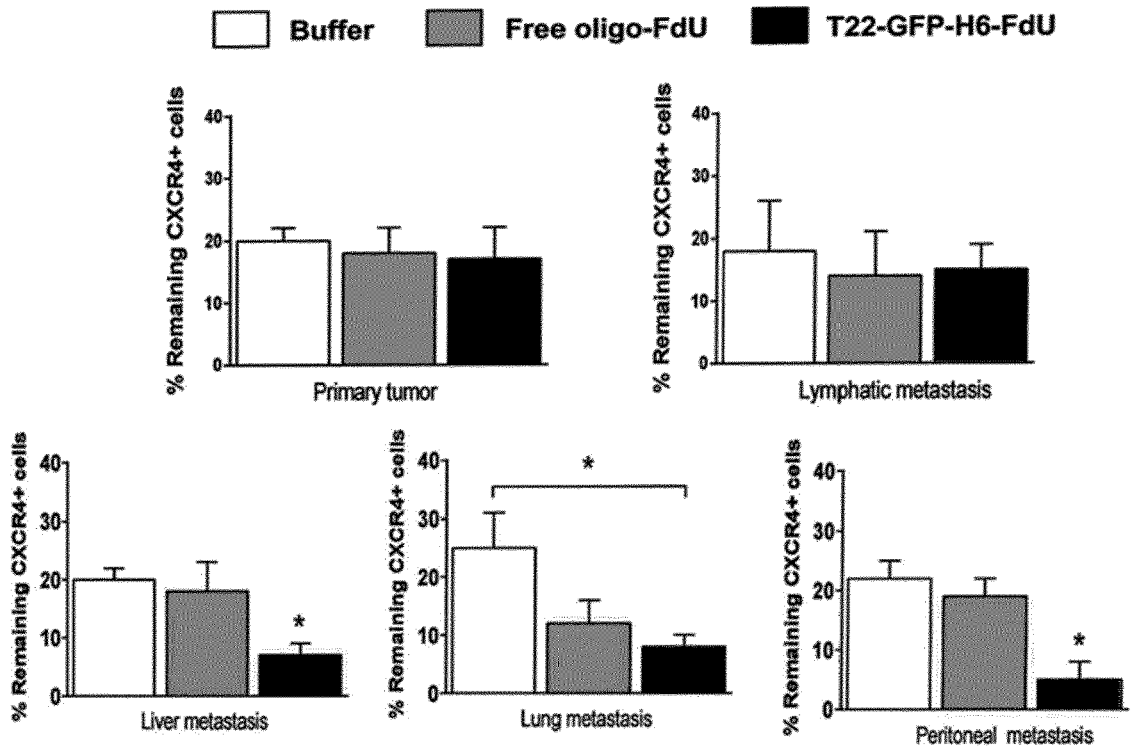
Figure 8:
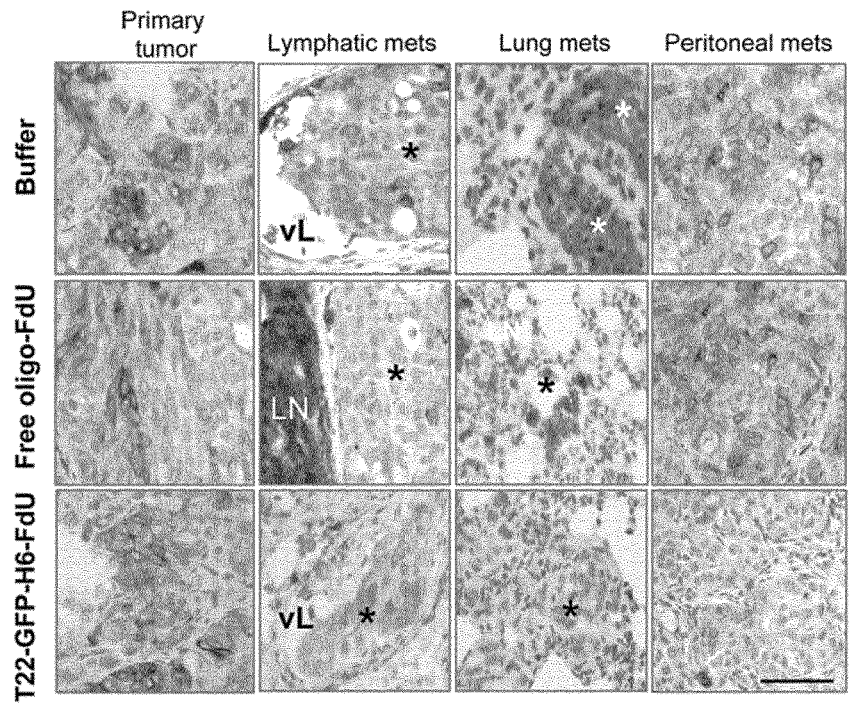

T22-GFP-H6-FdU Prevents Metastasis Development and Induces the Regression of Established Metastases At the end of the prevention of metastasis experiment, and in contrast to free oligo-FdU effect, T22-GFP-H6-FdU blocked metastasis development in liver and lung, as measured by ex vivo luminescence (FIG. 8a). At the end of the experiment, a histological analysis showed that T22-GFP-H6-FdU-treated mice had a 10.3 fold reduction in the total number of metastases in the peritoneum (p=0.0001) and 3.1-3.7 times reduction in liver (p=0.001) or lung (p=0.006) than free oligo-FdU mice, whereas it did not prevent LN metastases (FIG. 8b). Similar results were obtained when comparing the mean foci number at the peritoneum, liver or lung per mouse between both groups (Table 1).

TABLE 1

T22-GFP-H6-FdU antimetastatic effect in the prevention and regression of metastases experiments, measured as reduction in mean foci number per mouse

| Prevention of Metastasis Protocol | | | | |
|---|---|---|---|---|
| Groups | LN foci | Liver foci | Lung foci | Peritoneal foci |
| Buffer | $3.7 \pm 0.3^{a}$ | $0.7 \pm 0.3^{b}$ | $6.6 \pm 1.5^{d}$ | $2.0 \pm 0.6^{f}$ |
| Free oligo-FdU | $3.1 \pm 0.4$ | $1.0 \pm 0.3^{c}$ | $4.5 \pm 1.6^{e}$ | $2.8 \pm 1.0^{g}$ |
| T22-GFP-H6-FdU | $2.0 \pm 0.4^{a}$ | $0.2 \pm 0.1^{b,c}$ | $1.3 \pm 0.9^{d,e}$ | $0.4 \pm 0.3^{f,g}$ |

| Regression of Metastasis Protocol | | |
|---|---|---|
| Groups | LN foci | Lung foci |
| Buffer | $1.0 \pm 0.3^{h}$ | $4.0 \pm 1.1^{j,k}$ |
| T22-GFP-H6 | $1.1 \pm 0.2^{i}$ | $1.7 \pm 0.6^{l}$ |
| Free oligo-FdU | $0.8 \pm 0.2$ | $2.0 \pm 0.7^{j,m}$ |
| T22-GFP-H6-FdU | $0.4 \pm 0.1^{h,i}$ | $0.7 \pm 0.4^{k,l,m}$ |

Mean + SE metastatic foci number per mouse counted in 3 randomly chosen histology sections
free-oligo-FdU: equimolecular doses of free oligo-FdU
$^{a}$p = 0.04; $^{b}$p = 0.01; $^{c}$p = 0.001; $^{d}$p = 0.002, $^{e}$p = 0.006; $^{f}$p = 0.002; $^{g}$p = 0.006.
See Table 2 for nanoconjugate-induced reduction in mean foci size.
Mean + SE foci number per mouse counted in 6 randomly chosen histology sections
free-oligo-FdU: equimolecular doses of free oligo-FdU
$^{h}$p = 0.03; $^{i}$p = 0.01; $^{j}$p = 0.04; $^{k}$p = 0.03, $^{l}$p = 0.03; $^{m}$p = 0.04

Importantly, in contrast to T22-GFP-H6-FdU, free oligo-FdU did not reduce the total (FIG. 8b) or mean (Table 1) foci number at any site (LN, liver, lung, peritoneum), as compared to buffer-treated animals. Moreover, T22-GFP-H6-FdU induced also a 2.4 fold reduction in the size of peritoneal foci as compared to free oligo-FdU (p=0.01) (Table 2).

TABLE 2

Number of mice bearing metastatoic foci at the end of the prevention of Metastasis experiment in T22-GFP-FdU, free oligo-FdU o buffer-treated mice and size of the observed metatstic foci

| Group | Primary tumor Positive/ #Mice [%] | Metastasis | | | |
|---|---|---|---|---|---|
| | | Lymph nodes | Liver | Lung | Peritoneal |
| Buffer | 11/11 [100] | 11/11 [100] | 4/11 [36] | 8/11 [73][b] | 7/11 [64][d] |
| Free oligo-FdU | 11/11 [100] | 11/11 [100] | 6/11 [55][a] | 6/11 [55][c] | 5/11 [45] |
| T22-GFP-FdU | 12/12 [100] | 9/12 [75] | 2/12 [17][a] | 2/12 [17][b,c] | 2/12 [17][d] |

| | Metastasis Size[&] ($\mu m^2 \times 10^{-3}$) | | | |
|---|---|---|---|---|
| Buffer | 110.7 ± 15.5[e] | 11.2 ± 3.4 | 21.2 ± 1.3[f] | 435.7 ± 67.2[g] |
| Free oligo-FdU | 77.0 ± 14.2[e] | 9.6 ± 2.3 | 17.9 ± 1.6 | 304.8 ± 22.3[h] |
| T22-GFP-FdU | 79.3 ± 11.1 | 8.7 ± 2.6 | 15.1 ± 2.2[f] | 126.6 ± 18.7[g,h] |

*number of mice bearing a primary tumor out of the total mice per group
**number of mice affected by metastases out of the total number of mice per group
[&]mean + SE metastic foci size
[a]p = 0.05; [b]p = 0.012; [c]p = 0.05; [d]p = 0.036; [e]p = 0.009; [f]p = 0.032; [g]p = 0.002; [h]p = 0.01
See Table 1 for the reduction of total number of foci induced by T22-GFP-FdU, free olgigo-FdU or Buffer At the end of the regression of metastasis experiment, T22-GFP-H6-FdU-treated mice registered a lower number of lung metastasis, as measured by ex vivo luminescence emission (FIG. 9a) or a reduction in total lung foci count, in histology sections, than free-oligo-FdU (p=0.04), T22-GFP-H6 (p=0.03), or buffer (p=0.03) treated mice (FIG. 9b). Similar results were obtained when comparing the mean of lung foci number per mouse among groups (Table 1). T22-GFP-H6-FdU-treated mice registered also a significantly lower number of lymph node metastasis than buffer-treated (p=0.03); however, its effect was similar to that achieved by free oligo-FdU (FIG. 9b and Table 1).

Figure 10:
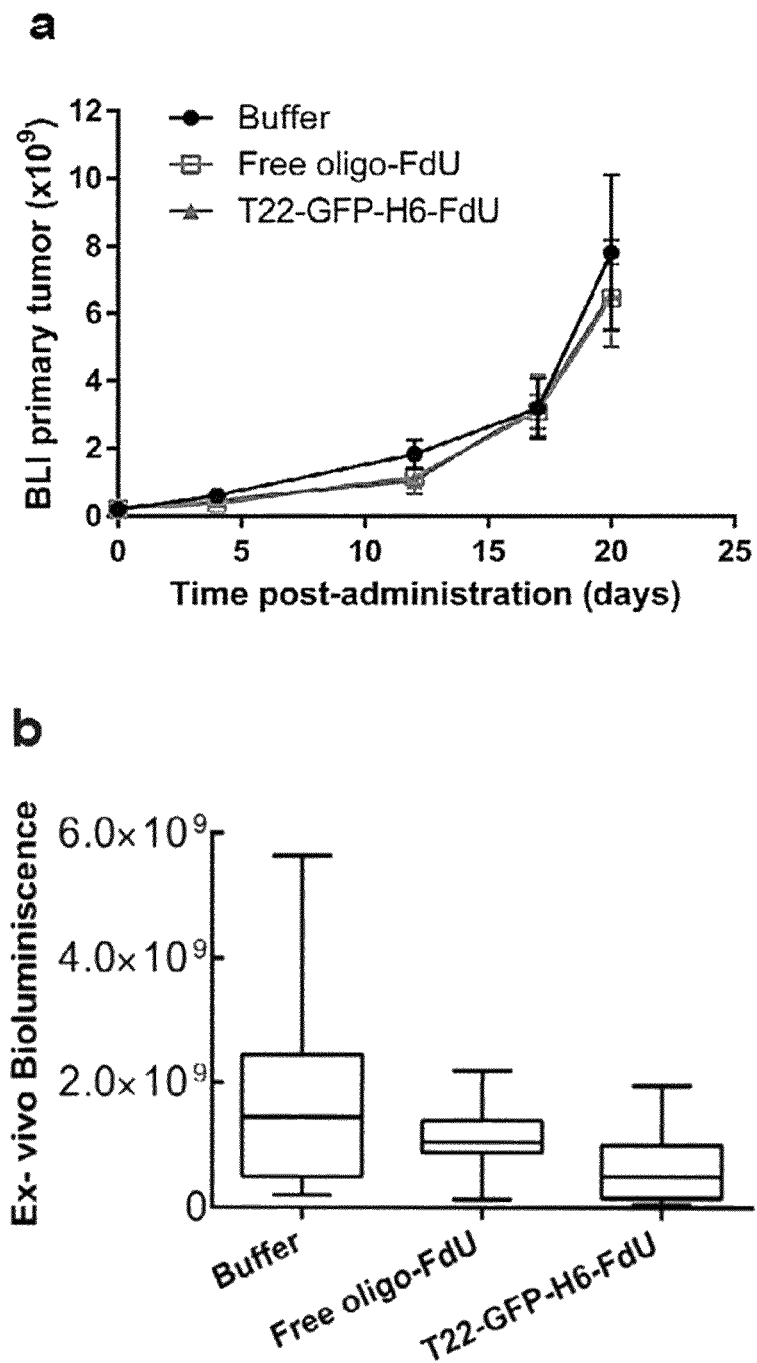
FIG. 10. T22-GFP-116-FdU inhibition of primary tumor growth. (a) In 78 the prevention of metastasis experiment, no significant inhibition in primary tumor growth was observed along the experimental time, as measured by in vivo bioluminescence emission, after T22-GFP-H6-FdU or free oligo-FdU treatment, as compared to buffer-treated mice. (b) Ex vivo recording of bioluminescene emitted by the primary tumor after its resection at the end of the experiment showed also similar levels among T22-GFP-H6-FdU, free oligo-FdU and Buffer-treated mice. (c) In the regression of established metastasis experiment, T22-GFP-H6-FdU inhibited primary tumor growth along the experimental time, as detected by in vivo bioluminescence emission (BLI), to levels similar to these achieved by free oligo-FdU. Both compounds significantly inhibited tumor growth as compared to buffer treated animals. (d) Ex vivo recording of bioluminescence emitted by the primary tumor, after its resection at the end of the experiment, showed also similar levels between the T22-GFP-H6-FdU and free oligo-FdU mice. Note that in contrast to registering a similar response of the primary tumor to T22-GFP-H6-FdU or free-oligo-FdU treatment, the anitmetastatic effect induced by T22-GFP-H6-FdU was significantly higher than that observed after free-oligo-FdU treatment, especially regarding metastasis prevention (see FIG. 4 and Table 1).
Figure 10:
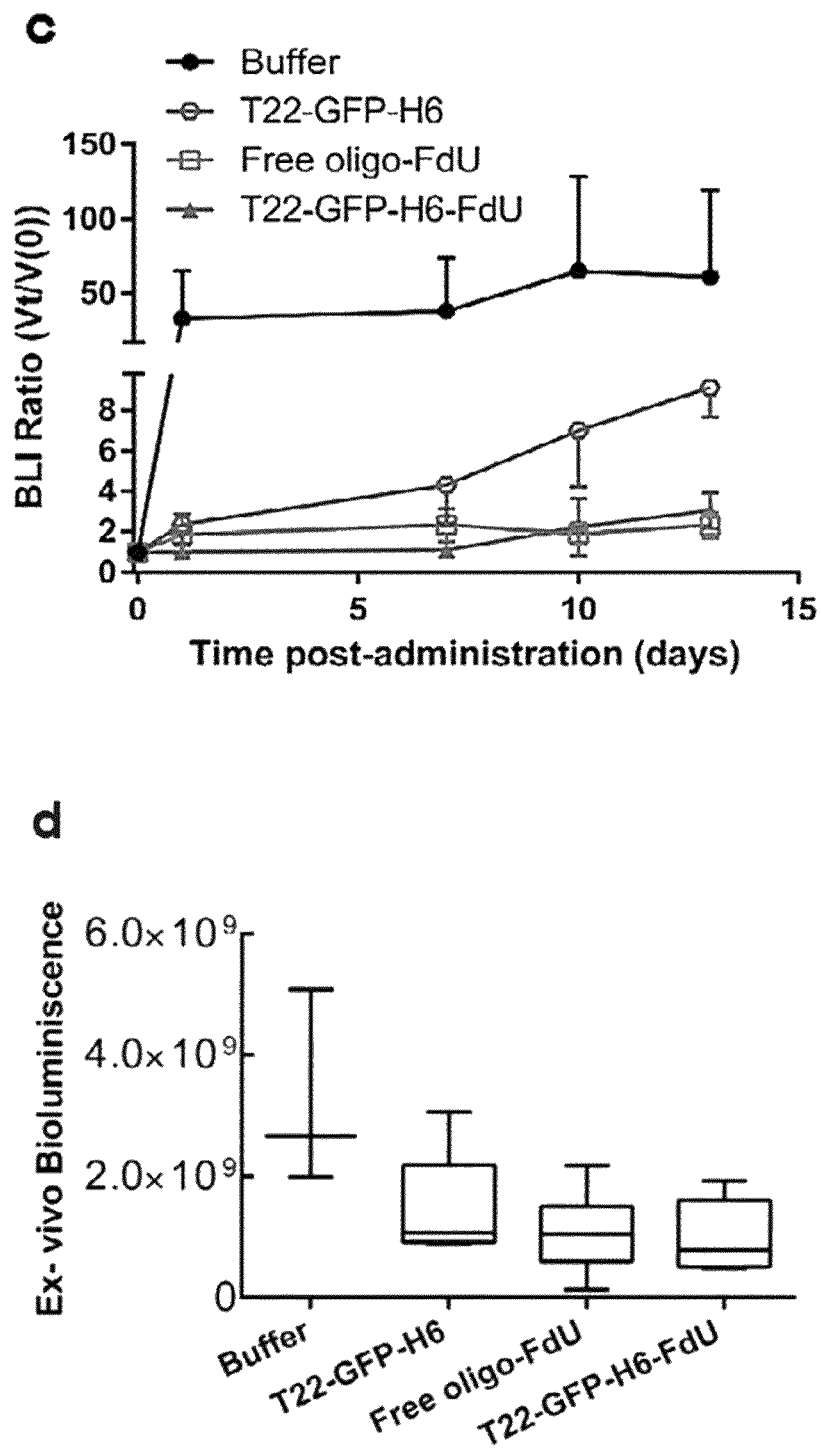

In summary, repeated T22-GFP-H6-FdU administration potently prevented metastasis development in peritoneum, liver and lung, whereas free oligo FdU did not prevent metastasis at any site. In addition, T22-GFP-H6-FdU was more potent than free oligo-FdU in inducing the regression of established lung metastasis. Interestingly, both T22-GFP-H6-FdU and free oligo-FdU showed a similar inhibitory effect on primary tumor growth as measured by luminescence emission in vivo along time or ex vivo at the end of the experiment, in the prevention (FIG. 10a,b) or regression 193 (FIG. 10c,d) of metastasis experiments.

Example 9

Figure 9:
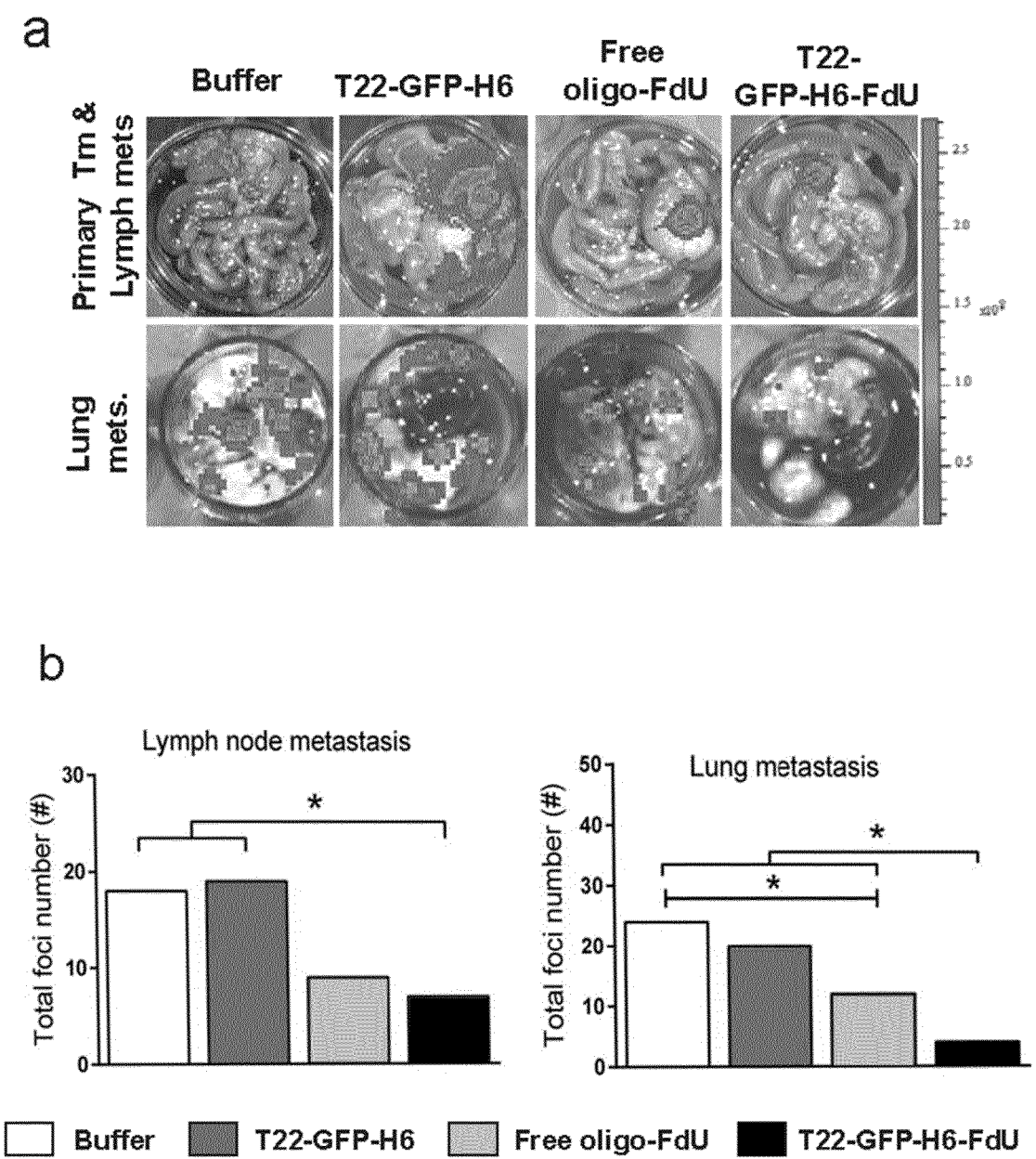
FIG. 9. T22-GFP-116-FdU induces the regression of established metastases in a CXCR4-dependent manner. (a) T22-GFP-H6-FdU shows a higher inhibition of lung mets than free oligo-FdU, as measured by bioluminescence emission at the end of the regression of metastases experiment, whereas both compounds show a similar level of inhibition of LN mets in the CXCR4+ SW1417 orthotopic model. (b) T22-GFP-H6-FdU shows a higher reduction in the number of Lung mets than free oligo-FdU as recorded in H&E stained tissue sections at the end of the regression of metastasis experiment, whereas both compounds show a similar level of inhibition of LN mets.

Site-Dependent CXCR4 Regulation, T22-GFP-H6-FdU CXCR4+ Cell Targeting and Antimetastatic Effect Based on the clear site-dependent antimetastatic potency achieved by T22-GFP-H6-FdU in the prevention of metastasis experiment (FIG. 8b and Table 1), on its dependence on CXCR4 membrane expression for cell internalization (FIG. 2e) and on its capacity to selectively kill CXCR4+ cancer cells (FIG. 7a,b and FIG. 5a), the inventors investigated if CXCR4 expression registered after therapy correlated with the observed antimetastatic effect at the different sites. A site-dependent reduction in CXCR4− CCF in metastatic foci at the end of the experiment was observed though detection with anti-CXCR4 IHC (as compared to basal levels), and nanoconjugate sensitivity, being higher in peritoneum, intermediate in liver and lung and non-existent in unresponsive lymph node metastases (FIG. 8c-d), which correlated with the antimetastatic effect at the different sites (FIG. 8b). In contrast to T22-GFP-H6-FdU-induced metastatic control, free oligo-FdU does not reduce CXCR4− CCF (FIG. 8c) and seems to increase rather than decrease the number of metastases at the end of treatment in liver and peritoneum, as compared with buffer-treated mice (FIG. 8b and Table 1). Similarly, in the regression of metastasis experiment, the inventors observed a reduction in the CXCR4+ CCF in lung metastatic foci at the end of the experiment (FIG. 9c) and higher antimetastatic effect at this site (FIG. 9b) than in lymph node foci, which show no reduction in CXCR4+ CCF and poor response to T22-GFP-H6-FdU therapy (FIG. 9 and Table 1).

Example 10

Lack of T22-GFP-H6-FdU Accumulation or Toxicity in Normal Tissues

Figure 11:
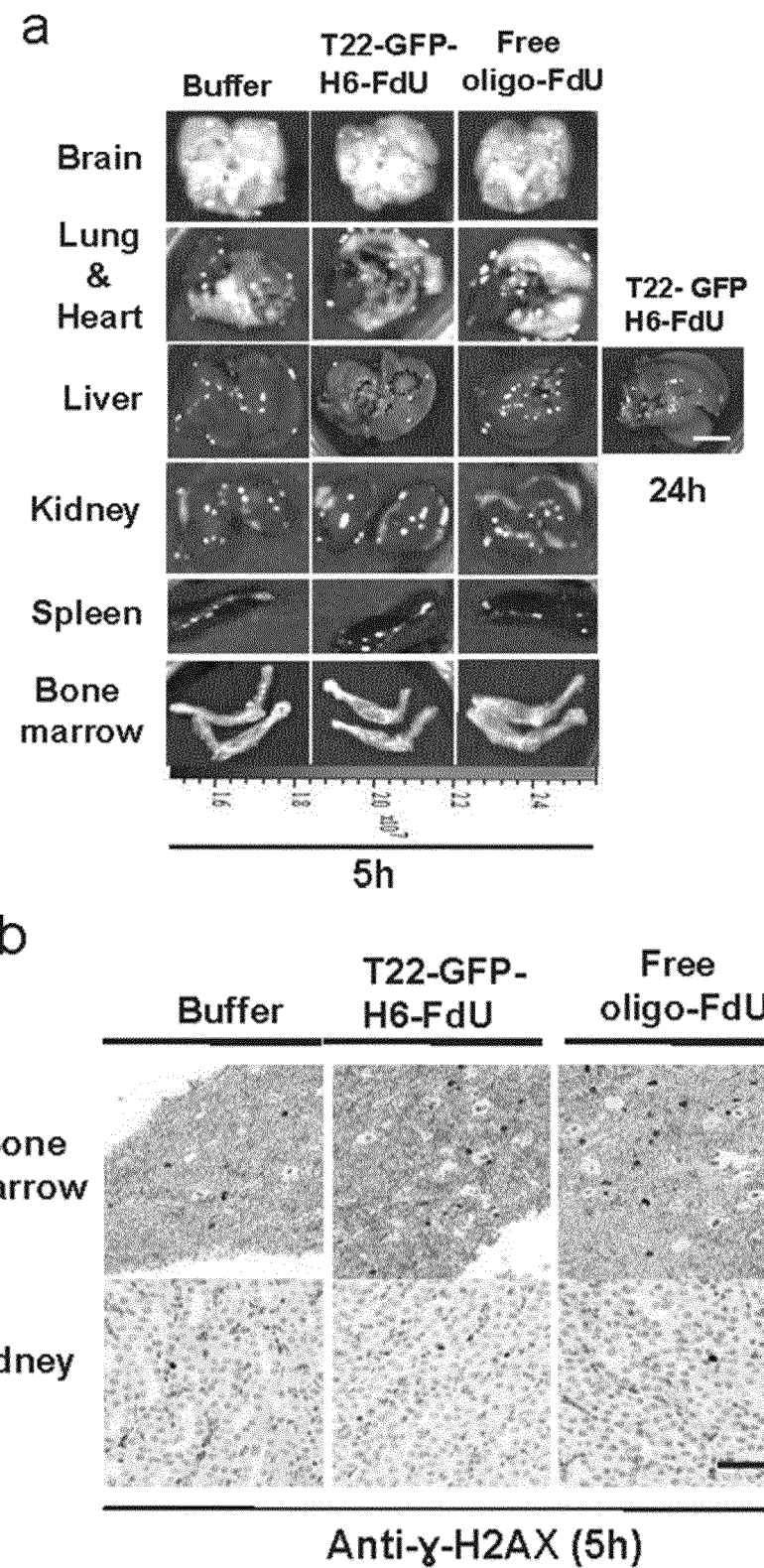
FIG. 11. Negligible T22-GFP-116-FdU biodistribution or toxicity on non-tumor tissues. (a) Undetectable T22-GFP-H6-FdU emitted fluorescence in normal tissues, except for a transient accumulation 5 h after a 100 µg dose, in the liver, which disappears at 24 h. Liver emitted fluorescence is transient and significantly lower than the one registered in tumor tissue. Tumor/Liver ratio=7.5 (see tumor intensity in FIG. 2b, which was registered in the same experiment) Scale bar, 1 cm. (b) Representative images depicting a similarly low level of DNA double strand break induction in normal bone marrow 5 h after T22-GFP-H6-FdU or free oligo-FdU administration, as measured by anti-g-H2AX, an effect that is not present in any other normal tissue analyzed. (c) Representative images depicting the lack of histopathological alterations in H&E stained tissue or apoptotic induction in H&E stained samples of CXCR4$^+$ (bone marrow) and CXCR4− (brain, kidney, liver, lung and heart) normal tissues 24 h after the administration of a 100 µg dose of T22-GFP-H6-FdU or an equimolecular 554 dose of free oligo-FdU. Note that the transient nanoconjugate distribution to liver or the DNA damage induced in bone marrow do not lead to cytotoxicity on these no-tumor tissues. (d) Lack of differences in body weight among groups registered along time in the regression of metastases experiment. (e) Lack of differences in body weight among groups registered along time in the prevention of metastases experiment. Scale bar, 100 µm.
Figure 11:
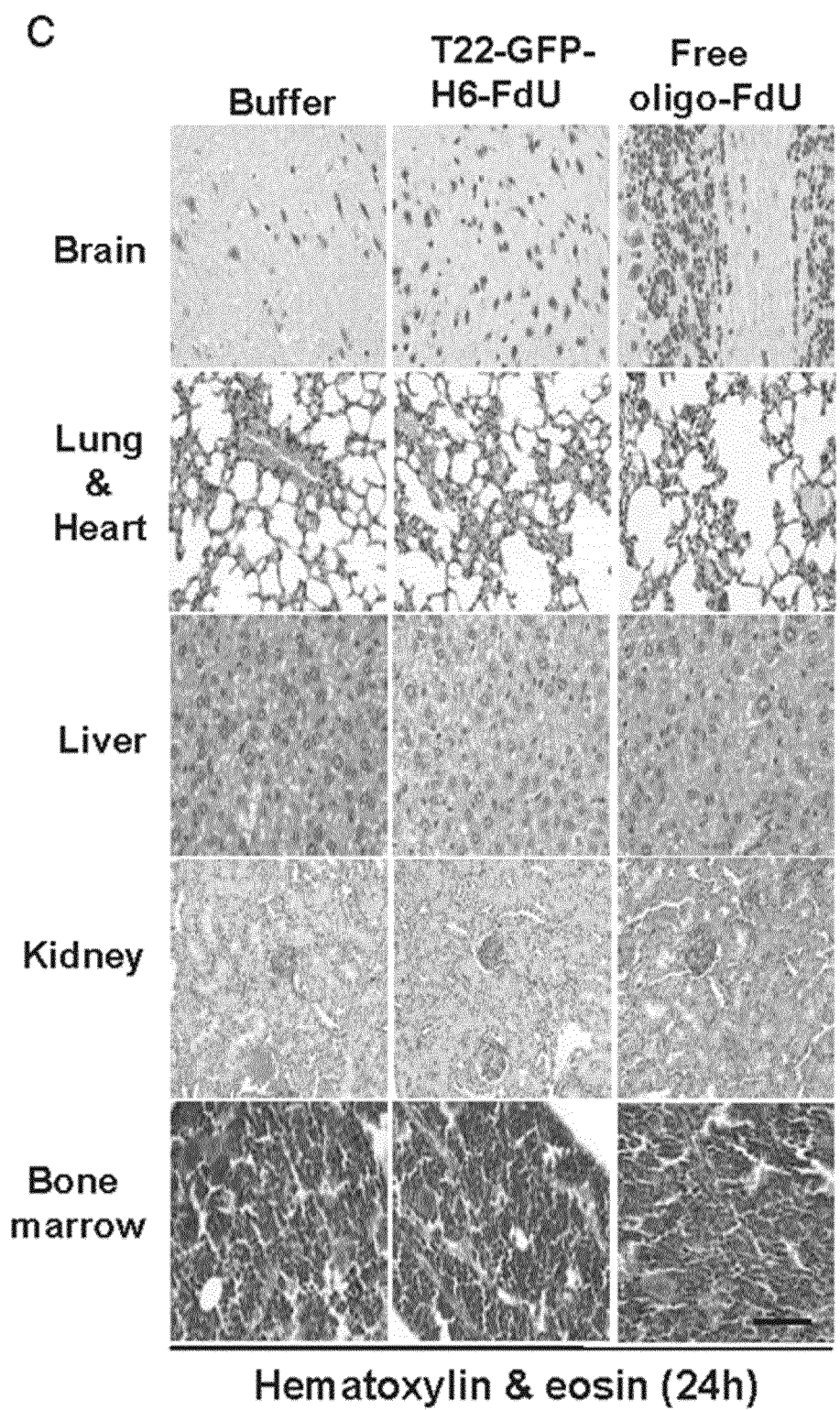
Figure 11:
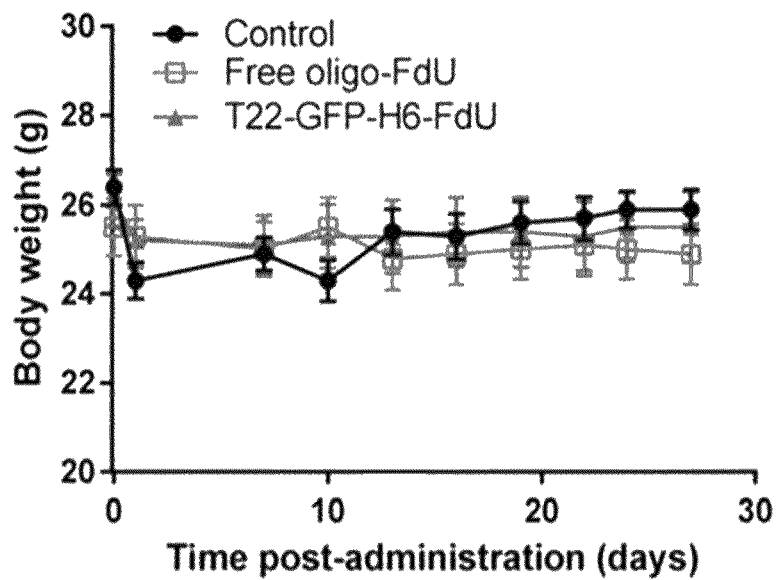
Figure 11:
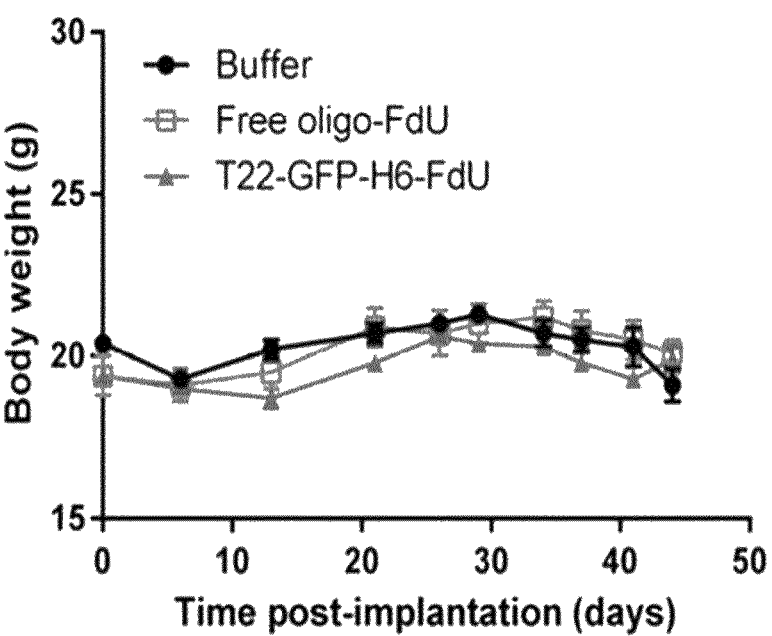
Figure 12:
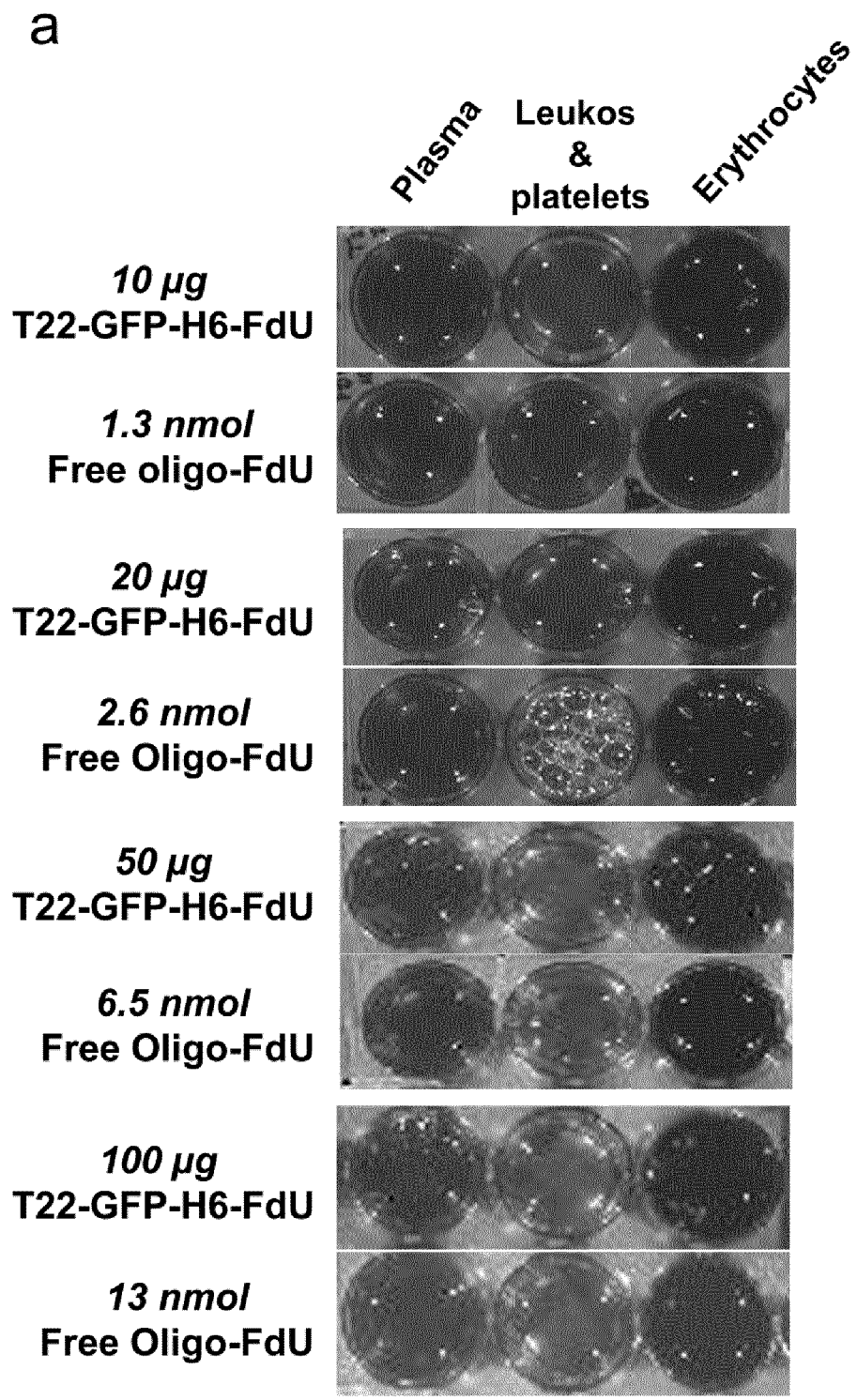
FIG. 12. Undetectable T22-GFP-116-FdU accumulation in bone marrow 92 or circulating blood cells. (a) Lack of fluorescence emission in erythrocytes, leucocytes or platelets isolated from blood using a Ficoll density gradient 5 h after the administration of T22-GFP-H6-FdU at doses in the 10-100 µg range, or control equimolecular doses of free FdU (1.3-13.0 nmol range). (b) Undetectable fluorescence emission observed in isolated leukocytes and platelet pellets after the Ficoll protocol. (c) Lack of fluorescence emission in spleen or bone marrow obtained 5 h after the treatment of mice with single injections of T22-GFP-H6-FdU or control free oligo-FdU in the dose range described in (a).
Figure 12:
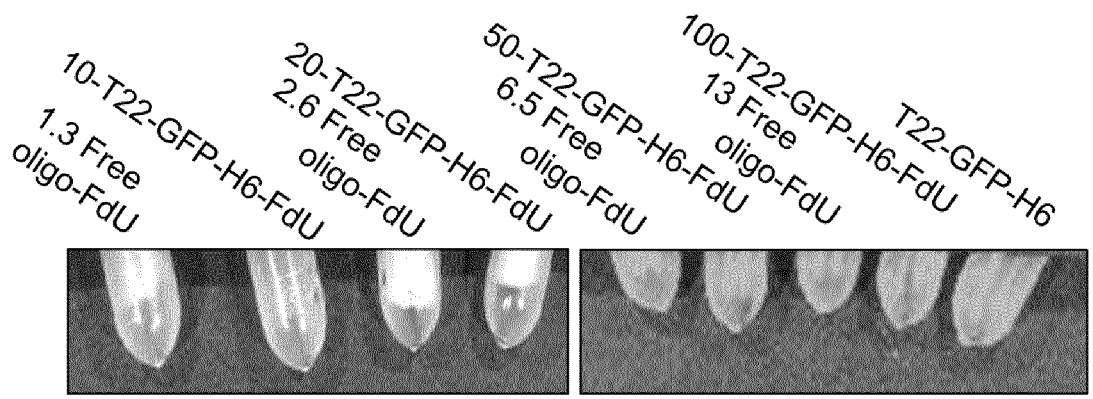
Figure 12:
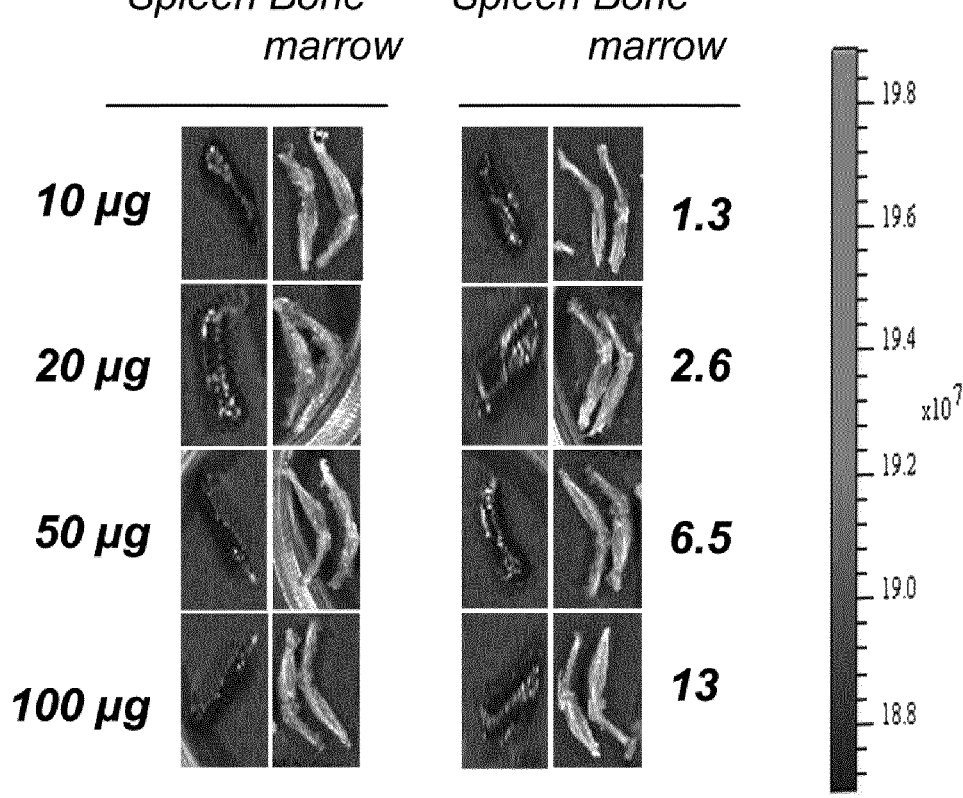

To estimate T22-GFP-H6-FdU therapeutic window, its biodistribution and induction of DNA damage or apoptosis in non-tumor tissues were analyzed. T22-GFP-H6-FdU injection lead to highly selective tumor tissue accumulation (FIG. 6b) as measured by fluorescence emission, whereas uptake in CXCR4 positive (bone marrow, spleen) or CXCR4 negative (kidney, lung, brain, heart or liver) normal tissues was undetectable, except for a transient accumulation in the liver (FIG. 11a), in the same experiment. Moreover, the level of DSBs, detected by anti-gH2AX IHC, in normal bone marrow 5 h after treatment was similar to that induced by free oligo-FdU (FIG. 11b), whereas it was undetectable in liver. DSB induction did not lead to apoptosis or histological alteration since they were not detected in bone marrow or liver 24 h post-administration (FIG. 11c). Therefore, consistently with the negligible nanoconjugate distribution to normal tissues, the lack of detectable apoptosis or histological alterations in all analyzed tissues, including bone marrow or circulating blood monocytes (FIG. 12), and the lack of mouse body weight loss in the regression (FIG. 11d) or prevention (FIG. 11e) of metastases experiments, or any sign of clinical toxicity indicate a wide therapeutic index for T22-GFP-H6-FdU at a dosage that achieves potent antimetastatic effect.

The invention claimed is:

1. A fusion protein comprising:
   (i) a polycationic peptide, wherein the polycationic peptide comprises a sequence selected from the group consisting of SEQ ID NO: 5, SEQ ID NO: 6, SEQ ID NO: 7, and SEQ ID NO: 8;
   (ii) an intervening polypeptide region conjugated to at least three chemotherapy agents, wherein the intervening polypeptide is selected from the group consisting of SEQ ID NO: 36, SEQ ID NO: 37, SEQ ID NO: 38, SEQ ID NO: 39, SEQ ID NO:40, cystatin B, cystatin C, cystatin D, cystatin M, and a variant having one or more mutations selected from the group consisting of a G4W, a G4R, a V48D, a V48L, a G50S, a K71N, a S72G, a L73P, a L82R and a T83S mutation with respect to the numbering in SEQ ID NO: 40; and
   (iii) a polyhistidine region.

2. The fusion protein according to claim 1 wherein the polyhistidine region comprises between 2 and 10 contiguous histidine residues.

3. The fusion protein according to claim 1 wherein the polycationic peptide is located at the N-terminus and the polyhistidine region is located at the C-terminus of the fusion protein or wherein the polyhistidine region is located at the N-terminus and the polycationic peptide is located at the C-terminus of the fusion protein, and/or wherein the polycationic peptide is connected to the intervening polypeptide via a first peptide linker and/or wherein the intervening polypeptide is connected to the polyhistidine region via a second peptide linker, wherein the first peptide linker comprises SEQ ID NO: 33 or SEQ ID NO: 34.

4. The fusion protein according to claim 1 wherein the at least three chemotherapy agents are the same or different.

5. The fusion protein according to claim 1 wherein the chemotherapy agent is an antimetabolite which is a pyrimidine analogue or an oligomeric form thereof.

6. The fusion protein according to claim 5 wherein the pyrimidine analogue is floxuridine.

7. A nanoparticle comprising multiple copies of the fusion protein according to claim 1.

8. The nanoparticle of claim 7, where the nanoparticle has a diameter of between 10 and 100 nm.

* * * * *